US007011094B2

(12) United States Patent
Rapacki et al.

(10) Patent No.: US 7,011,094 B2
(45) Date of Patent: Mar. 14, 2006

(54) BRONCHIAL FLOW CONTROL DEVICES AND METHODS OF USE

(75) Inventors: Alan Rapacki, Redwood City, CA (US); Michael Barrett, Campbell, CA (US)

(73) Assignee: Emphasys Medical, Inc., Redwood City, CA (US)

( * ) Notice: Subject to any disclaimer, the term of this patent is extended or adjusted under 35 U.S.C. 154(b) by 205 days.

(21) Appl. No.: 10/627,517

(22) Filed: Jul. 25, 2003

(65) Prior Publication Data

US 2004/0060563 A1    Apr. 1, 2004

Related U.S. Application Data

(63) Continuation-in-part of application No. 10/270,792, filed on Oct. 10, 2002, and a continuation-in-part of application No. 09/797,910, filed on Mar. 2, 2001, now Pat. No. 6,694,979.

(60) Provisional application No. 60/429,902, filed on Nov. 27, 2002, provisional application No. 60/399,273, filed on Jul. 26, 2002.

(51) Int. Cl.
*A62B 9/00*    (2006.01)
*A61B 9/06*    (2006.01)
*A61F 2/06*    (2006.01)
*A61F 2/04*    (2006.01)
*A61F 11/00*   (2006.01)

(52) U.S. Cl. ............................ 128/207.15; 128/207.14; 128/207.16; 128/207.29; 128/200.24; 128/200.26; 128/912; 623/1.24; 623/1.25; 623/1.26; 623/23.65; 623/23.68; 623/23.7; 606/108; 606/200; 606/213; 606/217; 604/48; 604/249; 604/256

(58) Field of Classification Search ............ 128/207.14, 128/207.15, 207.16, 207.29, 200.24, 200.26, 128/912; 623/1.24, 1.25, 1.26, 23.65, 23.68, 623/23.7; 606/108, 200, 213, 217; 604/48, 604/249, 256
See application file for complete search history.

(56) References Cited

U.S. PATENT DOCUMENTS

| 2,981,254 | A | 4/1961 | Vanderbilt ................... 128/350 |
| 3,657,744 | A | 4/1972 | Ersek .......................... 128/334 |
| 3,788,327 | A | 1/1974 | Donowitz et al. ........... 128/350 |
| 3,874,388 | A | 4/1975 | King et al. .................. 128/334 |
| 4,014,318 | A | 3/1977 | Dockum et al. ................ 128/1 |
| 4,086,665 | A | 5/1978 | Poirier ............................ 623/1 |
| 4,212,463 | A | 7/1980 | Repinski et al. ............. 273/418 |
| 4,250,873 | A | 2/1981 | Bonnet ........................ 600/104 |

(Continued)

FOREIGN PATENT DOCUMENTS

EP    0621 015 A1    10/1994

(Continued)

OTHER PUBLICATIONS

Al Jishi et al., "Selective Bronchial Occlusion for Treatment of Bullous Interstitial Emphysema and Bronchopleural Fistula." *J. of Pediatric Surgery*, 29:1545-1547, 1994.

(Continued)

*Primary Examiner*—Henry Bennett
*Assistant Examiner*—Nihir Patel
(74) *Attorney, Agent, or Firm*—Fred C. Hernandez; Stephanie Seidman; Fish & Richardson P.C

(57) ABSTRACT

A flow control device includes a sealing component that can be positioned within a bronchial lumen. The sealing component can comprise two or more overlapping segments that are movable relative to one another such that the segments collectively form a seal that can expand and contract in size to fit within and seal bronchial lumens of various sizes.

13 Claims, 67 Drawing Sheets

U.S. PATENT DOCUMENTS

| | | | |
|---|---|---|---|
| 4,302,854 A | 12/1981 | Runge | 3/1.7 |
| 4,477,930 A | 10/1984 | Totten et al. | 3/1.5 |
| 4,710,192 A | 12/1987 | Liotta et al. | 623/1 |
| 4,732,152 A | 3/1988 | Wallsten et al. | 128/343 |
| 4,759,758 A | 7/1988 | Gabbay | 623/2 |
| 4,774,942 A | 10/1988 | Moellers | 128/205.24 |
| 4,795,449 A | 1/1989 | Schneider et al. | 604/329 |
| 4,808,183 A | 2/1989 | Panje | 623/9 |
| 4,819,664 A | 4/1989 | Nazari | 128/207.15 |
| 4,830,003 A | 5/1989 | Wolff et al. | 128/343 |
| 4,832,680 A | 5/1989 | Haber et al. | 600/31 |
| 4,846,836 A | 7/1989 | Reich | 623/11 |
| 4,850,999 A | 7/1989 | Planck | 623/1 |
| 4,852,568 A | 8/1989 | Kensey | 128/325 |
| 4,877,025 A | 10/1989 | Hanson | 128/107.16 |
| 4,879,998 A | 11/1989 | Moellers | 128/205.24 |
| 4,934,999 A | 6/1990 | Bader | 600/29 |
| 4,968,294 A | 11/1990 | Salama | 600/30 |
| 4,990,151 A | 2/1991 | Wallsten | 606/108 |
| 5,061,274 A | 10/1991 | Kensey | 606/213 |
| 5,116,360 A | 5/1992 | Pinchuk et al. | 623/1 |
| 5,116,564 A | 5/1992 | Jansen et al. | 264/255 |
| 5,123,919 A | 6/1992 | Sauter et al. | 623/2 |
| 5,151,105 A | 9/1992 | Kwan-Gett | 623/1 |
| 5,158,548 A | 10/1992 | Lau et al. | 606/194 |
| 5,161,524 A | 11/1992 | Evans | 128/203.15 |
| 5,306,234 A | 4/1994 | Johnson | 604/49 |
| 5,352,240 A | 10/1994 | Ross | 623/2 |
| 5,358,518 A | 10/1994 | Camilli | 623/2 |
| 5,366,478 A | 11/1994 | Brinkerhoff et al. | 660/213 |
| 5,382,261 A | 1/1995 | Palmaz | 606/158 |
| 5,392,775 A | 2/1995 | Adkins et al. | 128/207.16 |
| 5,409,019 A | 4/1995 | Wilk | 128/898 |
| 5,411,507 A | 5/1995 | Heckele | 606/108 |
| 5,411,552 A | 5/1995 | Andersen et al. | 623/2 |
| 5,413,599 A | 5/1995 | Imachi et al. | 623/2 |
| 5,417,226 A | 5/1995 | Juma | 128/885 |
| 5,445,626 A | 8/1995 | Gigante | 604/349 |
| 5,453,090 A | 9/1995 | Martinez et al. | 606/108 |
| 5,486,154 A | 1/1996 | Kelleher | 600/104 |
| 5,499,995 A | 3/1996 | Teirstein | 606/192 |
| 5,500,014 A | 3/1996 | Quijano et al. | 623/2 |
| 5,562,608 A | 10/1996 | Sekins et al. | 604/20 |
| 5,645,519 A | 7/1997 | Lee et al. | 600/114 |
| 5,645,565 A | 7/1997 | Rudd et al. | 606/213 |
| 5,649,906 A | 7/1997 | Gory et al. | 606/108 |
| 5,660,175 A | 8/1997 | Dayal | 128/207.15 |
| 5,662,713 A | 9/1997 | Andersen et al. | 623/12 |
| 5,683,451 A | 11/1997 | Lenker et al. | 623/1 |
| 5,697,968 A | 12/1997 | Rogers et al. | 623/1 |
| 5,755,770 A | 5/1998 | Ravenscroft | 623/1 |
| 5,800,339 A | 9/1998 | Salama | 600/29 |
| 5,803,080 A | 9/1998 | Freitag | 128/207.14 |
| 5,840,081 A | 11/1998 | Andersen et al. | 623/2 |
| 5,851,232 A | 12/1998 | Lois | 623/1 |
| 5,855,587 A | 1/1999 | Hyon et al. | 606/188 |
| 5,855,597 A | 1/1999 | Jayaraman | 623/1 |
| 5,855,601 A | 1/1999 | Bessler et al. | 623/2 |
| 5,910,144 A | 6/1999 | Hayashi | 606/108 |
| 5,944,738 A | 8/1999 | Amplatz et al. | 606/213 |
| 5,947,997 A | 9/1999 | Pavcnik et al. | 606/213 |
| 5,954,766 A * | 9/1999 | Zadno-Azizi et al. | 623/1.24 |
| 5,957,949 A | 9/1999 | Leonhardt et al. | 606/194 |
| 5,976,174 A | 11/1999 | Ruiz | 606/213 |
| 5,980,455 A | 11/1999 | Daniel et al. | 600/235 |
| 5,984,965 A | 11/1999 | Knapp et al. | 623/12 |
| 6,007,575 A | 12/1999 | Samuels | 623/1 |
| 6,009,614 A | 1/2000 | Morales | 29/516 |
| 6,020,380 A | 2/2000 | Killian | 514/570 |
| 6,022,312 A | 2/2000 | Chaussy et al. | 600/29 |
| 6,027,508 A | 2/2000 | Ren et al. | 606/108 |
| 6,027,525 A | 2/2000 | Suh et al. | 623/1 |
| 6,051,022 A | 4/2000 | Cai et al. | 623/2 |
| 6,068,635 A | 5/2000 | Gianotti | 606/108 |
| 6,068,638 A | 5/2000 | Makower | 606/159 |
| 6,077,291 A | 6/2000 | Das | 606/213 |
| 6,083,255 A | 7/2000 | Laufer et al. | 607/96 |
| 6,123,663 A | 9/2000 | Rebuffat | |
| 6,135,729 A | 10/2000 | Aber | 417/420 |
| 6,135,991 A | 10/2000 | Muni et al. | 604/509 |
| 6,141,855 A | 11/2000 | Morales | 29/516 |
| 6,162,245 A | 12/2000 | Jayaraman | 623/1.15 |
| 6,168,614 B1 | 1/2001 | Andersen et al. | 623/1 |
| 6,174,323 B1 | 1/2001 | Biggs et al. | 606/232 |
| 6,183,520 B1 | 2/2001 | Pintauro et al. | 623/23.64 |
| 6,190,381 B1 | 2/2001 | Olsen et al. | 606/32 |
| 6,200,333 B1 | 3/2001 | Laufer | 607/96 |
| 6,206,918 B1 | 3/2001 | Campbell et al. | 623/2.32 |
| 6,234,996 B1 | 5/2001 | Bagaoisan et al. | 604/97.01 |
| 6,240,615 B1 | 6/2001 | Kimes et al. | 29/516 |
| 6,245,102 B1 | 6/2001 | Jayaraman | 623/1.15 |
| 6,247,471 B1 | 6/2001 | Bower et al. | 128/205.21 |
| 6,258,100 B1 * | 7/2001 | Alferness et al. | 606/108 |
| 6,270,527 B1 | 8/2001 | Campbell et al. | 623/2.18 |
| 6,280,464 B1 | 8/2001 | Hayashi | 623/1.11 |
| 6,287,290 B1 | 9/2001 | Perkins et al. | 604/516 |
| 6,293,951 B1 * | 9/2001 | Alferness et al. | 606/108 |
| 6,302,893 B1 | 10/2001 | Limon et al. | 606/108 |
| 6,312,407 B1 | 11/2001 | Zadno-Azizi et al. | 604/103.03 |
| 6,325,777 B1 | 12/2001 | Zadno-Azizi et al. | 604/97.01 |
| 6,325,778 B1 | 12/2001 | Zadno-Azizi et al. | 604/99.02 |
| 6,327,772 B1 | 12/2001 | Zadno-Azizi et al. | 29/557 |
| 6,328,689 B1 | 12/2001 | Gonzalez | 600/37 |
| 6,355,014 B1 | 3/2002 | Zadno-Azizi et al. | 604/99.02 |
| 6,398,775 B1 | 6/2002 | Perkins et al. | 604/514 |
| 6,402,754 B1 | 6/2002 | Gonzalez | 606/69 |
| 6,416,554 B1 | 7/2002 | Alferness et al. | 623/23.65 |
| 6,458,076 B1 | 10/2002 | Pruitt et al. | 600/146 |
| 6,485,407 B1 | 11/2002 | Alferness et al. | 600/37 |
| 6,491,706 B1 | 12/2002 | Alferness et al. | 606/157 |
| 6,493,589 B1 | 12/2002 | Medhkour et al. | 607/99 |
| 6,510,846 B1 | 1/2003 | O'Rourke | 128/200.21 |
| 6,527,761 B1 | 3/2003 | Soltesz et al. | 604/516 |
| 6,558,318 B1 | 5/2003 | Daniel et al. | 600/213 |
| 6,592,594 B1 | 7/2003 | Rimbaugh et al. | 606/108 |
| 6,632,243 B1 * | 10/2003 | Zadno-Azizi et al. | 623/1.24 |
| 6,679,264 B1 * | 1/2004 | Deem et al. | 128/207.16 |
| 6,685,739 B1 | 2/2004 | DiMatteo et al. | 623/1.24 |
| 6,694,979 B1 * | 2/2004 | Deem et al. | 128/207.14 |
| 6,699,231 B1 | 3/2004 | Sterman et al. | 604/509 |
| 6,840,243 B1 * | 1/2005 | Deem et al. | 128/207.16 |
| 6,860,847 B1 * | 3/2005 | Alferness et al. | 600/37 |
| 6,901,927 B1 * | 6/2005 | Deem et al. | 128/200.24 |
| 6,904,909 B1 * | 6/2005 | Andreas et al. | 128/200.24 |
| 2001/0025132 A1 | 9/2001 | Alferness et al. | 600/37 |
| 2001/0037808 A1 | 11/2001 | Deem et al. | 128/200.24 |
| 2001/0041906 A1 | 11/2001 | Gonzalez | 606/191 |
| 2001/0051799 A1 | 12/2001 | Ingenito | 604/516 |
| 2001/0052344 A1 | 12/2001 | Doshi | 128/207 |
| 2001/0056274 A1 | 12/2001 | Perkins et al. | 604/516 |
| 2002/0007831 A1 | 1/2002 | Davenport et al. | 128/200.24 |
| 2002/0026233 A1 | 2/2002 | Shaknovich | 623/1.24 |
| 2002/0062120 A1 | 5/2002 | Perkins et al. | 604/516 |
| 2002/0077593 A1 | 6/2002 | Perkins et al. | 604/96.01 |
| 2002/0077696 A1 | 6/2002 | Zadno-Azizi et al. | 623/1.24 |
| 2002/0087153 A1 | 7/2002 | Roschak et al. | 606/27 |
| 2002/0095209 A1 | 7/2002 | Zadno-Azizi et al. | 623/1.24 |
| 2002/0111619 A1 | 8/2002 | Keast et al. | 606/41 |
| 2002/0111620 A1 | 8/2002 | Cooper et al. | 606/41 |
| 2002/0112729 A1 | 8/2002 | DeVore et al. | 128/207.15 |
| 2002/0138135 A1 | 9/2002 | Duerig et al. | 623/1.24 |
| 2003/0018327 A1 | 1/2003 | Truckai et al. | 606/32 |
| 2003/0018344 A1 | 1/2003 | Kaji et al. | 606/130 |
| 2003/0050648 A1 | 3/2003 | Alferness et al. | 606/108 |

| | | | |
|---|---|---|---|
| 2003/0070682 A1 | 4/2003 | Wilson et al. | 128/207.16 |
| 2003/0070683 A1 | 4/2003 | Deem et al. | 128/207.16 |
| 2003/0075169 A1 | 4/2003 | Deem et al. | 128/200.19 |
| 2003/0075170 A1 | 4/2003 | Deem et al. | 128/200.19 |
| 2003/0083671 A1 | 5/2003 | Rimbaugh et al. | 606/108 |
| 2003/0164168 A1 | 9/2003 | Shaw et al. | 128/200.24 |
| 2003/0181922 A1* | 9/2003 | Alferness | 606/108 |
| 2003/0183235 A1 | 10/2003 | Rimbaugh et al. | 128/207.15 |
| 2003/0192550 A1 | 10/2003 | Deem et al. | 128/207.14 |
| 2003/0192551 A1 | 10/2003 | Deem et al. | 128/207.14 |
| 2003/0199972 A1 | 10/2003 | Zadno-Azizi et al. | 623/1.24 |
| 2003/0212452 A1 | 11/2003 | Zadno-Azizi et al. | 623/1.24 |
| 2004/0016435 A1 | 1/2004 | Deem et al. | 128/207.14 |
| 2004/0039250 A1 | 2/2004 | Tholfsen et al. | 600/104 |
| 2004/0055606 A1 | 3/2004 | Hendrickson et al. | 128/207.14 |
| 2004/0074491 A1 | 4/2004 | Hendricksen et al. | 128/200.19 |
| 2004/0089306 A1 | 5/2004 | Hundertmark et al. | 128/207.14 |
| 2004/0134487 A1 | 7/2004 | Deem et al. | 128/200.19 |
| 2004/0154621 A1 | 8/2004 | Deem et al. | 128/206.24 |
| 2005/0033344 A1* | 2/2005 | Dillard et al. | 606/191 |
| 2005/0051163 A1 | 3/2005 | Deem et al. | 128/200.24 |
| 2005/0066974 A1 | 3/2005 | Fields et al. | 128/207.14 |
| 2005/0137714 A1* | 6/2005 | Gonzalez et al. | 623/23.65 |

FOREIGN PATENT DOCUMENTS

| | | |
|---|---|---|
| EP | 0621 015 B1 | 10/1994 |
| EP | 1 078 601 A2 | 2/2001 |
| EP | 01/28433 A1 | 4/2001 |
| EP | 1 151 729 A1 | 11/2001 |
| GB | 2324729 | 4/1998 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 A1 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 A1 | 12/1999 |
| WO | 00/15149 | 3/2000 |
| WO | 00/42950 | 7/2000 |
| WO | 00/51510 | 9/2000 |
| WO | 00/62699 | 10/2000 |
| WO | 00/78386 A1 | 12/2000 |
| WO | 00/78407 A1 | 12/2000 |
| WO | 01/02042 A1 | 1/2001 |
| WO | 01/03642 A1 | 1/2001 |
| WO | 01/05334 A1 | 1/2001 |
| WO | 01/10313 A1 | 2/2001 |
| WO | 01/10314 A2 | 2/2001 |
| WO | 01/12104 A1 | 2/2001 |
| WO | 01/13839 A1 | 3/2001 |
| WO | 01/13908 A2 | 3/2001 |
| WO | 01/45590 A2 | 6/2001 |
| WO | 01/49213 A2 | 7/2001 |
| WO | 01/54585 A1 | 8/2001 |
| WO | 01/54625 A1 | 8/2001 |
| WO | 01/54685 A1 | 8/2001 |
| WO | 01/66190 | 9/2001 |
| WO | 01/66190 A2 | 9/2001 |
| WO | 01/74271 A1 | 10/2001 |
| WO | 01/87170 | 11/2001 |
| WO | 01/87170 A1 | 11/2001 |
| WO | 01/89366 A2 | 11/2001 |
| WO | 01/95786 A2 | 12/2001 |
| WO | 02/05884 A2 | 1/2002 |
| WO | 02/22072 A2 | 3/2002 |
| WO | 02/32333 A1 | 4/2002 |
| WO | 02/34322 A2 | 5/2002 |
| WO | 02/38038 A2 | 5/2002 |
| WO | 02/47575 A2 | 6/2002 |
| WO | 02/056794 A2 | 7/2002 |
| WO | 02/064045 A1 | 8/2002 |
| WO | 02/064190 A2 | 8/2002 |
| WO | 02/064190 A3 | 8/2002 |
| WO | 02/069823 A2 | 9/2002 |
| WO | 02/069823 A3 | 9/2002 |
| WO | 02/094087 A1 | 11/2002 |
| WO | 03/022124 A2 | 3/2003 |
| WO | 03/030975 | 4/2003 |
| WO | 03/099164 | 4/2003 |
| WO | 03/079944 A1 | 10/2003 |
| WO | 03/088912 A2 | 10/2003 |
| WO | 2004/010845 | 2/2004 |

OTHER PUBLICATIONS

Article: "Autocath® 100—Nonsurgical, Intraurethral Bladder Control Device for Incontinent and Retentive Women—Dr. Kulisz's Development".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc. No.: 1988-241181/198834 (citing Russian Application No. SU4026409, published Feb. 21, 1986), Russian Patent No. SU 1371700.

Derwent# 008650867 WPI Acc. No.: 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919.

Lewis et al., "Pulmonary Interstitial Emphysema: Selective Broncial Occlusion with a Swan-Ganz Catheter", *Archives of Disease in Childhood*, 63:313-315, 1988.

Mathew et al., "Selective bronchial obstruction for treatment of bullous interstitial emphysema." *J. of Ped.*, 96:475-477, 1980.

Okada et al., "Emergent Bronchofiberoptic Bronchial Occlusion for Intractable Pneumothorax with Severe Emphysema", *The Jap. J. of Thor. And Cardio. Sur.*, 46: 1078-1081, 1998.

Puhakka et al., "Acute Bronchial Obstruction: An Experimental Rabbit Model Study", *Int. J. of Pediatric Otorhinolaryngology*, 18:107-118, 1989.

Snider et al., *The Definition of Emphysema*: Report of the National Heart Lung and Blood Institute, Division of Lung Diseases Workshop, *Am. Rev. Respir. Dis.*, 132:182-185, 1985.

Woodring et al., "Pneumothorax ex Vacuo", *CHEST*, 100: 1102-1124, 1996.

\* cited by examiner

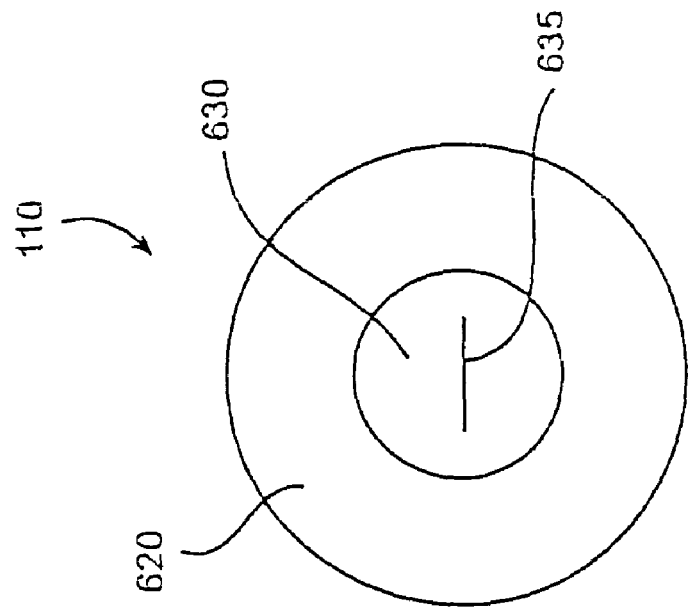
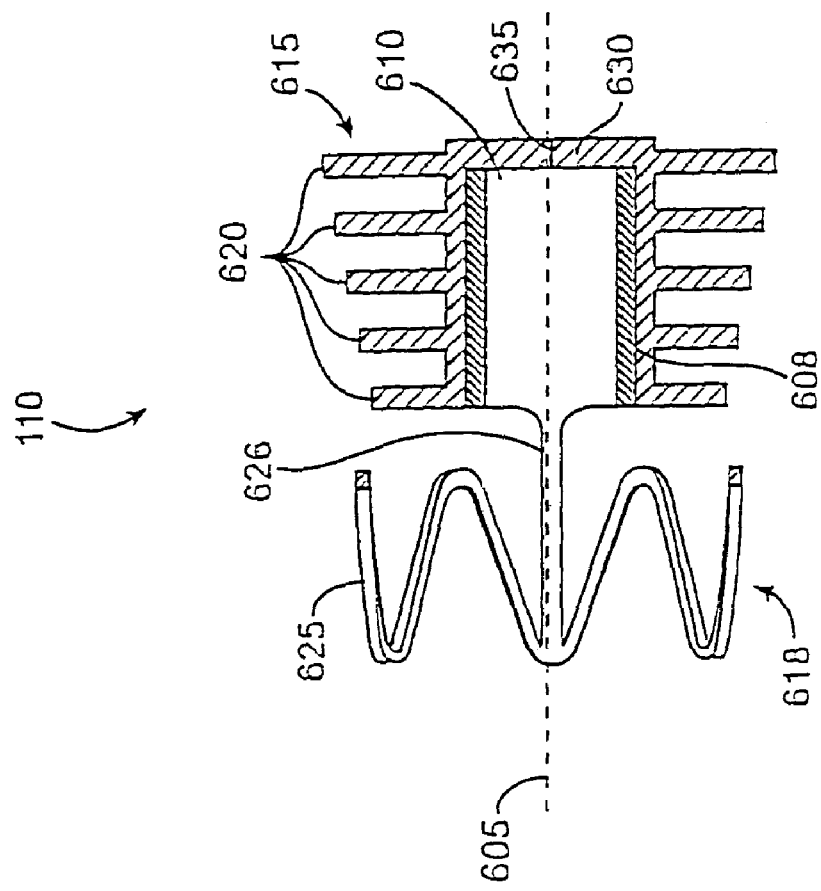

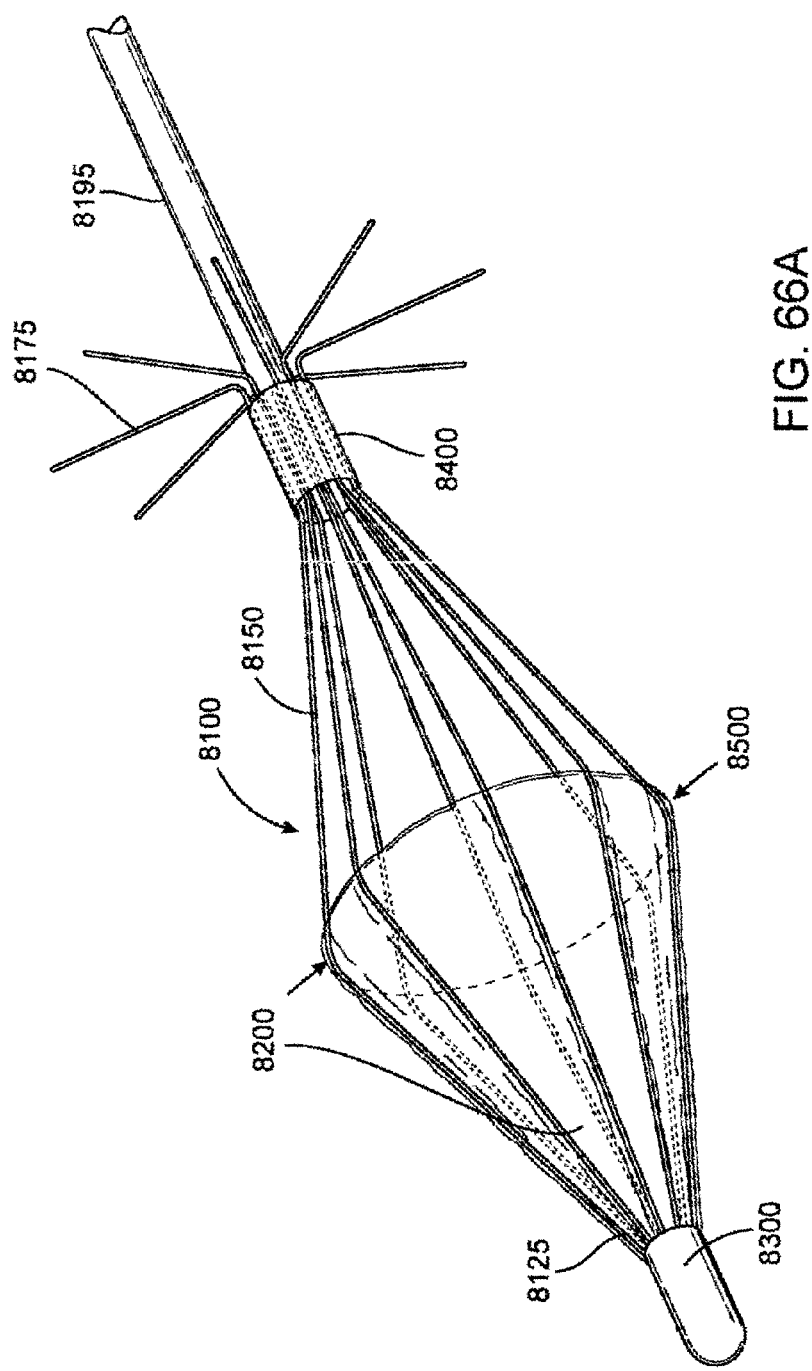

BRONCHIAL FLOW CONTROL DEVICES AND METHODS OF USE

REFERENCE TO PRIORITY DOCUMENTS

This application claims priority of the following co-pending U.S. provisional patent applications: (1) U.S. Provisional Patent Application Ser. No. 60/399,273, entitled "Implantable Bronchial Isolation Devices", filed Jul. 26, 2002; and (2) U.S. Provisional Patent Application Ser. No. 60/429,902, entitled "Implantable Bronchial Isolation Devices", filed Nov. 27, 2002. Priority of the aforementioned filing dates is hereby claimed, and the disclosures of the Provisional Patent Applications are hereby incorporated by reference in their entirety.

This application is a continuation-in-part of the following co-pending patent applications: (1) U.S. patent application Ser. No. 09/797,910, entitled "Methods and Devices for Use in Performing Pulmonary Procedures", filed Mar. 2, 2001, now U.S. Pat. No. 6,694,979; and (2) U.S. patent application Ser. No. 10/270,792, entitled "Bronchial Flow Control Devices and Methods of Use", filed Oct. 10, 2002. The aforementioned applications are hereby incorporated by reference in their entireties.

BACKGROUND OF THE INVENTION

1. Field of the Invention

This invention relates generally to methods and devices for use in performing pulmonary procedures and, more particularly, to procedures for treating various lung diseases.

2. Description of the Related Art

Pulmonary diseases, such as chronic obstructive pulmonary disease, (COPD), reduce the ability of one or both lungs to fully expel air during the exhalation phase of the breathing cycle. The term "Chronic Obstructive Pulmonary Disease" (COPD) refers to a group of diseases that share a major symptom, dyspnea. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema. While each has distinct anatomic and clinical considerations, many patients may have overlapping characteristics of damage at both the acinar (as seen in emphysema) and the bronchial (as seen in bronchitis) levels.

Emphysema is a condition of the lung characterized by the abnormal permanent enlargement of the airspaces distal to the terminal bronchiole, accompanied by the destruction of their walls, and without obvious fibrosis. (Snider, G. L. et al: The Definition of Emphysema: Report of the National Heart Lung And Blood Institute, Division of lung Diseases Workshop. (Am Rev. Respir. Dis. 132:182, 1985). It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Lung reduction surgery is a conventional method of treating emphysema. According to the lung reduction procedure, a diseased portion of the lung is surgically removed, which makes more of the pleural space available to accommodate the functioning, healthy portions of the lung. The lung is typically accessed through a median sternotomy or small lateral thoracotomy. A portion of the lung, typically the periphery of the upper lobe, is freed from the chest wall and then resected, e.g., by a stapler lined with bovine pericardium to reinforce the lung tissue adjacent the cut line and also to prevent air or blood leakage. The chest is then closed and tubes are inserted to remove air and fluid from the pleural cavity. The conventional surgical approach is relatively traumatic and invasive, and, like most surgical procedures, is not a viable option for all patients.

Some recently proposed treatments include the use of devices that isolate a diseased region of the lung in order to reduce the volume of the diseased region, such as by collapsing the diseased lung region. According to such treatments, isolation devices are implanted in airways feeding the targeted region of the lung to regulate fluid flow to the diseased lung region in order to fluidly isolate the region of the lung. These implanted isolation devices can be, for example, one-way valves that allow flow in the exhalation direction only, occluders or plugs that prevent flow in either direction, or two-way valves that control flow in both directions. However, such devices are still in the development stages. For example, some valves have been found to wrinkle and create fluid leak paths when implanted in a bronchial lumen of a diameter other than that near the diameter of the valve. Thus, there is much need for improvement in the design, flexibility, and functionality of such isolation devices.

In view of the foregoing, there is a need for improved methods and devices for regulating fluid flow to a diseased lung region.

SUMMARY

Disclosed are methods and devices for regulating fluid flow to and from a region of a patient's lung, such as to achieve a desired fluid flow dynamic to a lung region during respiration and/or to induce collapse in one or more lung regions. In one aspect of the invention, there is disclosed a flow control device that can be implanted in a bronchial passageway. The flow control device can include a sealing component that can be positioned within a bronchial lumen. The sealing component can comprise two or more overlapping segments that are movable relative to one another such that the segments collectively form a seal that can expand and contract in size to fit within and seal bronchial lumens of various sizes.

Also disclosed is a flow control device that can be implanted in a bronchial passageway. The flow control device comprises a retainer frame comprising a core, a first set of deployable arms projecting from the core, and a second set of deployable arms projecting from the core. The flow control device further comprises a sealing component comprising two or more overlapping segments that are movable relative to one another such that the segments collectively form a seal that can expand and contract in size to fit within and seal bronchial lumens of various sizes.

Also disclosed is a method of regulating fluid flow to and from a region of an individual's lung. The method comprises placing a flow control device in a bronchial passage in communication with the region, the flow control device having a first set of one or more deployable arms in a collapsed configuration; and radially expanding the first set of one or more deployable arms into engagement with a wall of the bronchial passage to anchor the flow control device therein. The flow control device has a plurality of overlapping segments that are movable relative to one another and collectively form a seal with a wall of the bronchial lumen that can expand and contract in size.

Also disclosed is a flow control device for placement in a body lumen. The flow control device can comprise a frame comprising a plurality of struts connected to a distal hub, at least a portion of each strut biased outwardly from the distal hub. The flow control device further comprises a membrane coupled to the struts thereby forming an umbrella shape. The frame urges the membrane into engagement with a wall of the body lumen to form a seal therewith.

Other features and advantages of the present invention should be apparent from the following description of various embodiments, which illustrate, by way of example, the principles of the invention.

BRIEF DESCRIPTION OF THE DRAWINGS

FIG. 10 shows a side, cross-sectional view of the flow control device of FIG. 9.

FIG. 11 shows a front, plan view of the flow control device of FIG. 9.

FIG. 66A shows a perspective view of an umbrella style flow control device according to one embodiment.

DETAILED DESCRIPTION

Unless defined otherwise, all technical and scientific terms used herein have the same meaning as is commonly understood by one of skill in the art to which the invention(s) belong.

Figure 1:
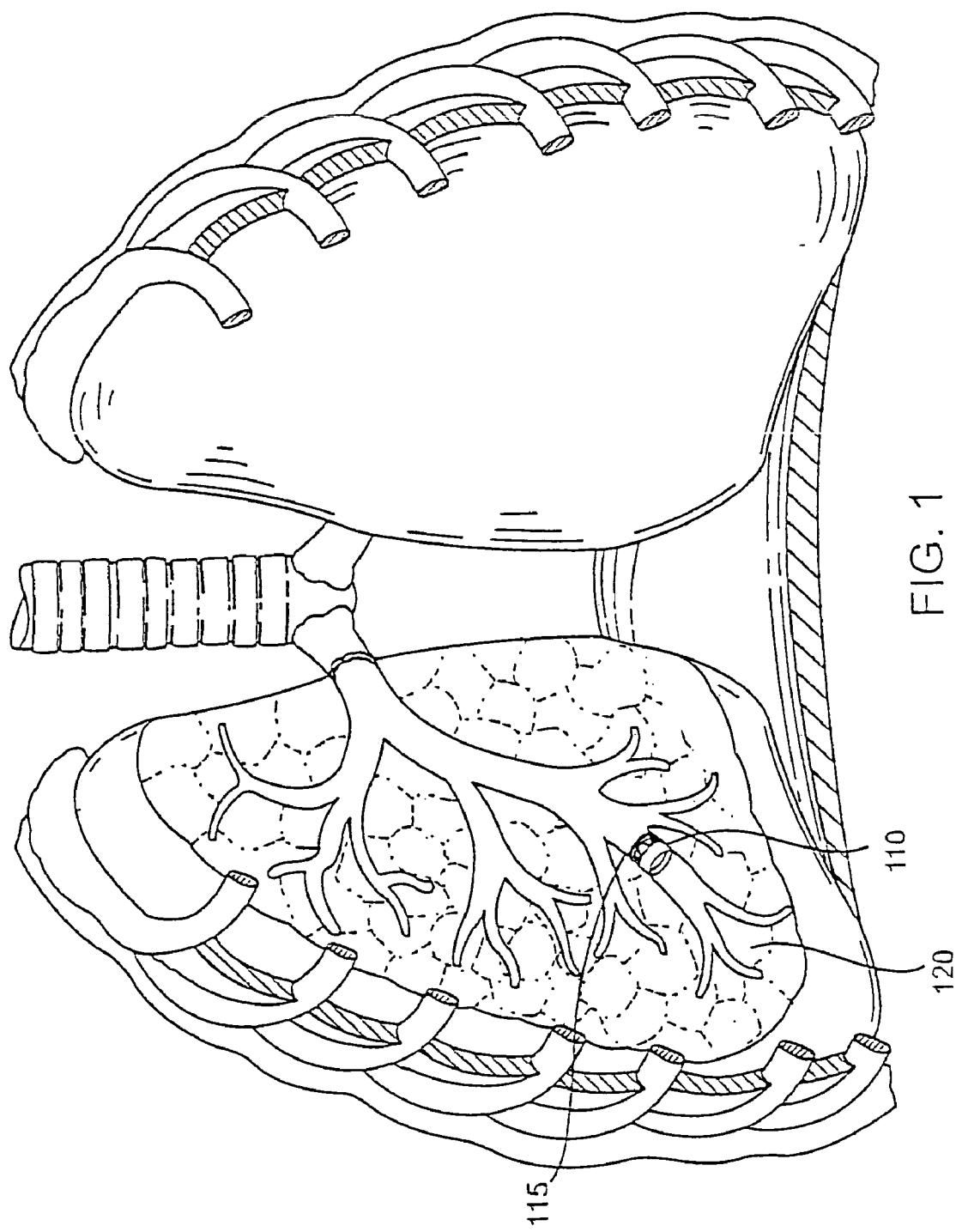
FIG. 1 shows an anterior view of a pair of human lungs and a bronchial tree with a flow control device implanted in a bronchial passageway to bronchially isolate a region of the lung.

Disclosed are methods and devices for regulating fluid flow to and from a region of a patient's lung, such as to achieve a desired fluid flow dynamic to a lung region during respiration and/or to induce collapse in one or more lung regions. An identified region of the lung (referred to herein as the "targeted lung region") is targeted for treatment, such as to modify the air flow to the targeted lung region or to achieve volume reduction or collapse of the targeted lung region. The targeted lung region is then bronchially isolated to regulate airflow into and/or out of the targeted lung region through one or more bronchial passageways that feed air to the targeted lung region. As shown in FIG. 1, the bronchial isolation of the targeted lung region is accomplished by implanting a flow control device 110 into a bronchial passageway 115 that feeds air to a targeted lung region 120. The flow control device 110 regulates airflow through the bronchial passageway 115 in which the flow control device 110 is implanted, as described in more detail below. The flow control device 110 can be implanted into the bronchial passageway using a delivery system, such as the delivery system catheter described herein.

Exemplary Lung Regions

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer to a lung lobe or a lung segment. Such lung regions conform to portions of the lungs that are known to those skilled in the art. However, it should be appreciated that the term lung region does necessarily refer to a lung lobe or a lung segment, but can also refer to some other defined division or portion of a human or non-human lung.

Figure 2:
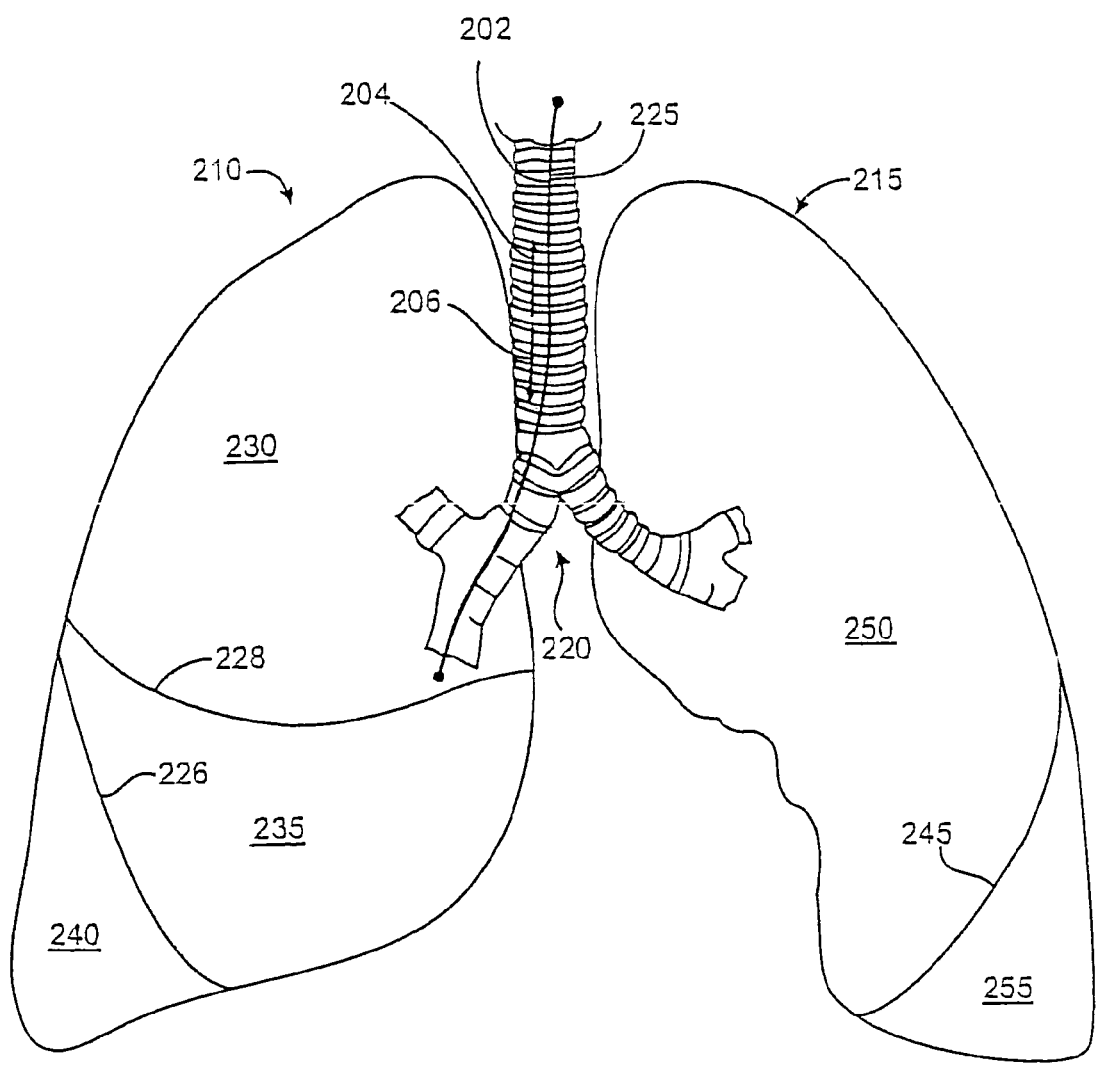
FIG. 2 shows an anterior view of a pair of human lungs and a bronchial tree.

FIG. 2 shows an anterior view of a pair of human lungs 210, 215 and a bronchial tree 220 that provides a fluid pathway into and out of the lungs 210, 215 from a trachea 225, as will be known to those skilled in the art. As used herein, the term "fluid" can refer to a gas, a liquid, or a combination of gas(es) and liquid(s). For clarity of illustration, FIG. 2 shows only a portion of the bronchial tree 220, which is described in more detail below with reference to FIG. 4.

Throughout this description, certain terms are used that refer to relative directions or locations along a path defined from an entryway into the patient's body (e.g., the mouth or nose) to the patient's lungs. The path generally begins at the patient's mouth or nose, travels through the trachea into one or more bronchial passageways, and terminates at some point in the patient's lungs. For example, FIG. 2 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 2 points in the proximal direction. The term "distal direction" refers to the direction along such a path 202 that points toward the patient's lung and away from the mouth or nose. The distal direction is generally the same as the inhalation direction when the patient breathes. The arrow 206 in FIG. 2 points in the distal direction.

With reference to FIG. 2, the lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 135.

As shown in FIG. 2, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied air via respective lobar bronchi, as described in detail below.

Figure 3A:
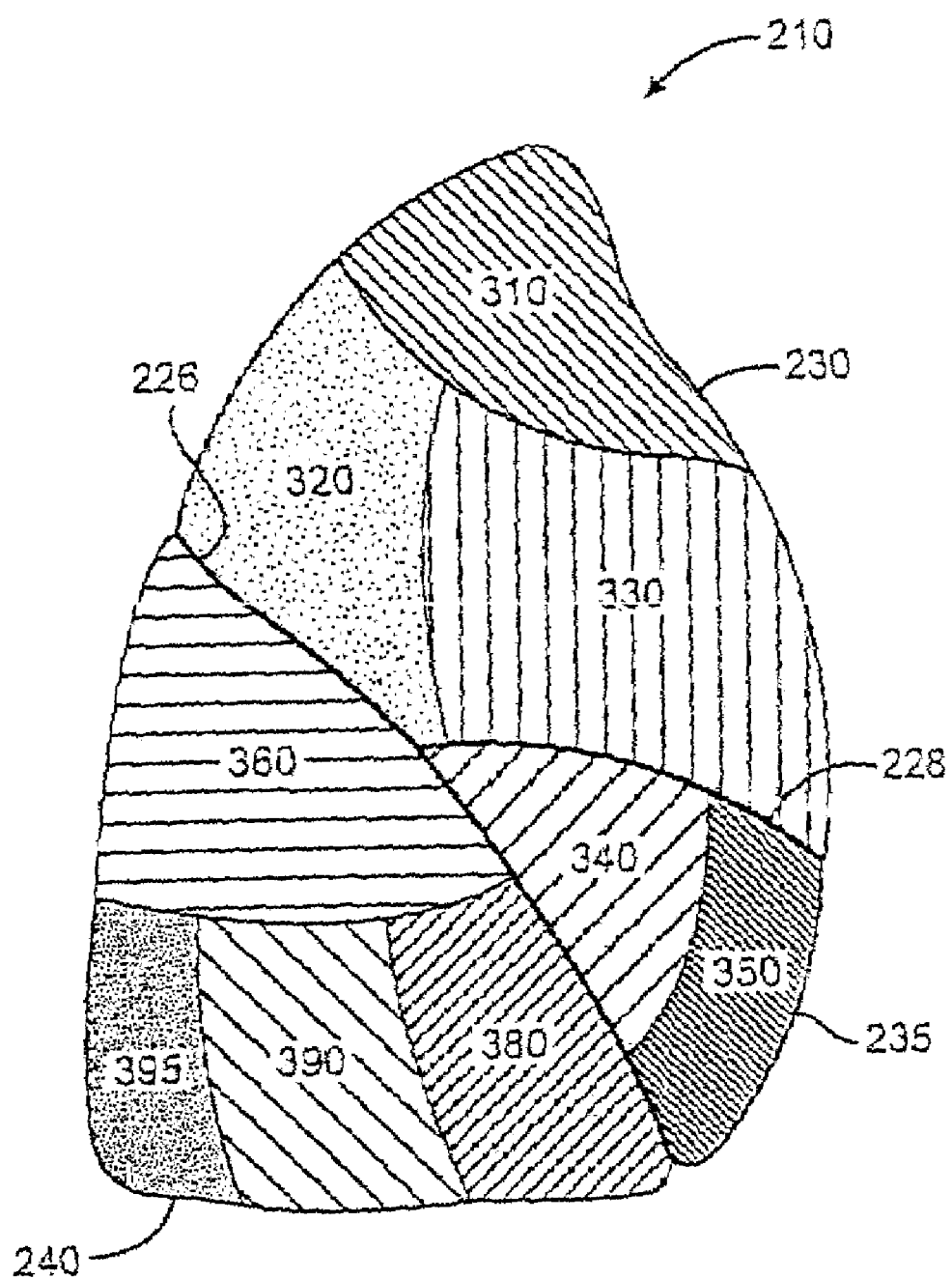
FIG. 3A shows a lateral view of the right lung.

FIG. 3A is a lateral view of the right lung 210. The right lung 210 is subdivided into lung regions comprised of a plurality of bronchopulmonary segments. Each bronchopulmonary segment is directly supplied air by a corresponding segmental tertiary bronchus, as described below. The bronchopulmonary segments of the right lung 210 include a right apical segment 310, a right posterior segment 320, and a right anterior segment 330, all of which are disposed in the right upper lobe 230. The right lung bronchopulmonary segments further include a right lateral segment 340 and a right medial segment 350, which are disposed in the right middle lobe 235. The right lower lobe 240 includes bronchopulmonary segments comprised of a right superior segment 360, a right medial basal segment (which cannot be seen from the lateral view and is not shown in FIG. 3A), a right anterior basal segment 380, a right lateral basal segment 390, and a right posterior basal segment 395.

Figure 3B:
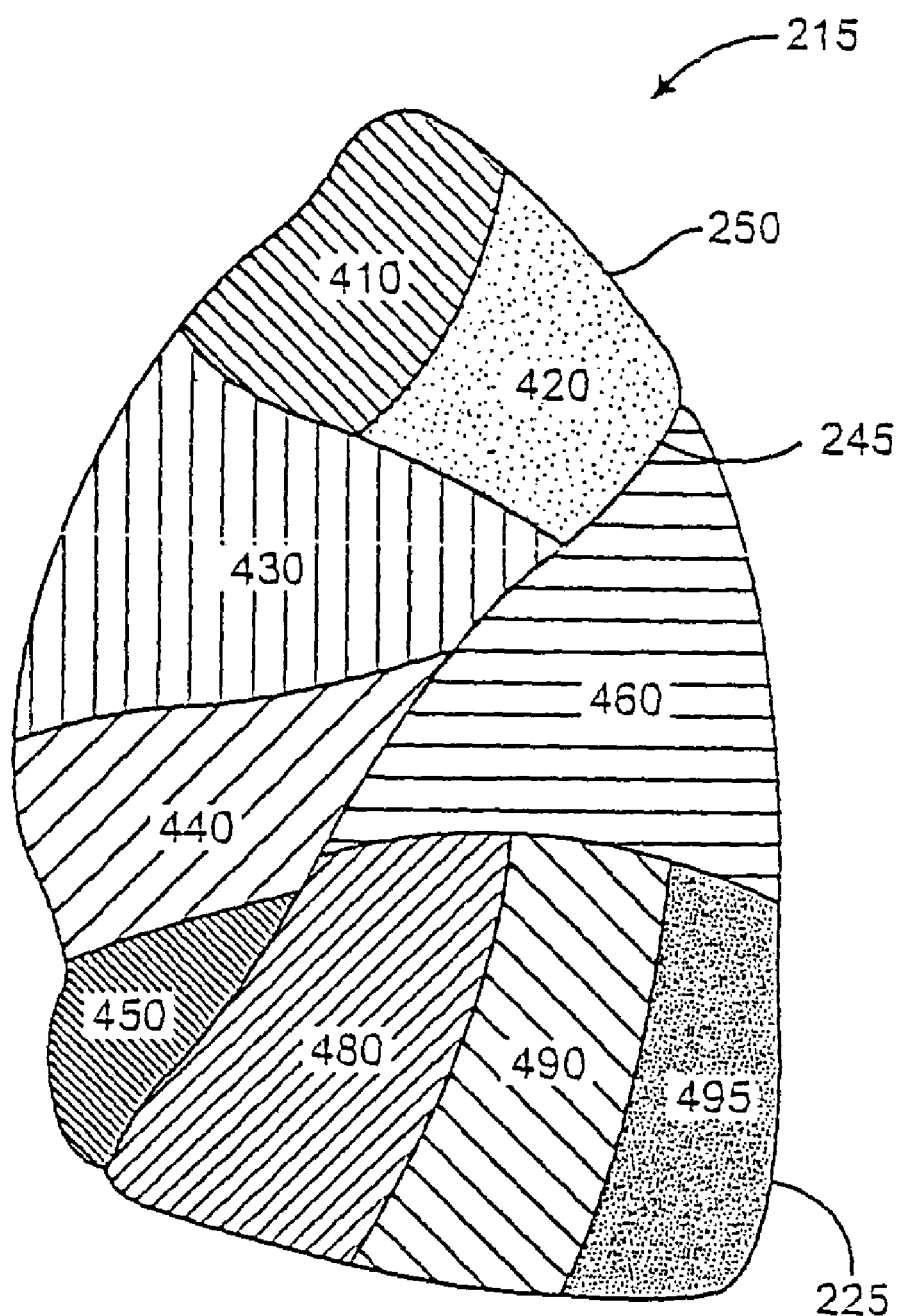
FIG. 3B shows a lateral view of the left lung.

FIG. 3B shows a lateral view of the left lung 215, which is subdivided into lung regions comprised of a plurality of bronchopulmonary segments. The bronchopulmonary segments include a left apical segment 410, a left posterior segment 420, a left anterior segment 430, a left superior segment 440, and a left inferior segment 450, which are disposed in the left lung upper lobe 250. The lower lobe 255 of the left lung 215 includes bronchopulmonary segments comprised of a left superior segment 460, a left medial basal segment (which cannot be seen from the lateral view and is not shown in FIG. 3B), a left anterior basal segment 480, a left lateral basal segment 490, and a left posterior basal segment 495.

Figure 4:
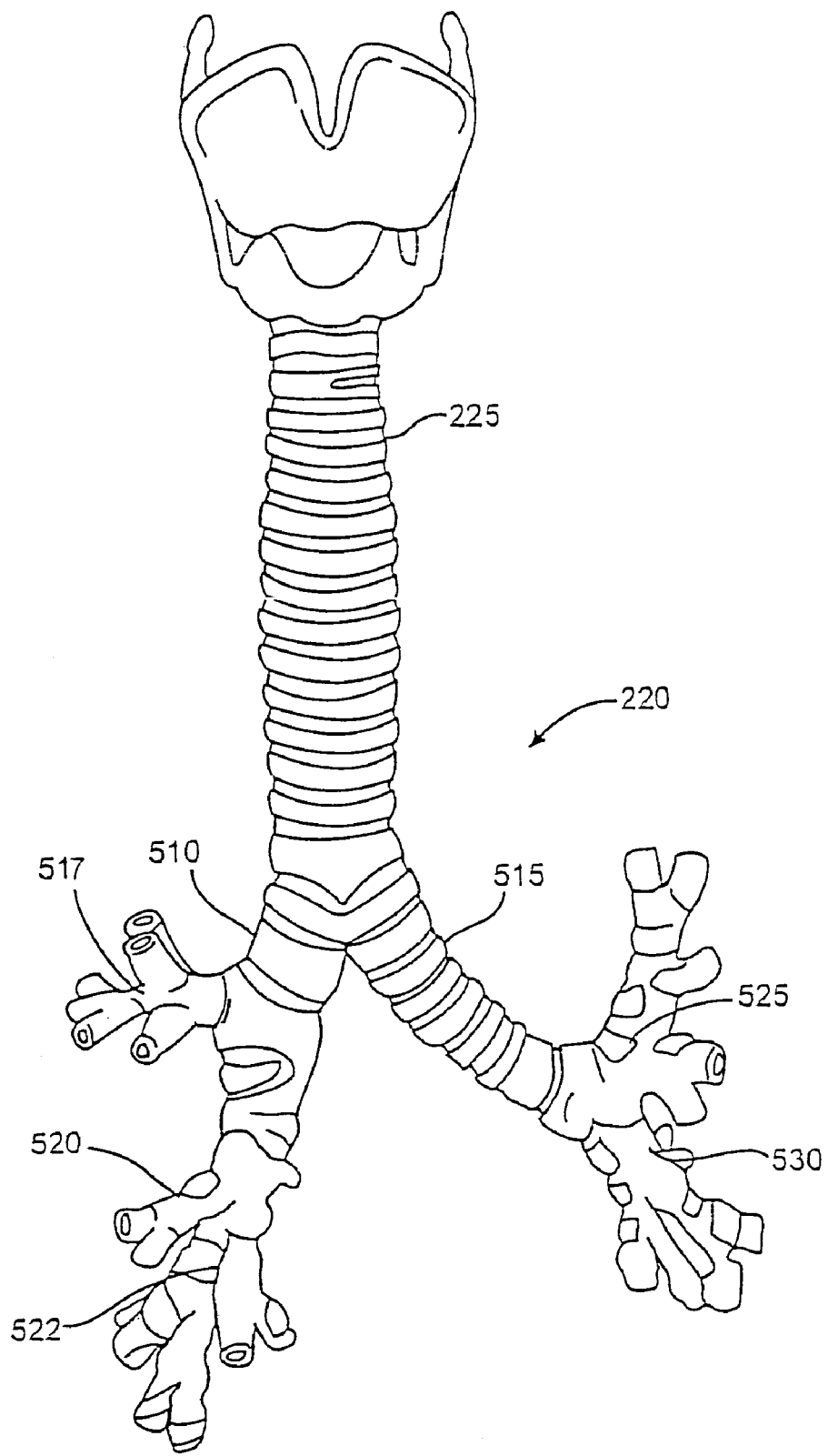
FIG. 4 shows an anterior view of the trachea and a portion of the bronchial tree.

FIG. 4 shows an anterior view of the trachea 225 and a portion of the bronchial tree 220, which includes a network of bronchial passageways, as described below. The trachea 225 divides at a distal end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 522. The left primary bronchus 515 divides into a left upper lobar bronchus 525 and a left lower lobar bronchus 530. Each lobar bronchus, 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Stented Flow Control Devices

As discussed, the flow control device 110 can be implanted in a bronchial passageway to regulate the flow of fluid through the bronchial passageway. When implanted in a bronchial passageway, the flow control device 110 anchors within the bronchial passageway in a sealing fashion such that fluid in the bronchial passageway must pass through the flow control device in order to travel past the location where the flow control device is located. The flow control device 110 has fluid flow regulation characteristics that can be varied based upon the design of the flow control device. For example, the flow control device 110 can be configured to either permit fluid flow in two directions (i.e., proximal and distal directions), permit fluid flow in only one direction (proximal or distal direction), completely restrict fluid flow in any direction through the flow control device, or any combination of the above. The flow control device can be configured such that when fluid flow is permitted, it is only permitted above a certain pressure, referred to as the cracking pressure. As described in detail below, the flow control device 110 can also be configured such that a dilation device can be manually inserted into the flow control device 110 to vary the flow properties of the flow control device 110.

Figure 5A:
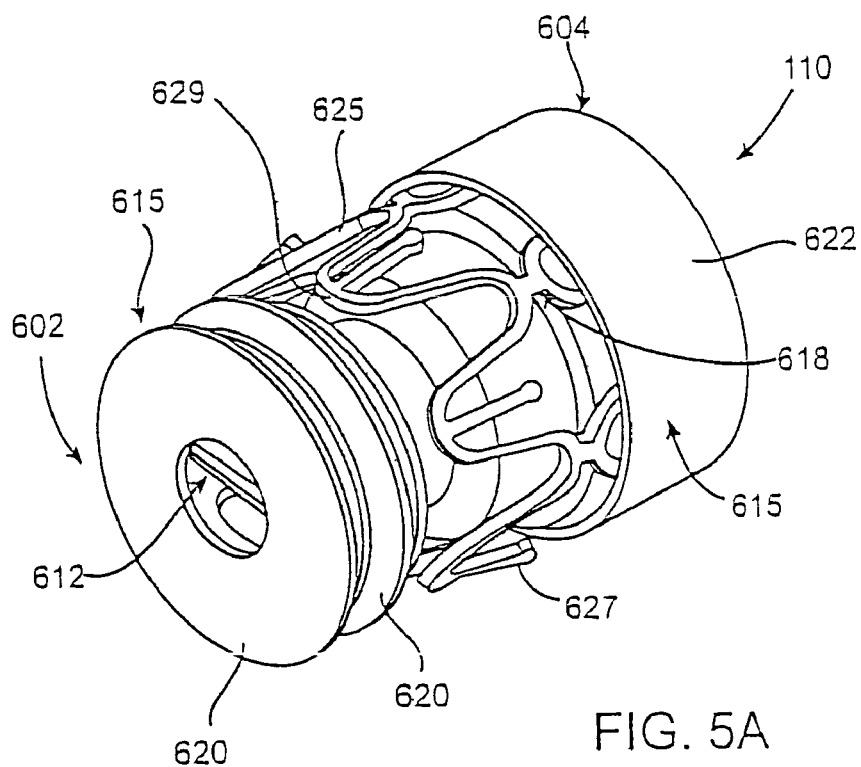
FIG. 5A shows a perspective view of a first embodiment of a flow control device that can be implanted in a body passageway.
Figure 5B:
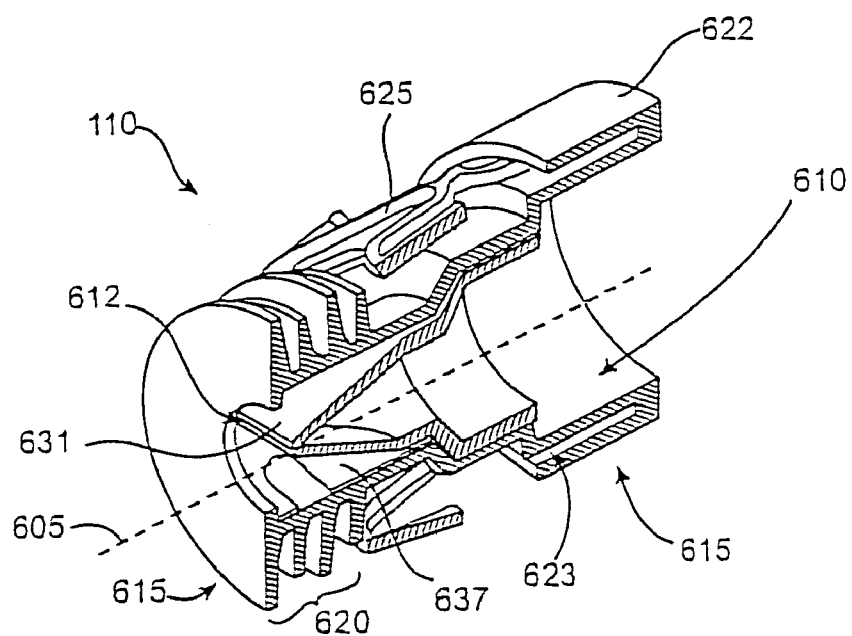
FIG. 5B shows a perspective, cross-sectional view of the flow control device of FIG. 5A.
Figure 6A:
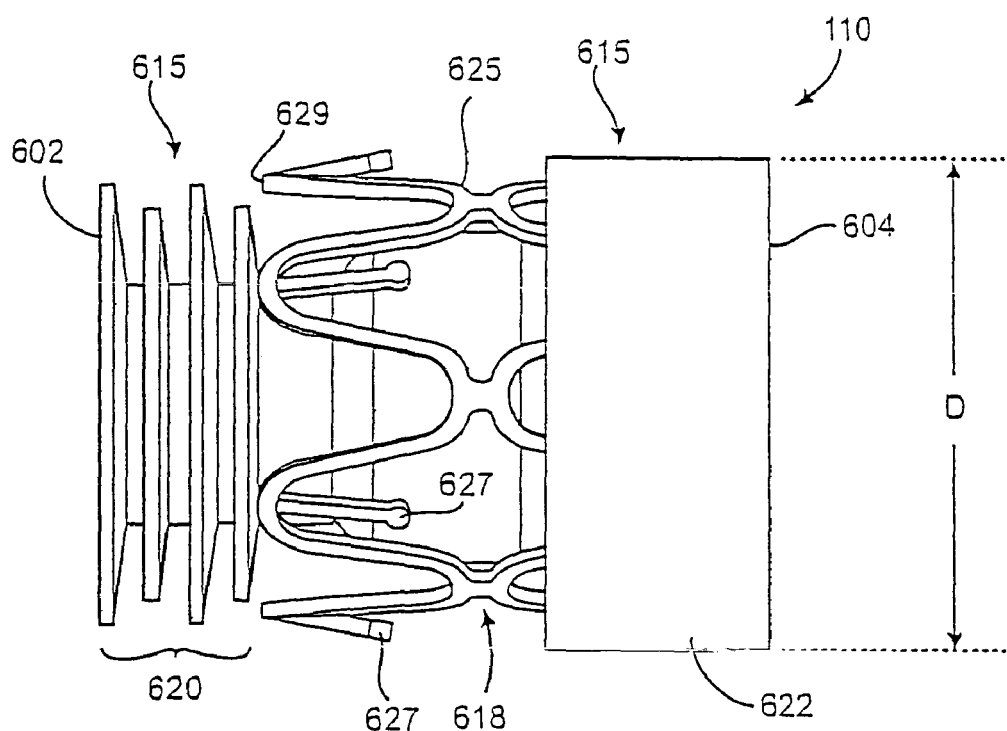
FIG. 6A shows a side view of the flow control device of FIG. 5A.
Figure 6B:
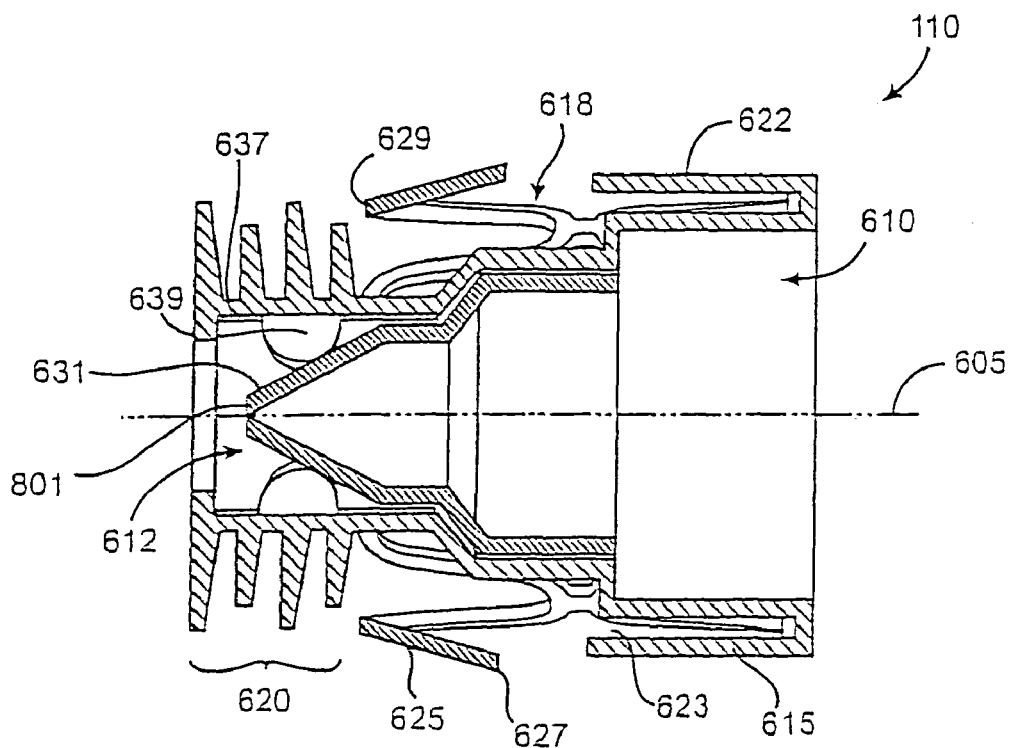
FIG. 6B shows a cross-sectional, side view of the flow control device of FIG. 5A.

FIGS. 5-6 show a first embodiment of a flow control device 110. FIG. 5A shows a perspective view of the device 110, FIG. 5B shows a perspective, cross-sectional view of the device 110, FIG. 6A shows a plan, side view of the device 110, and FIG. 6B shows a cross-sectional, plan, side view of the device 110. The flow control device 110 extends generally along a central axis 605 (shown in FIGS. 5B and 6B) and has a proximal end 602 and a distal end 604. The flow control device 110 includes a main body that defines an interior lumen 610 through which fluid can flow along a flow path that generally conforms to the central axis 605.

The flow of fluid through the interior lumen 610 is controlled by a valve member 612 that is disposed at a location along the interior lumen such that fluid must flow through the valve member 612 in order to flow through the interior lumen 610, as described more fully below. It should be appreciated that the valve member 612 could be positioned at various locations along the interior lumen 610. The valve member 612 can be made of a biocompatible material, such as a biocompatible polymer, such as silicone. The size of the valve member 612 can vary based on a variety of factors, such as the desired cracking pressure of the valve member 612.

The flow control device 110 has a general outer shape and contour that permits the flow control device 110 to fit entirely within a body passageway, such as within a bronchial passageway. Thus, as best shown in FIGS. 5A and 5B, the flow control device 110 has a generally circular shape (when viewed longitudinally along the axis 605) that will facilitate insertion of the flow control device into a bronchial passageway. A circular shape generally provides a good fit with a bronchial passageway, although it should be appreciated that the flow control device 110 can have other cross-sectional shapes that enable the device 110 to be inserted into a bronchial passageway.

With reference to FIGS. 5-6, the flow control device 110 includes an outer seal member 615 that provides a seal with the internal walls of a body passageway when the flow control device is implanted into the body passageway. The seal member 615 is manufactured of a deformable material, such as silicone or a deformable elastomer. The flow control device 110 also includes an anchor member 618 that functions to anchor the flow control device 110 within a body passageway. The configurations of the seal member 615 and the anchor member 618 can vary, as described below.

As shown in FIGS. 5-6, the seal member 615 is generally located on an outer periphery of the flow control device 110. In the embodiment shown in FIGS. 5-6, the seal member includes a series of radially-extending, circular flanges 620 that surround the outer circumference of the flow control device 110. The flanges 620 can be manufactured of silicone or other deformable elastomer. As best shown in FIG. 6B, the radial length of each flange 620 varies moving along the longitudinal length (as defined by the longitudinal axis 605 in FIG. 6B) of the flow control device 110. It should be appreciated that the radial length could be equal for all of the flanges 620 or that the radial length of each flange could vary in some other manner. For example, the flanges 620 can alternate between larger and shorter radial lengths moving along the longitudinal length of the flow control device, or the flanges can vary in a random fashion. In addition, the flanges 620 could be oriented at a variety of angles relative to the longitudinal axis 605 of the flow control device. In another embodiment, the radial length of a single flange could vary so that the circumference of the flange is sinusoidal about the center of the flange.

In the embodiment shown in FIGS. 5-6, the seal member 615 includes a cuff 622. As can be seen in the cross-sectional views of FIGS. 5B and 6B, the cuff 622 comprises a region of the seal member 615 that overlaps on itself so as to form a cavity 623 within the cuff 622. As described below, the cavity 623 can be used to retain the anchor member 618 to the seal member 615 of the flow control device 110. The cuff 622 can function in combination with the flanges 620 to seal the flow control device to the internal walls of a bronchial lumen when the flow control device is implanted in a bronchial lumen, as described below. The cuff 622 can be formed in a variety of manners, such as by folding a portion of the seal member 615 over itself, or by molding the seal member 615 to form the cuff 622.

As mentioned, the anchor member 618 functions to anchor the flow control device 110 in place when the flow control device is implanted within a body passageway, such as within a bronchial passageway. The anchor member 618 has a structure that can contract and expand in size (in a radial direction and/or in a longitudinal direction) so that the anchor member can expand to grip the interior walls of a body passageway in which the flow control device is positioned. In one embodiment, as shown in FIGS. 5 and 6, the anchor member 618 comprises an annular frame 625 that surrounds the flow control device 110. The frame 625 is formed by a plurality of struts that define an interior envelope sized to surround the interior lumen 610.

As shown in FIGS. 5-6, the struts of the frame 625 form curved, proximal ends 629 that can be slightly flared outward with respect to the longitudinal axis 605. When the flow control device 110 is placed in a bronchial lumen, the curved, proximal ends 629 can anchor into the bronchial walls and prevent migration of the flow control device in a proximal direction. The frame 625 can also have flared, distal prongs 627 that can anchor into the bronchial walls and to prevent the device 110 from migrating in a distal direction when the flow control device 110 is placed in a bronchial lumen. The frame 625 can be formed from a super-elastic material, such as Nickel Titanium (also known as Nitinol), such as by cutting the frame out of a tube of Nitinol or by forming the frame out of Nitinol wire. The super-elastic properties of Nitinol can result in the frame exerting a radial force against the interior walls of a bronchial passageway sufficient to anchor the flow control device 110 in place.

The struts are arranged so that the frame 625 can expand and contract in a manner that is entirely or substantially independent of the rest of the flow control device 110, including the valve member 612, as described more fully below. In the embodiment shown in FIGS. 5–6, the frame 625 is attached to the flow control device 110 inside the cavity 623 of the cuff 622. That is, at least a portion of the frame 625 is positioned inside the cavity 623. The frame 625 is not necessarily fixedly attached to the cavity. Rather, a portion of the frame 625 is positioned within the cavity 623 so that the frame 625 can freely move within the cavity, but cannot be released from the cavity. An attachment means can be used to attach the opposing pieces of the cuff 622 to one another so that the frame 625 cannot fall out of the cavity 623. In one embodiment, the attachment means comprises an adhesive, such as silicone adhesive, that is placed inside the cavity 623 and that adheres the opposing pieces of the cuff 622 to one another. In an alternative embodiment, described below, rivets are used to attach the opposing pieces of the cuff. It should be appreciated, however, that different attachment means could be used to secure the frame 625 to the seal member 615. Furthermore, it should be appreciated that the frame 625 is not necessarily bonded to the seal member 615. In yet another embodiment, the frame 625 can be integrally formed with the valve protector member 637, described below.

As mentioned, the valve member 612 regulates the flow of fluid through the interior lumen 610 of the flow control device 110. In this regard, the valve member 612 can be configured to permit fluid to flow in only one-direction through the interior lumen 610, to permit regulated flow in two-directions through the interior lumen 610, or to prevent fluid flow in either direction. The valve member 612 is positioned at a location along the interior lumen 610 so that fluid must travel through the valve member 612 in order to flow through the interior lumen 610.

Figure 7A:
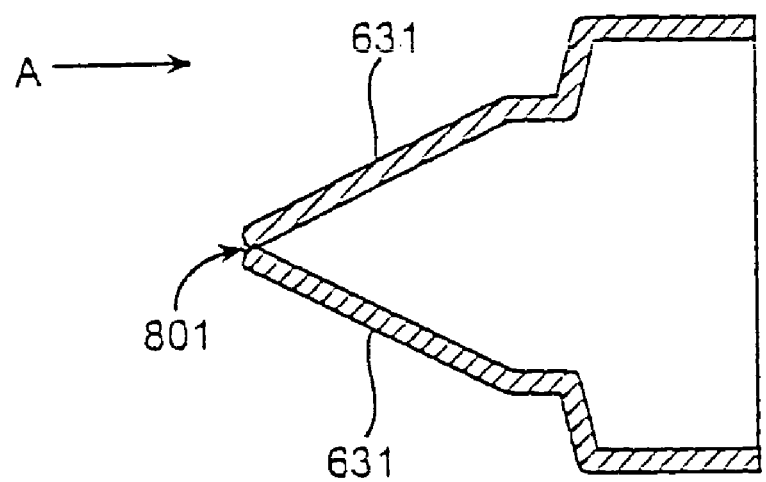
FIG. 7A shows a side, cross-sectional view of a duckbill valve in a closed state.
Figure 7B:
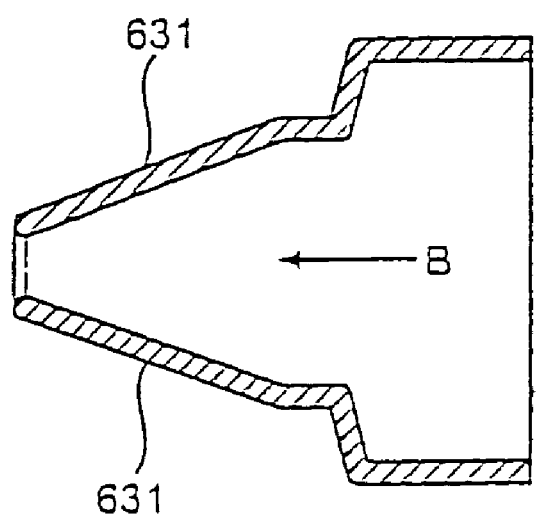
FIG. 7B shows a side, cross-sectional view of a duckbill valve in an open state.

The valve member 612 can be any type of fluid valve, and preferably is a valve that enables the cracking pressures described herein. The valve member 612 can have a smaller diameter than the frame 625 so that compression or deformation of the frame 625 in both a radial and axial direction will have little or no impact on the structure of the valve member 612. In the embodiment shown in FIGS. 5–6, the valve member 612 comprises a duckbill valve that includes two flaps 631 (shown in FIGS. 5B and 6B) that are oriented at an angle with respect to one another and that can open and close with respect to one another so as to form an opening at a lip 801 (FIG. 6B) where the flaps 631 touch one another. The duckbill valve operates according to a conventional duckbill valve in that it allows fluid flow in a first direction and prevents fluid flow in a second direction that is opposed to the first direction. For example, FIG. 7A shows a schematic side-view of the duckbill valve in a closed state, wherein the flaps 631 touch one another at the lip 801. In the closed state, the duckbill valve prevents fluid flow in a first direction, which is represented by the arrow A in FIG. 7A. However, when exposed to fluid flow in a second direction (represented by arrow B in FIG. 7B) that is opposed to the first direction, the flaps 631 separate from one another to form an opening between the flaps 631 that permits flow in the second direction, as shown in FIG. 7B.

With reference again to FIG. 6B, the valve member 612 is concentrically contained within the seal member 615. In addition, at least a portion of the valve member 612 is optionally surrounded by a rigid or semi-rigid valve protector member 637 (shown in FIGS. 5B and 6B), which is a tubular member or annular wall that is contained inside the seal member 615. In another embodiment, the valve protector can comprise a coil of wire or a ring of wire that provides some level of structural support to the flow control device. The valve protector 637 can be concentrically located within the seal member 615. Alternately, the valve member 612 can be completely molded within the seal member 615 such that the material of the seal member 615 completely surrounds the valve protector.

The valve protector member 637 is optional, although when present, the valve protector member 637 protects the valve member 612 from damage and can maintain the shape of the flow control device 110 against compression and constriction to a certain extent. The valve protection member 637 can also support and stiffen the flanges 620. The valve protector member 637 can be manufactured of a rigid, biocompatible material, such as, for example, nickel titanium, steel, plastic resin, and the like. In one embodiment, the valve protector member 637 has two or more windows 639 comprising holes that extend through the valve protector member, as shown in FIG. 6B. The windows 639 can provide a location where a removal device, such as graspers or forceps, can be inserted in order to facilitate removal of the flow control device 110 from a bronchial passageway.

The valve protector member 637 can be formed out of a solid tube of a super-elastic material such as Nitinol. In one embodiment, the valve protector member 637 is compressible to a smaller diameter for loading into a delivery catheter. The compressibility can be achieved by forming the valve protector member 637 out of a series of struts or by including some open spaces in the valve protector member 637. The super-elastic characteristics of Nitinol would allow the valve protector member 637 to be compressed during deployment, yet still allow it to expand once deployed.

The seal 615 and/or the frame 625 can contract or expand in size, particularly in a radial direction. The default state is an expanded size, such that the flow control device 110 will have a maximum diameter (which is defined by either the seal 615 or the frame 625) when the flow control device 110 is in the default state. The flow control device 110 can be radially contracted in size during insertion into a bronchial passageway, so that once the flow control device 110 is inserted into the passageway, it expands within the passageway.

In one embodiment, the valve member 612 and frame 625 are independently enlargeable and contractible. Alternately, the frame 625 can be enlargeable and contractible, while the valve member 612 is not enlargeable and contractible. The independent collapsibility of the valve member 612 and frame 625 facilitate deployment and operation of the flow control device 110. The flow control device 110 can be compressed from a default, enlarged state and implanted in a desired location within a bronchial passageway. Once implanted, the flow control device 110 automatically re-expands to anchor within the location of the bronchial passageway. The independent compression of the frame and valve member reduces the likelihood of damage to the flow control device 110 during deployment. Furthermore, the valve can be substantially immune to the effects of compression of the frame 625. In one embodiment, the diameter of the frame 625 may collapse as much as 80% without affecting the valve member 612 so that the valve member 612 will still operate normally. The flow control device 110 does not have to be precisely sized for the lumen it is to be placed within. This affords medical providers with the option of buying smaller volumes of the flow control device 110 and being able to provide the same level and scope of coverage for all patients.

The dimensions of the flow control device 110 can vary based upon the bronchial passageway in which the flow control device 110 is configured to be implanted. As mentioned, the valve member does not have to be precisely sized for the bronchial passageway it is to be placed within. Generally, the diameter D (shown in FIG. 6A) of the flow control device 110 in the uncompressed state is larger than the inner diameter of the bronchial passageway in which the flow control device 110 will be placed. This will permit the flow control device 110 to be compressed prior to insertion in the bronchial passageway and then expand upon insertion in the bronchial passageway, which will provide for a secure fit between the flow control device 110 and the bronchial passageway.

Figure 8:
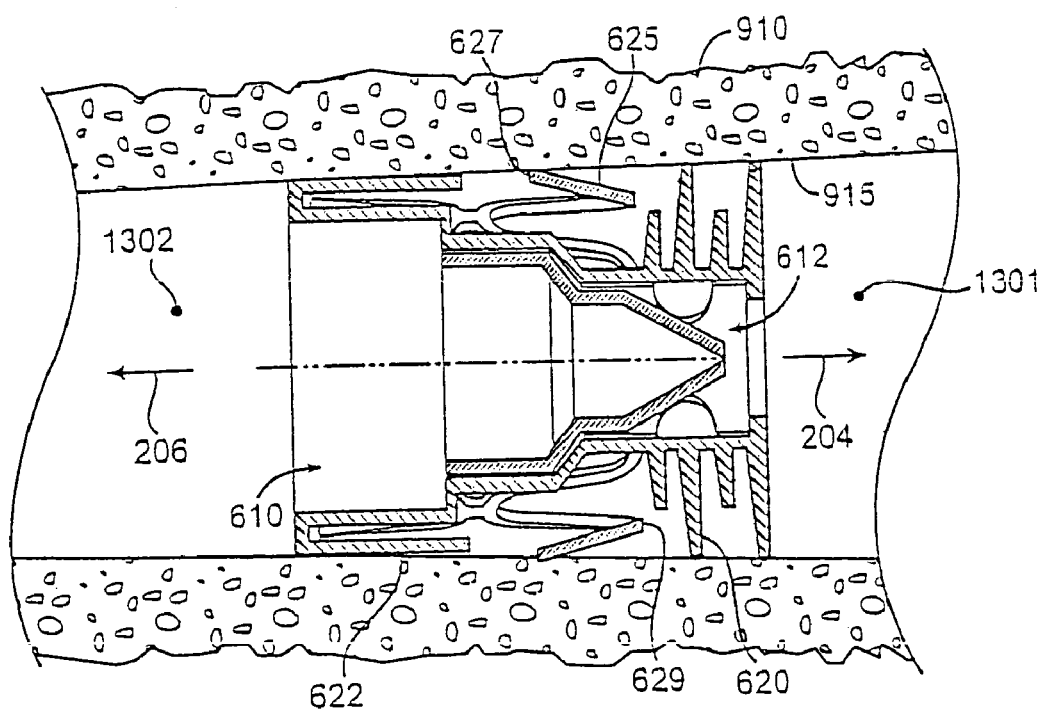
FIG. 8 shows the flow control device of FIGS. 5–6 implanted in a bronchial passageway.

FIG. 8 shows the flow control device 110 of FIGS. 5–6 implanted within a bronchial passageway 910 having interior walls 915 that define a lumen of the bronchial passageway 910. As is known to those skilled in the art, fluids (such as air) can travel to a region of the lung through the lumen of the bronchial passageway 910.

As shown in FIG. 8, the flow control device 110 is implanted such that one or more of the flanges 620 contact the interior walls 915 to provide a seal that prevents fluid from flowing between the interior walls 915 and the flanges 620. The cuff 622 can also provide a seal with the bronchial passageway. At least a portion of the outermost surface of the cuff 622 sealingly engages the surface of the interior walls 915. Thus, the flanges 620 and the cuff 622 both provide a seal between the interior walls 915 of the bronchial passageway 910 and the flow control device 110.

Thus, fluid must flow through the interior lumen 610 of the flow control device 110 in order to flow from a proximal side 1301 of the flow control device 110 to a distal side 1302 or vice-versa. That is, the flanges 620 and cuff 620 form a seal with the interior wall 915 to prevent fluid from flowing around the periphery of the flow control device 110, thereby forcing fluid flow to occur through the internal lumen of the flow control device 110, and specifically through the valve member 612.

As shown in FIG. 8, the valve member 612 is oriented such that it will permit regulated fluid flow in the proximal direction 204, but prevent fluid in a distal direction 206 through the flow control device 110. The valve member 612 will only permit fluid flow therethrough when the fluid reaches a predetermined cracking pressure, as described below. Other types of valve members, or additional valve members, could be used to permit fluid flow in both directions or to prevent fluid flow in either direction.

As shown in FIG. 8, the frame 625 grips the interior wall 915 and presses against the wall 915 with a pressure sufficient to retain the flow control device 110 in a fixed position relative to the bronchial passageway. The prongs 627 are positioned such that they lodge against the interior walls 915 and prevent the flow control device 110 from migrating in a distal direction 206. The curved, proximal ends 629 of the frame 625 can lodge against the interior walls 915 and prevent migration of the flow control device 110 in a proximal direction 204.

When the flow control device 110 is properly implanted, the frame 625 does not necessarily return to its original expanded state after being implanted, but may be deformed and inserted such that one side is collapsed, or deformed relative to its pre-insertion shape. The frame 625 preferably has sufficient outward radial force to maintain the flow control device's position in the bronchial passageway. Due to the substantially independent deformation of the frame 625, even if the frame 625 is implanted in a deformed state, the seal member 615 can still maintain a true and complete contact with the walls of the bronchial passageway.

The frame 625 expands to grip the bronchial wall when the flow control device 110 is implanted in the bronchial passageway. Thus, the frame 625 can be in at least two states, including an insertion (compressed) state and an anchoring (expanded or uncompressed) state. In the insertion state, the frame 625 has a smaller diameter than in the anchoring state. Various mechanisms can be employed to achieve the two states. In one embodiment, the frame 625 is manufactured of a malleable material. The frame 625 can be manually expanded to the anchoring state, such as by inserting an inflatable balloon inside the frame once the flow control device 110 is implanted in the bronchial passageway, and then inflating the balloon to expand the frame beyond the material's yield point into an interfering engagement with the wall of the bronchial passageway.

Another mechanism that can be employed to achieve the two-state frame 625 size is spring resilience. The insertion state can be achieved through a preconstraint of the frame 625 within the elastic range of the frame material. Once positioned in the bronchial passageway, the frame 625 can be released to expand into an anchoring state. Constraining tubes or pull wires may achieve the initial insertion state.

Another mechanism that can be used to achieve both the insertion and the anchor states of the frame 625 is the heat recovery of materials available with alloys, such as certain nickel titanium alloys, including Nitinol. The transition temperature of the frame 625 could be below body temperature. Under such a circumstance, a cool frame 625 can be positioned and allowed to attain ambient temperature. The unrecovered state of the frame 625 would be in an insertion position with the frame 625 having a smaller diameter. Upon recovery of the frame material, the frame 625 would expand, such as when the frame achieves a temperature within the bronchial passageway. Another use of this material may be through a heating of the device above body temperature with a recovery temperature zone above that of normal body temperature but below a temperature which may cause burning. The device might be heated electrically or through the modulation of a field.

In one embodiment, the outer diameter of the seal member 615 of the flow control device 110 (in an uncompressed state) is in the range of approximately 0.20 inches to 0.42 inches at the flanges 620 or at the cuff 622. In one embodiment, the frame 625 has an outer diameter (in an uncompressed state) in the range of approximately 0.24 to 0.48 inches. In one embodiment, the flow control device 110 has an overall length from the proximal end 602 to the distal end 604 of approximately 0.35 inches to 0.52 inches. It should be appreciated that the aforementioned dimensions are merely exemplary and that the dimensions of the flow control device 110 can vary based upon the bronchial passageway in which it will be implanted.

Figure 9:
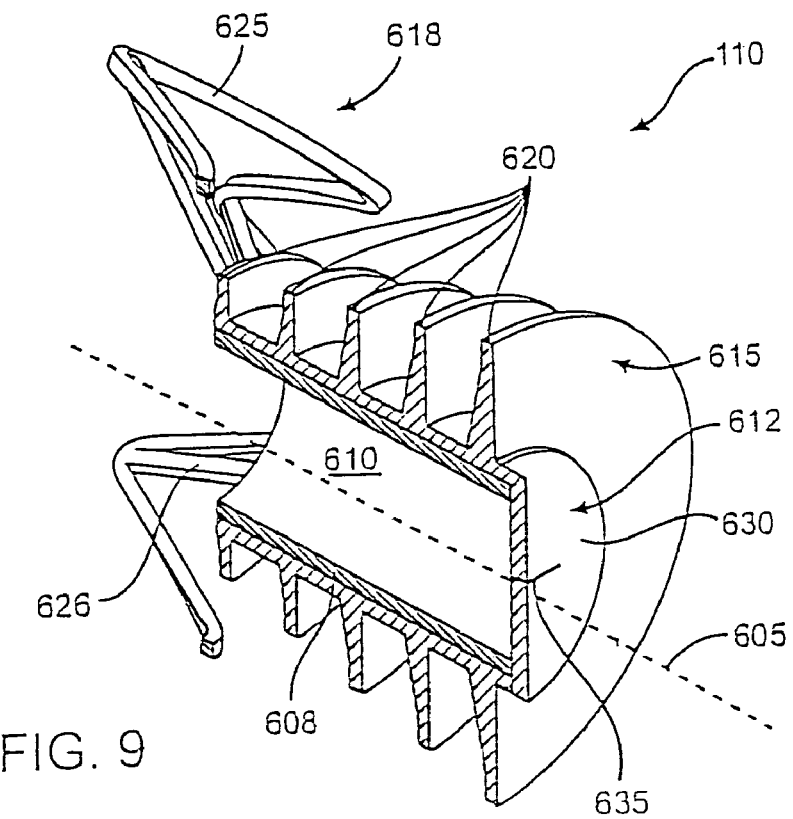
FIG. 9 shows a perspective, cross-sectional view of another embodiment of the flow control device.

FIGS. 9–11 show another embodiment of the flow control device 110. FIG. 9 shows a perspective, cross-sectional view, FIG. 10 shows a side, cross-sectional view, and FIG. 11 shows a front, plan view of the other embodiment of the flow control device 110. Unless noted otherwise, like reference numerals and like names refer to like parts as the previous embodiment. This embodiment of the flow control device has an anchor member 618 comprising a frame 625 that is disposed in a spaced relationship from the rest of the flow control device 110. That is, the frame 625 is distally-spaced from the seal member 615 and the internal lumen 610. As in the previous embodiment, the flow control device 110 extends generally along a central axis 605 (shown in FIGS. 9 and 10) and has a main body that defines an interior lumen 610 through which fluid can flow along a flow path that generally conforms to the central axis 605. The interior lumen 610 is surrounded by an annular wall 608. The flow of fluid through the interior lumen is controlled by a valve member 612. FIG. 9 shows the valve member 612 located at an end of the interior lumen 610, although it should be appreciated that the valve member 612 could be positioned at various locations along the interior lumen 610.

As best shown in FIG. 11, the flow control device 110 has a generally circular shape (when viewed longitudinally) that will facilitate insertion of the flow control device into a bronchial passageway, although it should be appreciated that the flow control device 110 can have other cross-sectional shapes that enable the device to be inserted into a bronchial passageway.

As best shown in FIGS. 9 and 10, the seal member 615 is located on an outer periphery of the flow control device 110. In the embodiment shown in FIGS. 9–11, the seal member includes a series of radially-extending, circular flanges 620 that surround the entire outer circumference of the flow control device 110.

With reference to FIGS. 9 and 10, the anchor member 618 is shown located on a distal end of the flow control device 110, although the anchor member 618 can be located at various locations along the flow control device 110. In the embodiment shown in FIGS. 9–11, the frame 625 is attached to the flow control device 110 by one or more attachment struts 626 although the frame 625 could also be attached in other manners.

In the embodiment shown in FIGS. 9–11, the valve member 612 comprises a septum 630 located at a proximal end of the interior lumen 610. In a default state, the septum 630 occludes fluid from flowing through the interior lumen 610 so that the flow control device 110 shown in FIGS. 9–11 can function as an occluder that prevents flow in either direction. However, the septum 630 can be pierced by a dilator device (described below) via a slit 635 in the septum 630, in order to permit fluid to flow through the interior lumen 610. The septum 630 is made from a deformable elastic material.

The dilator device could comprise a wide variety of devices that function to dilate the slit 635 in the septum 630 and thereby provide a passageway across the flow device 110 through which fluid can flow in one or two directions, depending on the design of the dilator device. The dilator devices could comprise, for example:

(1) A suction catheter for aspirating air or fluid distal to the flow control device.
(2) A long, thin suction catheter that could be snaked into very distal portions of the isolated lung region for aspirating fluid or air in the distal portions of the isolated lung regions.
(3) A short tube to allow free fluid communication between the occluded region of a bronchial passageway distal of an implanted flow control device and the region of the bronchial passageway proximal of the implanted flow control device.
(4) A tube or other short structure with a one-way valve mounted inside to allow fluid to be expelled from the isolated distal lung region (either during normal exhalation or during a procedure that forces fluid from the isolated, distal lung region) and to prevent fluid from entering the isolated lung region.
(5) A catheter with a one-way valve mounted at the tip to allow fluid to be expelled from the isolated, distal lung region (either during normal exhalation or during a procedure that forces fluid from the distal lung segment) and to prevent fluid from entering the lung segment.
(6) A catheter for instilling a therapeutic agent, such as antibiotics or other medication, into the region of the bronchial passageway or lung distal to the flow control device that has been implanted in the bronchial passageway.
(7) A catheter for passing brachytherapy sources into the bronchial passageway distal to the implanted flow control device for therapeutic reasons, such as to stop mucus production, kill a pneumonia infection, etc. The brachytherapy source can be configured to emit either Gamma or Beta radiation.
(8) A catheter with a semi-permeable distal aspect that circulates a nitrogen-solvent fluid, which absorbs through osmosis nitrogen trapped in the lung region distal to the flow control device.

Thus, the dilator devices described above generally fall into two categories, including catheter-type dilation devices and dilation devices comprised of short, tube-like structures. However, it should be appreciated that flow control device 110 can be used with various dilation devices that are not limited to those mentioned above.

Figure 12:
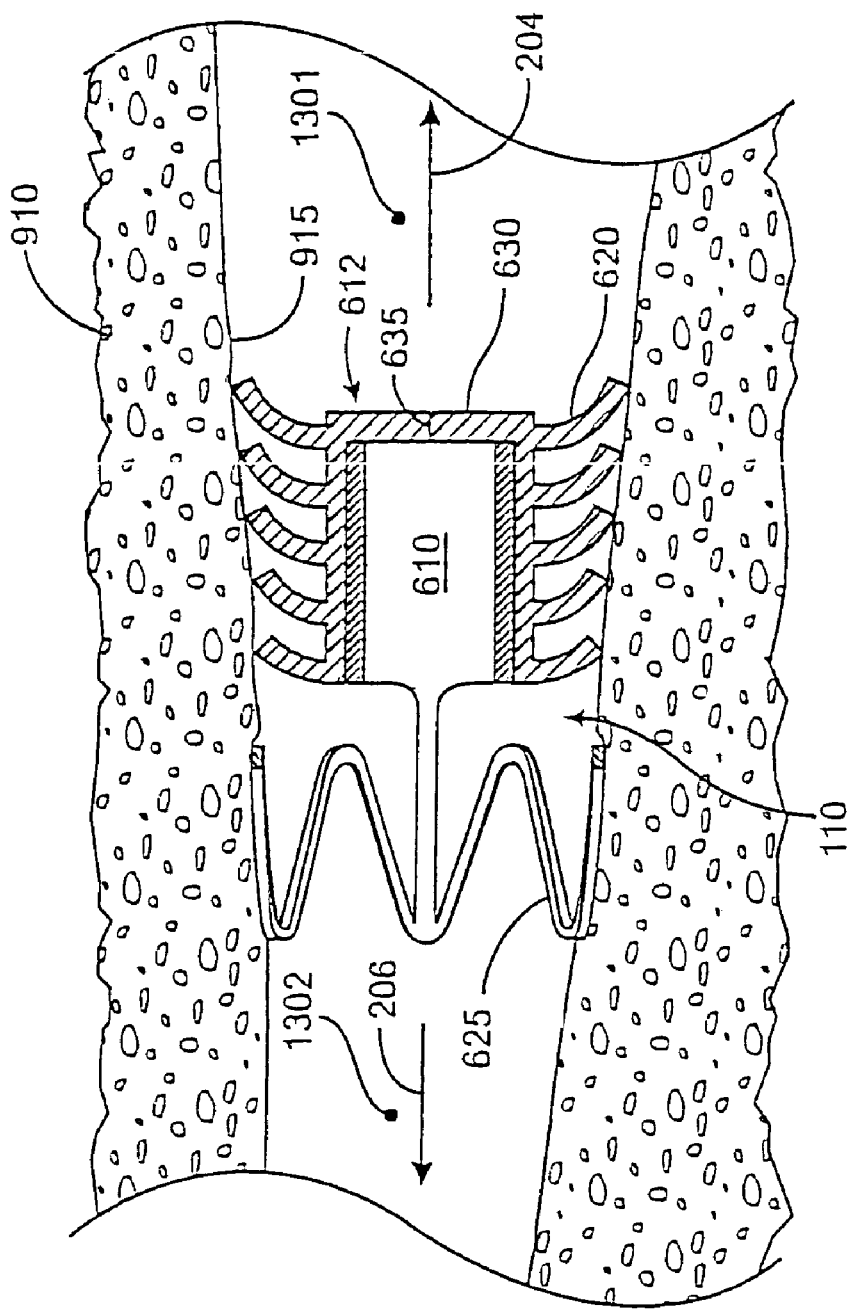
FIG. 12 shows the flow control device of FIG. 9 implanted in a bronchial passageway.
Figure 13:
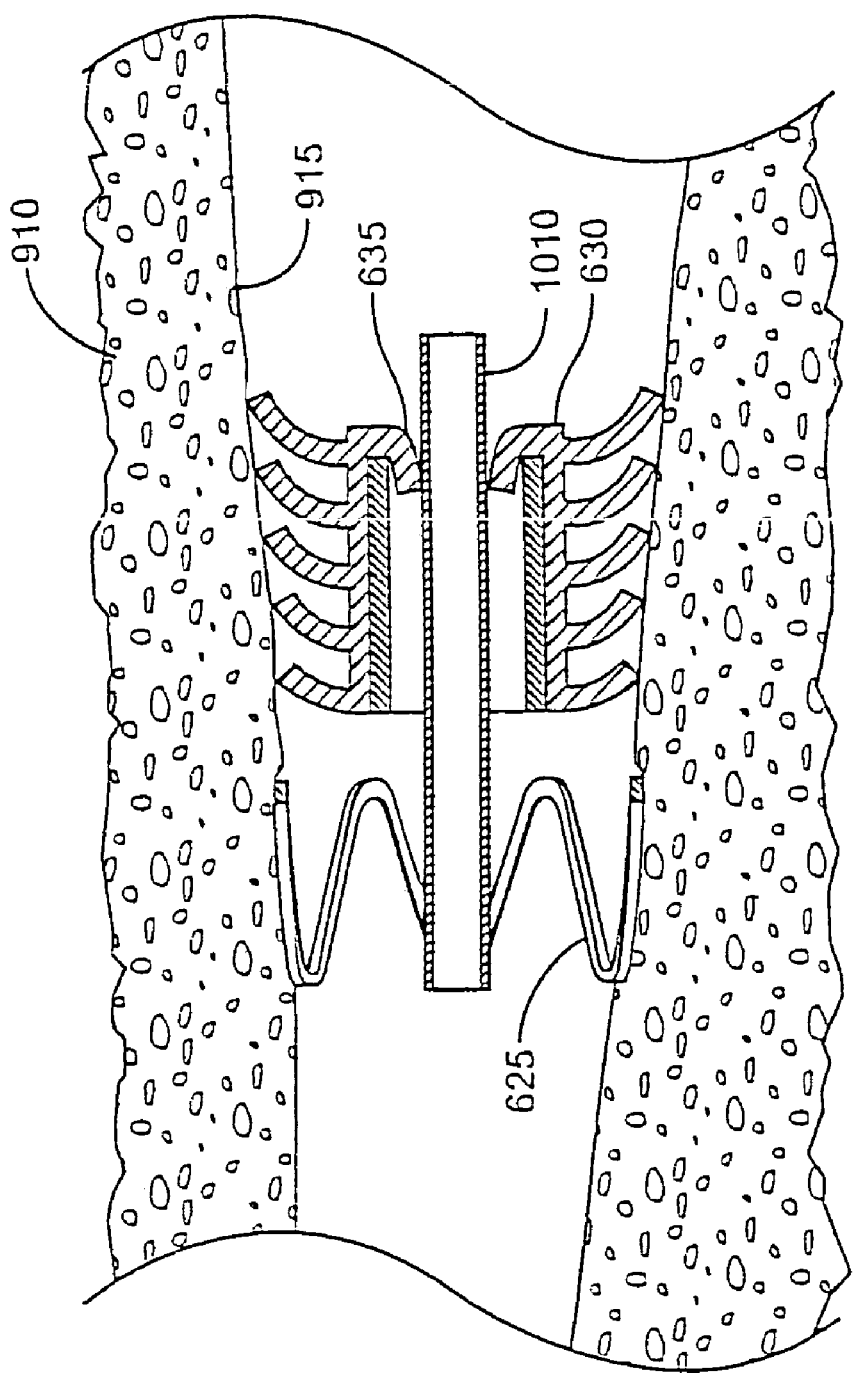
FIG. 13 shows the flow control device of FIG. 9 implanted in a bronchial passageway and dilated by a dilation device comprised of a tube.

The deployment of the flow control device 110 and use of a dilator device therewith is described in more detail with reference to FIGS. 12 and 13. The use of a dilator device is described in the context of being used with one of the flow control device 110 described herein, although it should be appreciated that the dilator device can be used with other types of flow control devices and is not limited to being used with those described herein. FIGS. 12 and 13 show the flow control device 110 of FIGS. 9–11 implanted within a bronchial passageway 910 having interior walls 915 that define a lumen of the bronchial passageway 910.

As shown in FIG. 12, the flow control device 110 is implanted such that one or more of the flanges 620 contact the interior walls 915 to provide a seal that prevents fluid from flowing between the interior walls 915 and the flanges 620. Thus, fluid must flow through the interior lumen 610 of the flow control device 110 in order to flow from a proximal side 1301 of the flow control device 110 to a distal side 1302 or vice-versa.

It should be appreciated that the relative locations of the flanges 620 and the frame 625 along the longitudinal axis of the flow control device can be changed. For example, the flanges 620 could be located on the distal side of the flow control device 110 rather than on the proximal side, and the frame 625 can be located on the proximal side rather than the distal side. The flow control device 110 could also be positioned in a reverse orientation in the bronchial passageway than that shown in FIG. 12. In such a case, the orientation of the valve member 612 could be arranged to permit flow in a desired direction, such as in a proximal direction 204 (to allow air flow out of a lung region), a distal direction 206 (to allow air flow into a lung region), or in both directions. The orientation of the flanges 620 can also be changed based upon how the flow control device 110 is to be implanted in the bronchial passageway.

As discussed, the frame 625 grips the interior wall 915 and presses against the wall 915 with a pressure sufficient to retain the flow control device 110 in a fixed position. When in the state shown in FIG. 12, the flow control device 110 obstructs the bronchial passageway 910 to prevent fluid from flowing in either direction through the bronchial passageway 910. In this regard, the septum 630 can be sufficiently rigid so that the slit 635 does not open when subjected to expiration and inhalation pressures. As described further below, other embodiments of the flow control device 110 can be used to provide regulated fluid flow through the bronchial passageway 910 in a distal direction, a proximal direction, or in both the distal and proximal directions.

With reference now to FIG. 13, the septum 630 can be mechanically pierced through the slit 635, such as by using a dilator device comprised of a tube 1010 that dilates the slit 635. Alternately, the septum 630 can have no slit 635 and the tube 1010 can be used to pierce through the septum 630. In either case, the septum 630 preferably seals around the outer surface of the tube 1010 in order to prevent fluid flow in the space between the septum 630 and the tube 1010. The tube 1010 is hollow and has an internal lumen such that the tube 1010 provides an unobstructed fluid flow passageway between a region of the bronchial passageway 910 distal of the flow control device 110 and a region of the bronchial passageway proximal of the flow control device 110.

Various dilator devices can be inserted through the flow control device 110 to provide various flow characteristics to the flow control device, as well as to provide access to the region of the bronchial passageway located distal of the flow control device 110. In any of the embodiments of the dilation devices and flow control devices described herein, it should be appreciated that the dilation device can be pre-loaded into the flow control device 110 prior to deploying the flow control device 110 to the bronchial passageway. Alternately, the flow control device 110 can be implanted into the bronchial passageway without the dilation device and the dilation device inserted into the flow control device 110 after implant of the flow control device 110.

Figure 14:
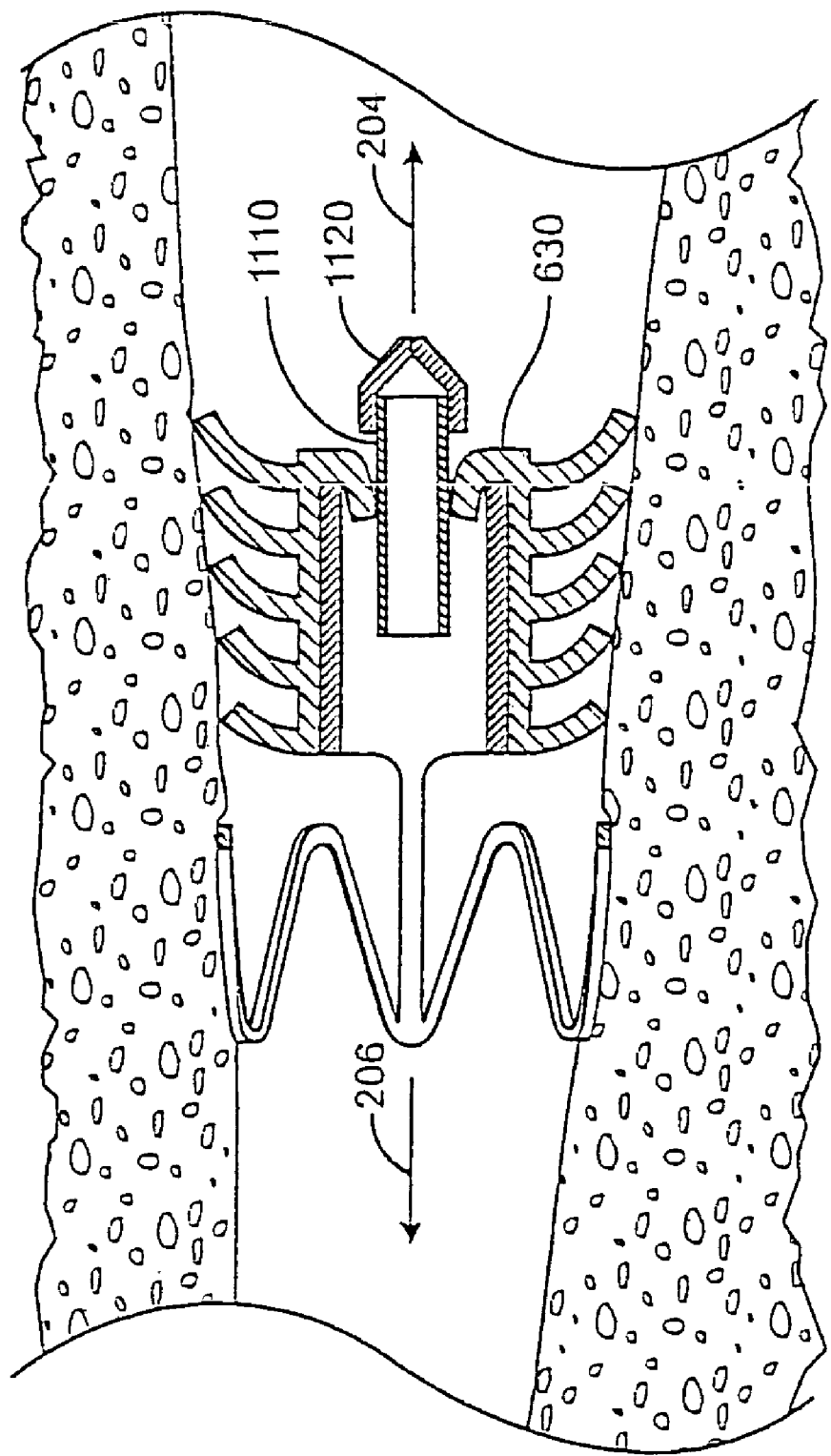
FIG. 14 shows the flow control device of FIG. 9 implanted in a bronchial passageway and dilated by a dilation device comprised of a tube with a one-way valve.

FIG. 14 shows another embodiment wherein the dilator device comprises a tube section 1110 that includes a one-way valve 1120 mounted thereon. The one-way valve 1120 can be any type of valve that permits fluid flow in a first direction but prevents fluid flow in a second direction opposite to the first direction. For example, as shown in FIG. 14, the one-way valve 1120 can comprise a duckbill valve of the type known to those skilled in the art. The one-way valve 1120 can be positioned such that it allows fluid flow in an exhalation direction (i.e., proximal direction) 204 but prohibits fluid flow in an inhalation direction (i.e., distal direction) 206.

Figure 15:
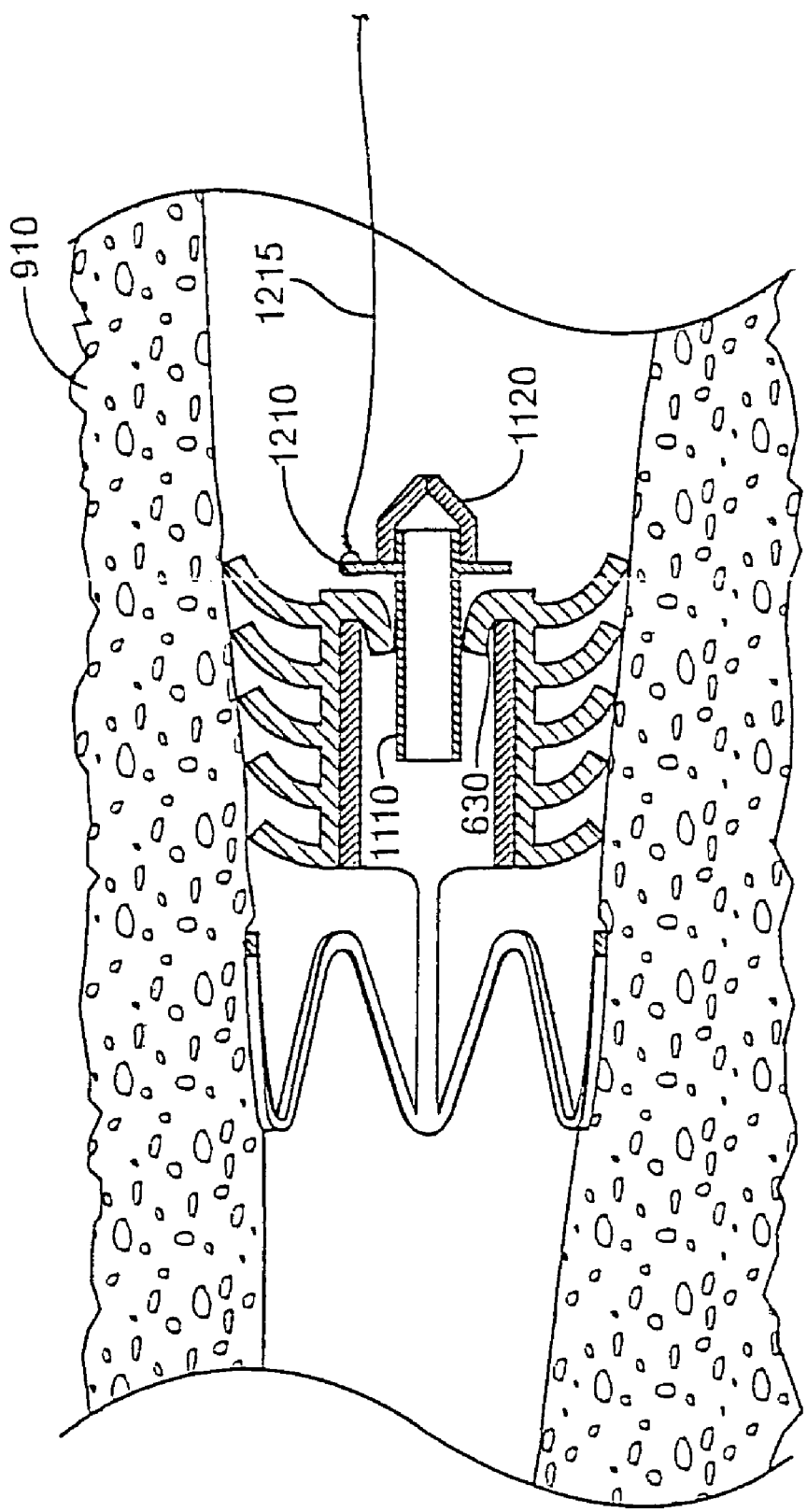
FIG. 15 shows the flow control device of FIG. 9 implanted in a bronchial passageway and dilated by a dilation device comprised of a tube with a one way valve, wherein the tube is attached to a removal tether.

FIG. 15 shows the flow control device 110 with the septum 630 dilated by a tube section 1110 that includes a one-way valve 1120 mounted thereon. The tube section 1110 has an attachment structure, such as a flange 1210. A remote actuator, such as a tether 1215, is attached at a proximal end to the attachment structure 1210 of the tube section 1110. The tether 1215 can be formed of a variety of bio-compatible materials, such as any well-known suture material. The tether 1215 extends in a proximal direction through the bronchial passageway 910 and through the trachea (shown in FIG. 2) so that a proximal end of the tether 1215 protrudes through the mouth or nose of the patient. The tether can be pulled outwardly, which will also cause the attached tube structure 1110 to be pulled outwardly from the septum 630 by virtue of the tether's attachment to the tube attachment structure 1210. The absence of the tube structure 110 would then cause the septum 630 to re-seal so that the flow control device 110 again occludes fluid flow through the bronchial lumen 910.

Figure 16:
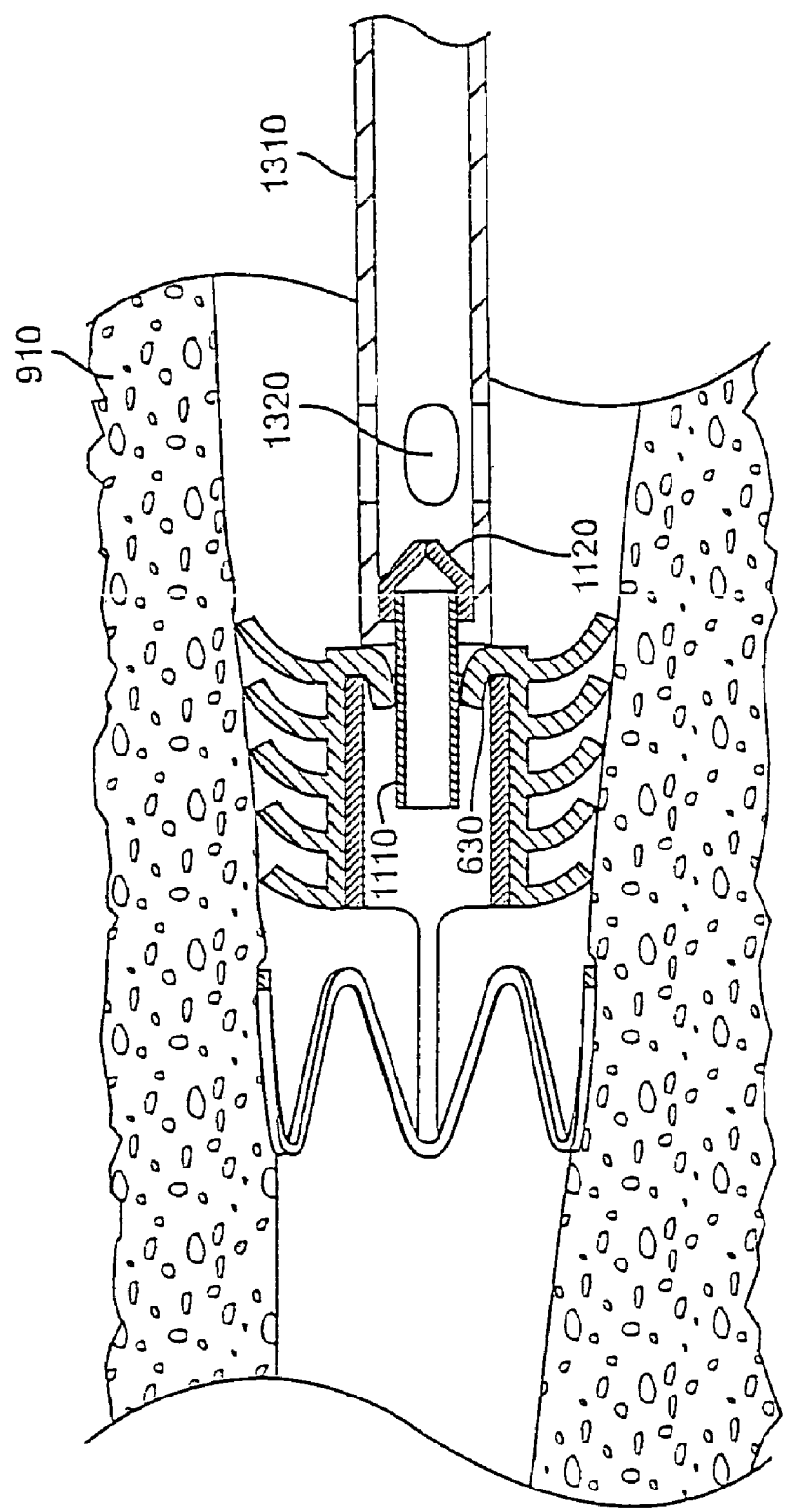
FIG. 16 shows the flow control device of FIG. 9 implanted in a bronchial passageway and dilated by a dilation device comprised of a tube, which is fluidly coupled to a catheter.

FIG. 16 shows the flow control device 110 implanted in the bronchial lumen 910, with the septum 630 dilated by a tube section 1110 that includes a one-way valve 1120 mounted thereon. The one-way valve 1120 fluidly communicates with the internal lumen of a catheter 1310 at a distal end of the catheter 1310. The catheter 1310 extends in a proximal direction through the bronchial passageway 910 and through the trachea (shown in FIG. 2) so that a proximal end of the catheter 1310 protrudes through the mouth or nose of the patient. The catheter 1310 thereby provides an airflow passageway for fluid flowing through the one-way valve 1120. Thus, the catheter 1310 in combination with the one-way valve 1120 and the flow control device 110 provide a regulated fluid access to the bronchial passageway 910 at a location distal of the flow control device 110. The catheter 1310 can thus be used to aspirate fluid from a location distal of the flow control device 110 by applying a suction to the proximal end of the catheter 1310, which suction is transferred to the distal region of the bronchial passageway through the internal lumen of the catheter 1310, the tube section 1110, and the flow control device 110. The catheter optionally has one or more vent holes 1320 at a location proximal of the one-way valve 1120. The vent holes 1320 permit fluid to flow from the internal lumen of the catheter 1310 into the bronchial passageway proximal of the flow control device 110.

Figure 17:
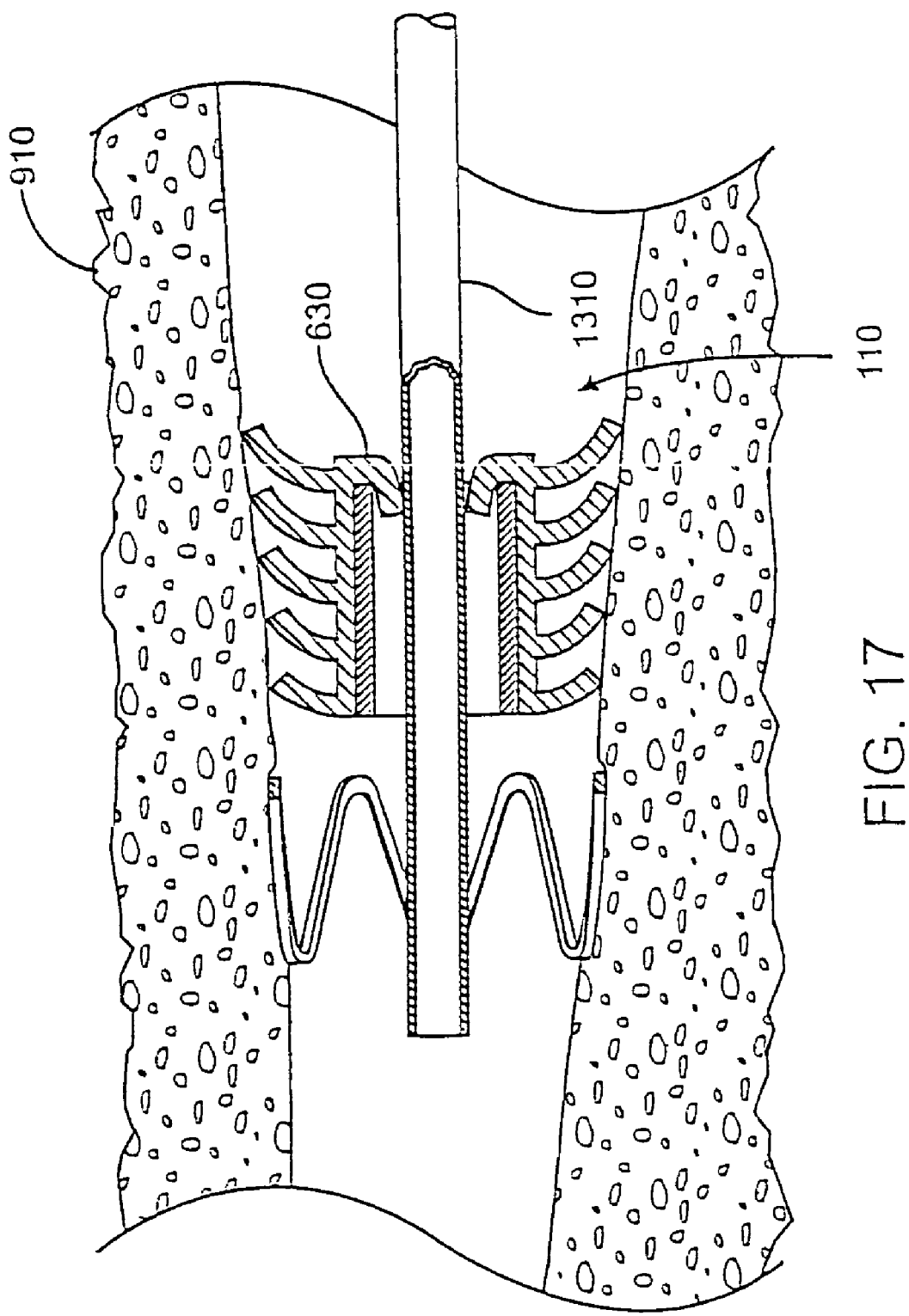
FIG. 17 shows the flow control device of FIG. 9 implanted in a bronchial passageway and dilated by a dilation device comprised of a catheter.

FIG. 17 shows the flow control device 110 mounted within the bronchial passageway 910, with the slit of the septum 630 dilated by a catheter 1310. A distal end of the catheter 1310 is located distally of the septum 630. The catheter 1310 extends in a proximal direction through the bronchial passageway 910 and through the trachea (shown in FIG. 2) so that a proximal end of the catheter 1310 protrudes through the mouth or nose of the patient. The catheter 1310 provides an airflow passageway across the flow control device 110. Thus, the catheter 1310 provides unobstructed fluid access to the bronchial passageway 910 at a location distal of the flow control device 110. The catheter 1310 can thus be used to aspirate fluid from a location distal of the flow control device 110 by applying a suction to the proximal end of the catheter 1310, which suction is transferred to the distal region of the bronchial passageway through the internal lumen of the catheter 1310. The catheter 1310 also enables the instillation of therapeutic agents into the distal side of the flow control device, the passing of brachytherapy sources to the distal side of the flow control device, etc, all via the internal lumen of the catheter 1310.

Figure 18:
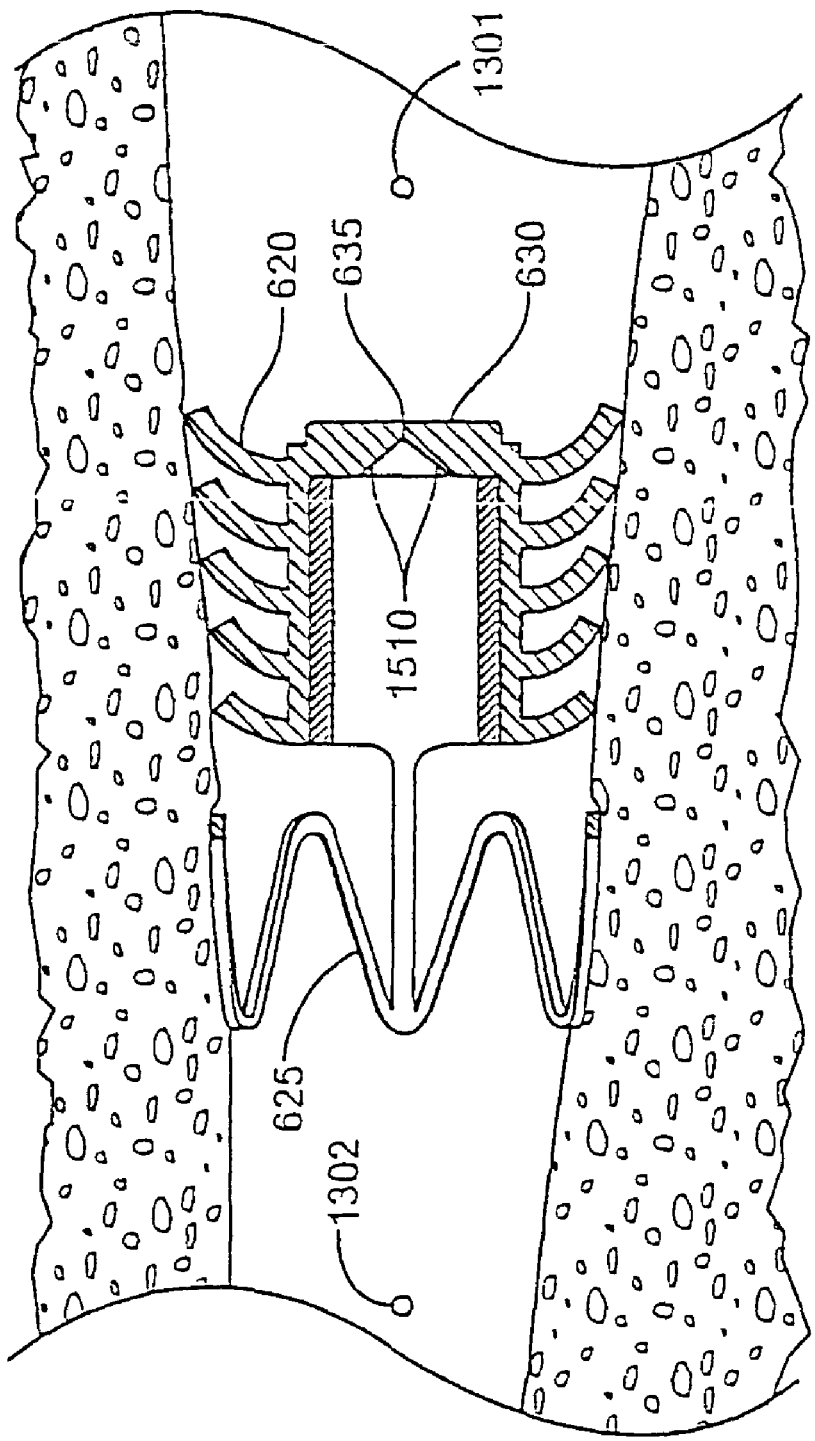
FIG. 18 shows another embodiment of a flow control device implanted in a bronchial passageway.

FIG. 18 shows an alternate embodiment of the flow control device 110 mounted in a bronchial passageway. This embodiment of the flow control device 110 is identical to that described above with reference to FIGS. 9–11, with the exception of the configuration of the septum 630 and the slit 635. A distal face of the septum has a taper 1510 located at the slit 635. The taper 1510 functions to reduce the cracking pressure required to open slit 635 so that the cracking pressure of the septum 630 will be lower for flow moving from the distal side 1302 toward the proximal side 1301 of the flow control device 110, and higher for flow from the proximal side 1301 to the distal side 1302. The cracking pressure can be made the same in both directions by eliminating the taper 1510. The cracking pressure can be varied by changing the durometer of the elastomer, by changing the diameter of the valve, by changing the length of the slit 635, by changing the angle, depth or shape of the taper feature 1510, or by changing the thickness of the valve feature.

Figure 19:
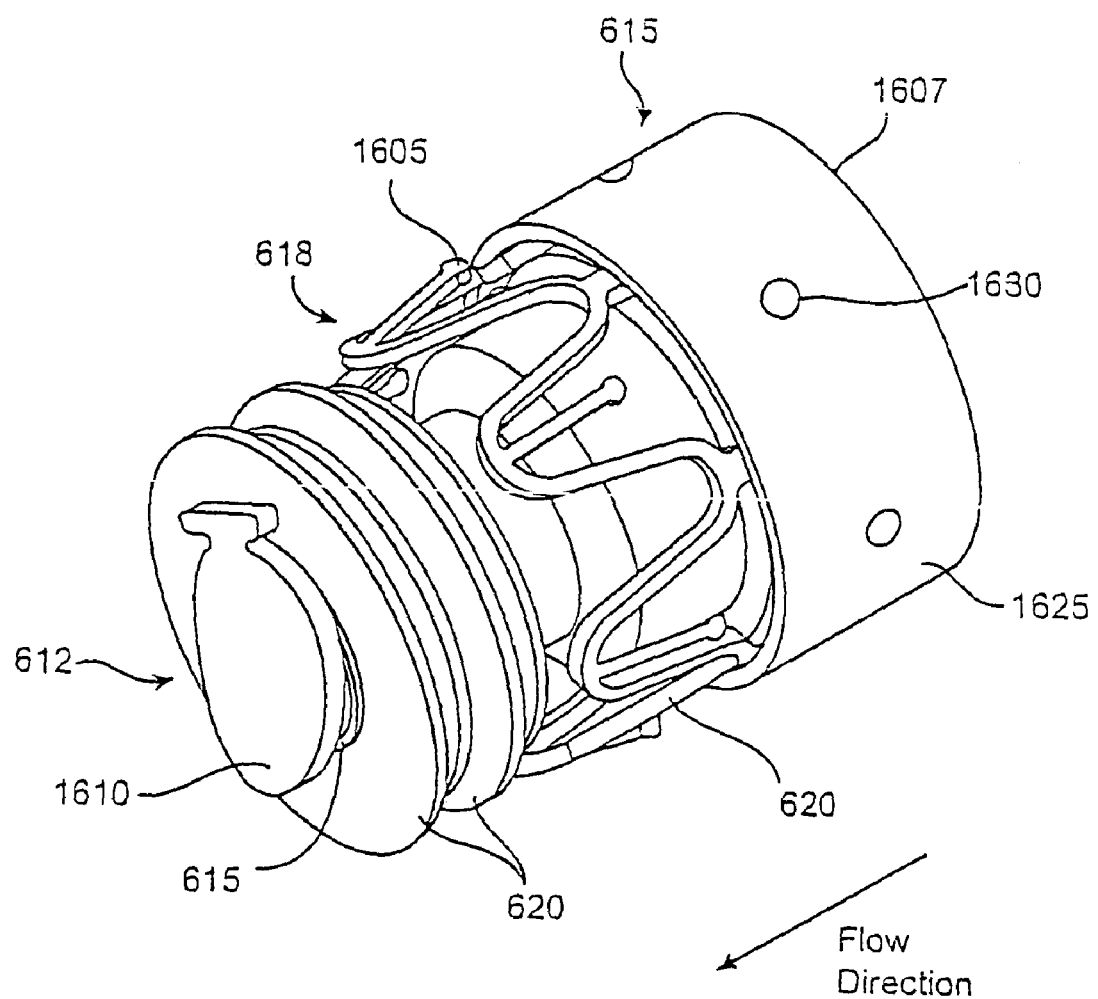
FIG. 19 shows a perspective view of another embodiment of a flow control device.
Figure 20:
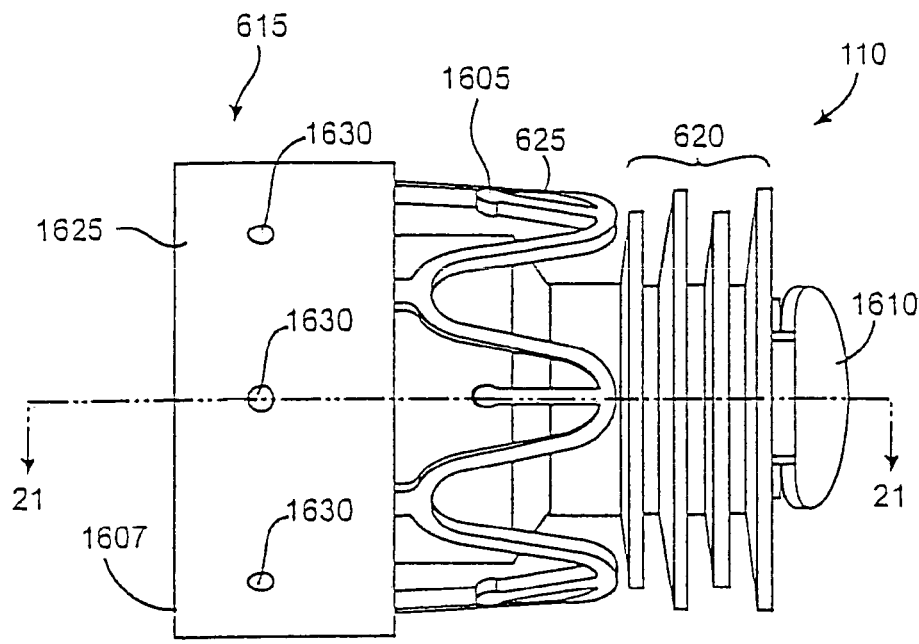
FIG. 20 shows a side view of the flow control device of FIG. 19.
Figure 21:
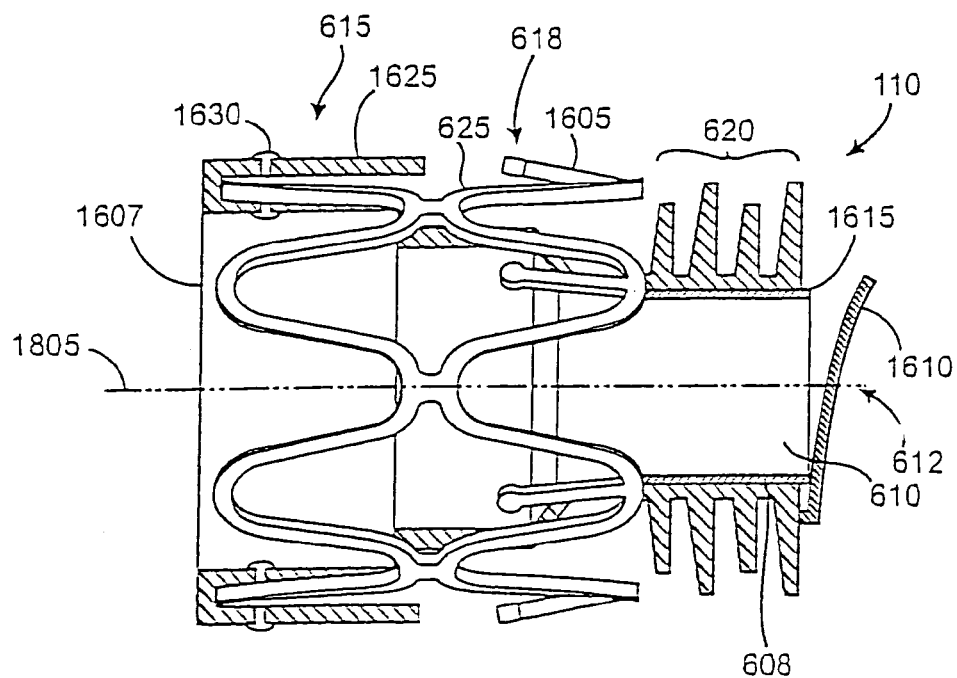
FIG. 21 shows a cross-sectional view of the flow control device of FIG. 20 cut along the line 21—21 of FIG. 20.

FIGS. 19–21 show another embodiment of the flow control device 110, which permits fluid flow in a first direction but prevents fluid flow in a second direction opposite the first direction. As in the previous embodiments, the flow control device 110 includes a seal member 615, a valve member 612, and an anchor member 618, as well as an interior lumen 610 formed by an annular wall 608 (shown in FIG. 21). The annular wall 608 can be made from Nitinol, injection molded plastic such as polyetheretherketone (PEEK), or other rigid biocompatible materials. As in the previous embodiments, the anchor member 618 comprises a frame 625 that is formed by a plurality of struts that define an interior envelope. The frame 625 can contract and expand in a radial and longitudinal direction (relative to the longitudinal axis 1805 shown in FIG. 21). The struts of the frame 625 are arranged so that one or more of the struts form prongs 1605 having edges that can wedge against the interior wall of a body passageway to secure an implanted flow control device against movement within the body passageway. The anchor member 618 can be manufactured of a shape-memory material, such as nickel titanium or Nitinol.

In the embodiment of the flow control device 110 shown in FIGS. 19–21, the valve member 612 comprises a one-way flap valve that permits fluid flow in a first flow direction. The flap valve includes a flap 1610, which can move between a closed position and an open position (the flap 1610 is shown in an open position in FIGS. 19–21). In the closed position, the flap 1610 sits within a seat to block fluid flow through the interior lumen 610. In the open position, the flap provides an opening into the interior lumen 610 so that fluid can flow through the interior lumen in the first flow direction.

As in the previous embodiment, the seal member 615 includes one or more flanges 620 that can seal against the interior wall of a body passageway in which the flow control device 110 is implanted. As shown in FIGS. 21, the flanges 625 of the seal member 615 surround the annular wall 608 that forms the interior lumen 610. The flap 1610 and the seal member 615 can be manufactured of an elastomeric material such as silicone, thermoplastic elastomer, urethane, etc. The flap 1610 can also be a rigid member that seals against an elastomer surface of the device 110, or it could be rigid and lined with an elastomer material. If a rigid flap is used, then hinges can be used to attach the flap to the device 110.

At a distal end 1607 of the flow control device 110, the seal member 615 folds over itself to form an annular cuff 1625. At least a portion of the frame 625 is positioned within the cuff and retained therein using retaining members, such as rivets 1630 that extend through holes in the cuff 1625. The rivets 1630 can be manufactured of a bio-compatible material, such as silicone adhesive. The rivets 1630 secure the cuff 1625 to the frame 625 so as to allow the frame 625 to expand and contract, but to still firmly capture the frame 625 to the cuff 1625. As best shown in the section view of FIG. 21, the rivets 1630 extend between opposed sides of the cuff 1625 to capture but not totally restrain the frame 625 against expansion or contraction. It should be appreciated that other attachment means can be used to attach the frame 625 to the cuff 1625. For example, adhesive can be used as in the previously-described embodiments.

Multiple rivets 1630 may be used in any variety of patterns around the circumference of the cuff 1625. While the rivets 1630 may be short in length such that there is little play between the folded over region of the cuff 1625 and the portion of the cuff 1625 located within the frame envelope, the rivets 1630 may be lengthened so that there is substantial play between the folded-over portion of the cuff 1625 and the interior region of the cuff 1625. In this manner, the frame 625 can be crumpled or deformed during deployment, while still allowing sufficient space for the folded-over region of the cuff 1625 to remain in contact with the lumen wall, helping to form a seal about the flow control device 110. Preferably, the frame envelope will conform to the lumen internal diameter where the flow control device 110 is implanted. However if there are gaps between the frame envelope and the lumen interior wall, then the cuff 1625 is capable of providing the fluid seal.

In one embodiment, the rivets are installed onto the flow control device 110 by first sliding the flow control device 110 over a dimpled mandrel. A hole is then drilled through the two walls of the cuff 1625, and the hole is filled with a glue, such as silicone adhesive, which will dry within the hole to form the rivets. The hole in the mandrel can have a dimpled shape that forms the inside rivet heads, while the outer heads can be formed by applying excessive adhesive on the outside. The assembly is then cured in an oven and slid off the mandrel.

In an alternative embodiment, the cuff 1625 may have a length such that the cuff 1625 folds over the entire length of the frame 625. The cuff 1625 is reattached to the proximal end of the polymer valve, such that the frame 625 is completely enclosed by the cuff 1625, so as the frame 625 is implanted within the bronchial passageway, the loose folds of the polymer skirt can provide a sealing feature.

Figure 22:
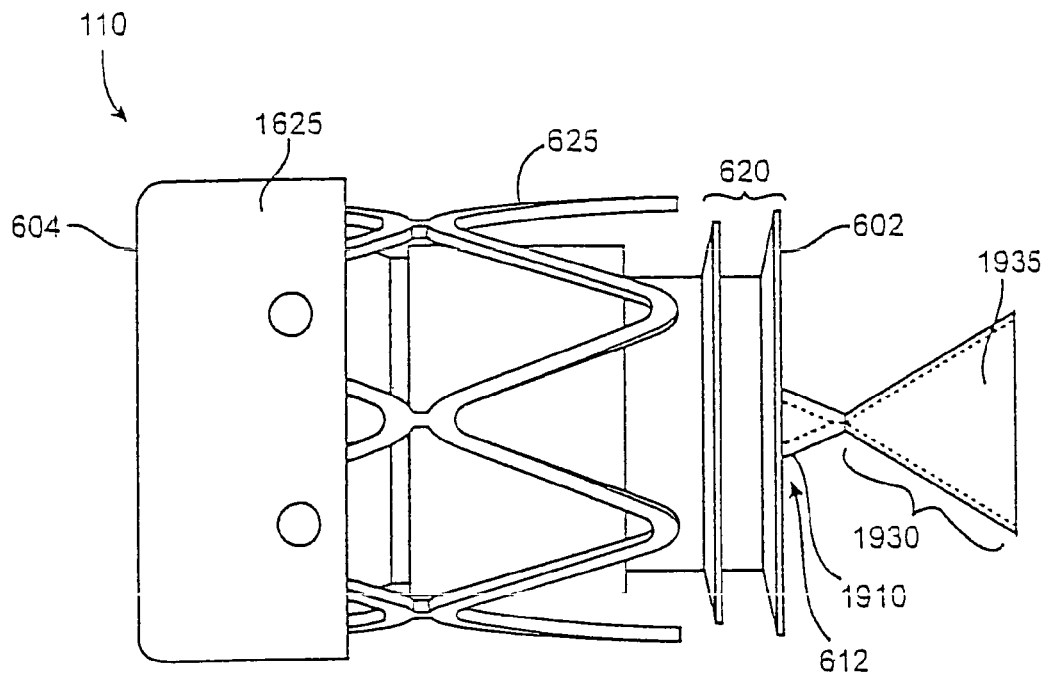
FIG. 22 shows another embodiment of a flow control device.
Figure 23:
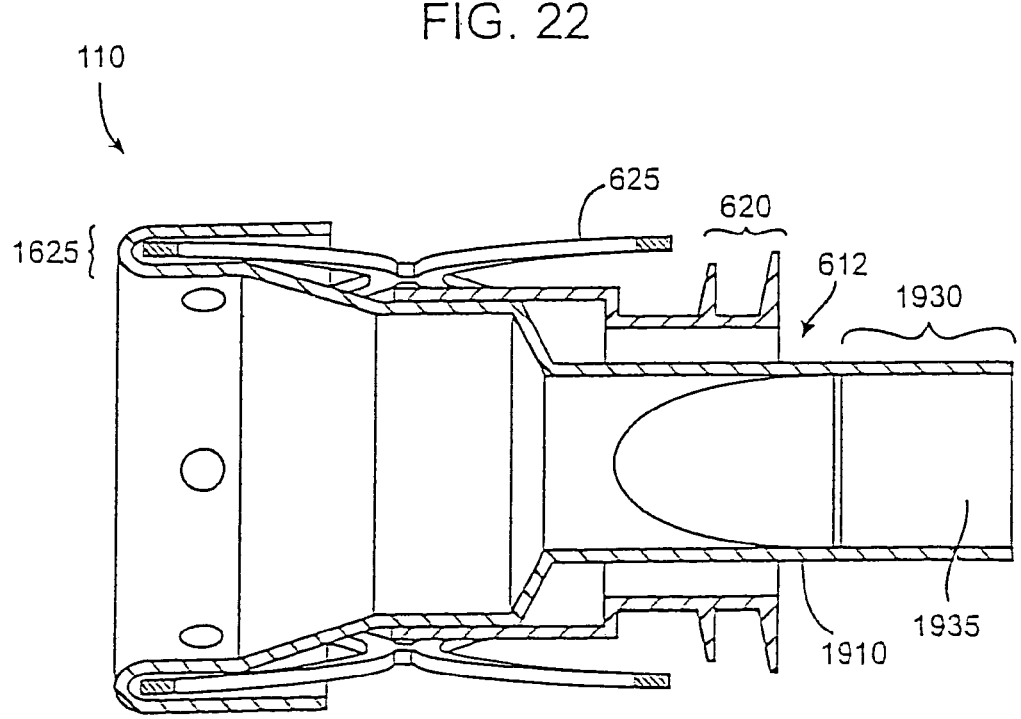
FIG. 23 shows a cross-sectional view of the flow control device of FIG. 22.
Figure 24:
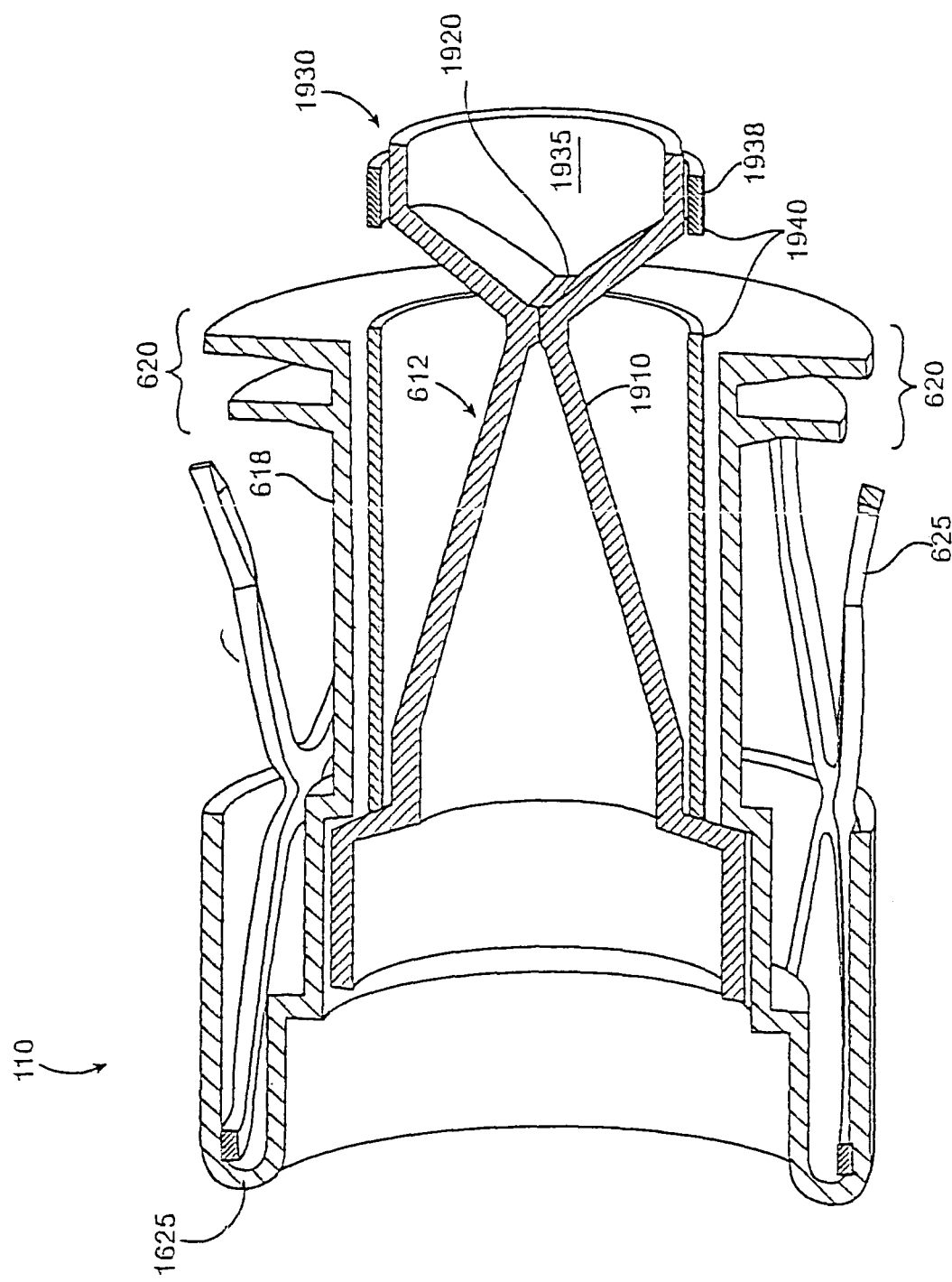
FIG. 24 shows a perspective view of another embodiment of a flow control device.

FIGS. 22–24 show yet another embodiment of a flow control device 110. The flow control device 110 shown in FIGS. 22–24 is structurally similar to the flow control device 110 described above with reference to FIGS. 19–21 in that it includes a seal member 615 with a cuff 1625 and flanges 620. The cuff 1625 retains an anchor member 618 comprised of a frame 625. The flow control device 110 of FIGS. 22–24 also includes a valve member 612 comprised of a one-way duckbill valve 1910. The duckbill valve 1910 is configured to prevent fluid flow from a proximal side to the distal side of the flow control device 110, and to allow flow at a controlled cracking pressure from the distal side to the proximal side through a slit 1920 (shown in FIG. 24) in the valve 1910. The cracking pressure of the duckbill valve 1910 can be adjusted by changing the thickness of the material used to manufactured the valve 1910, the durometer of the material, the angle of the duckbill valve, etc. The duckbill valve can be manufactured a deformable elastomer material, such as silicone.

As shown in FIGS. 22–24, the flow control device has valve dilation member 1930 that facilitates the passage of a dilation device (such as any of the dilation devices described above) through the flow control device 110. As was previously described, the presence of the dilation device in the flow control device 110 can allow the passage of fluid or other treatment devices to or from the isolated distal lung region when the flow control device 110 is implanted in a bronchial passageway. As best shown in FIGS. 22 and 24, the valve dilation member 1930 defines an interior region 1935 that has a cone shape having an apex that is adjacent to an apex of the duckbill valve 1910. The outer surfaces of the valve dilation member 1920 are not sealed from the surrounding environment, but are rather exposed. Thus, air pressure of the surrounding environment is equally distributed on all sides of the valve dilation member 1930 so that the dilation member 1930 will not open to fluid flow moving in a distal direction (such as during normal inspiration), but can be mechanically opened by a dilation device such as a catheter.

The flow control device 110 is shown in FIG. 24 with an optional feature comprised of a valve protector sleeve 1938 that at least partially surrounds the valve dilation member 1930. The valve protector sleeve 1938 can be attached to the seal member 615 and can made of a biocompatible materials such as stainless steel, Nitinol, etc. In order to ensure that the cracking pressure in the distal direction is not affected by the addition of the valve dilation member 1930, the protector sleeve 1938 preferably has one or more vent holes 1940, which ensure that the pressure is the same on interior and exterior surfaces of the valve dilation member 1930, as well as on the proximal surface of the duckbill valve 1910. In this way, the cracking pressure in the proximal direction is also unaffected.

Figure 25:
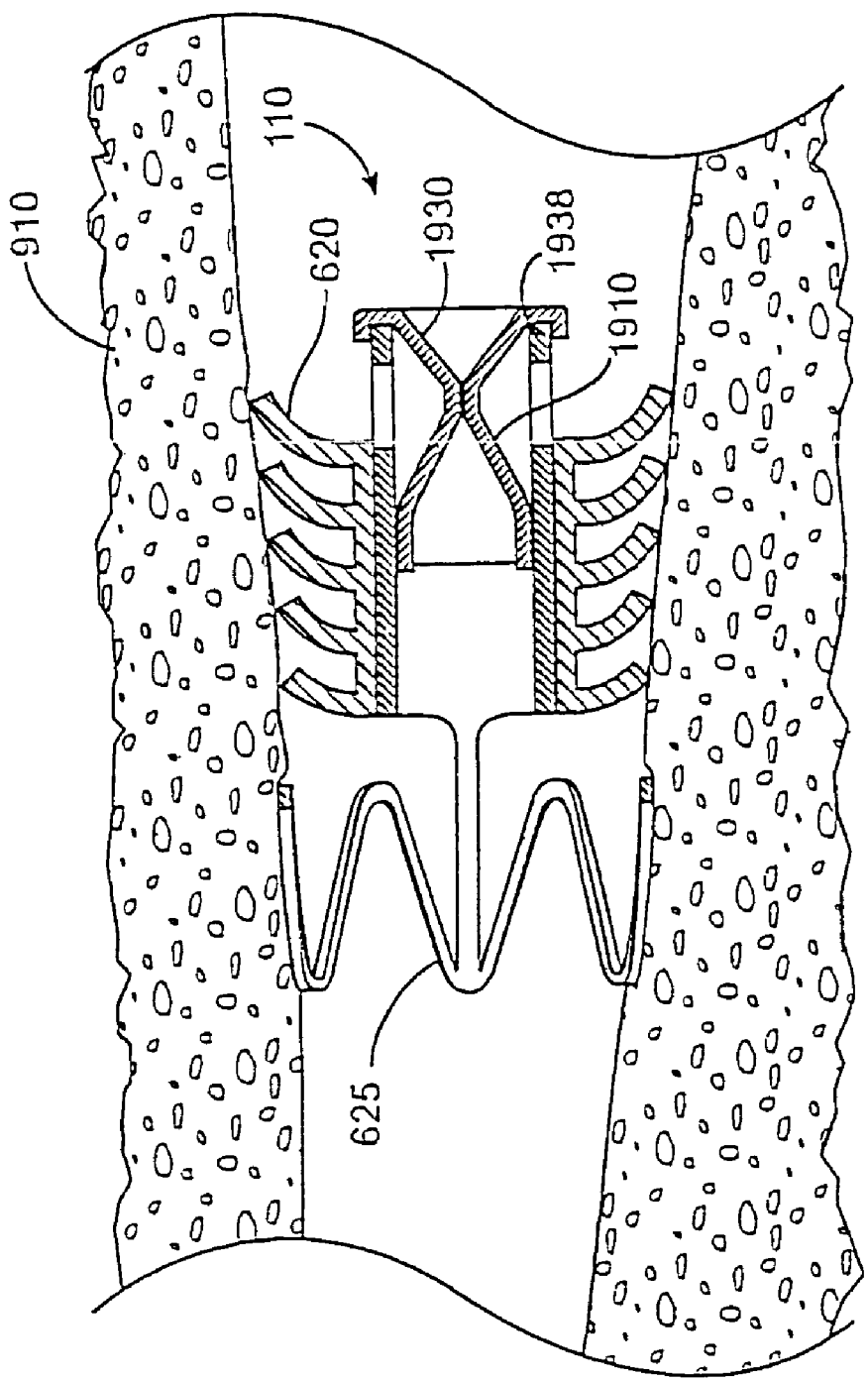
FIG. 25 shows another embodiment of a flow control device implanted in a bronchial passageway.

FIG. 25 shows another embodiment of the flow control device 110 implanted within a bronchial passageway 910. This embodiment is structurally similar to the embodiment shown in FIGS. 22–24, except that the anchor member 618 comprises a frame 625 that is distally disposed on the flow control device 110 in the manner described above with respect to the embodiments shown in FIGS. 9–18. That is, the flow control device 110 shown in FIG. 25 does not have a cuff that attaches the frame to the flow control member. Rather, the frame 625 is distally separated from the flow control device 110. As shown in FIG. 25, the flow control device 110 includes a valve protector sleeve 1938 that is attached to a proximal end of the valve dilation member 1930. As discussed, the protector sleeve 1938 can have one or more vent holes, which ensure that the pressure is the same on interior and exterior surfaces of the valve dilation member 1930.

Figure 26:
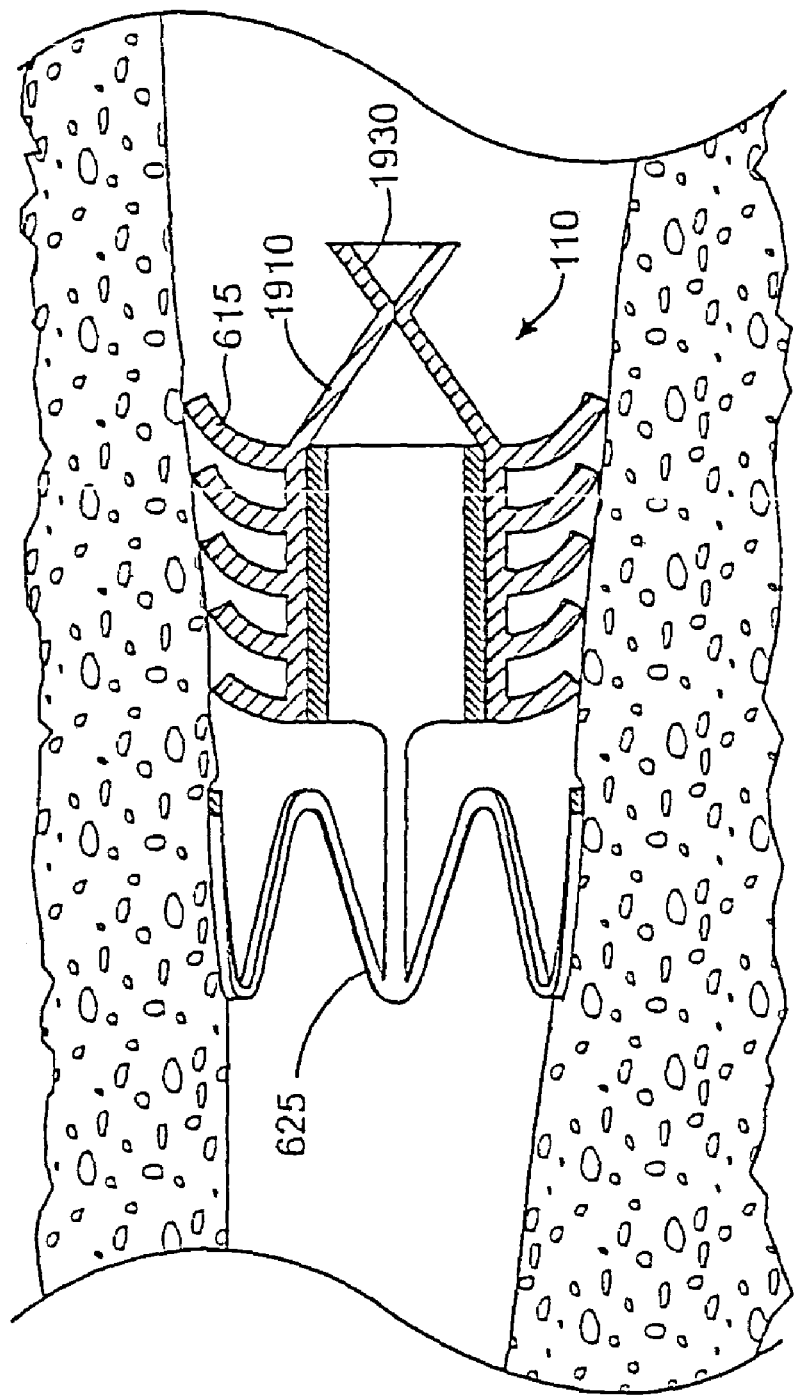
FIG. 26 shows another embodiment of a flow control device implanted in a bronchial passageway.
Figure 27:
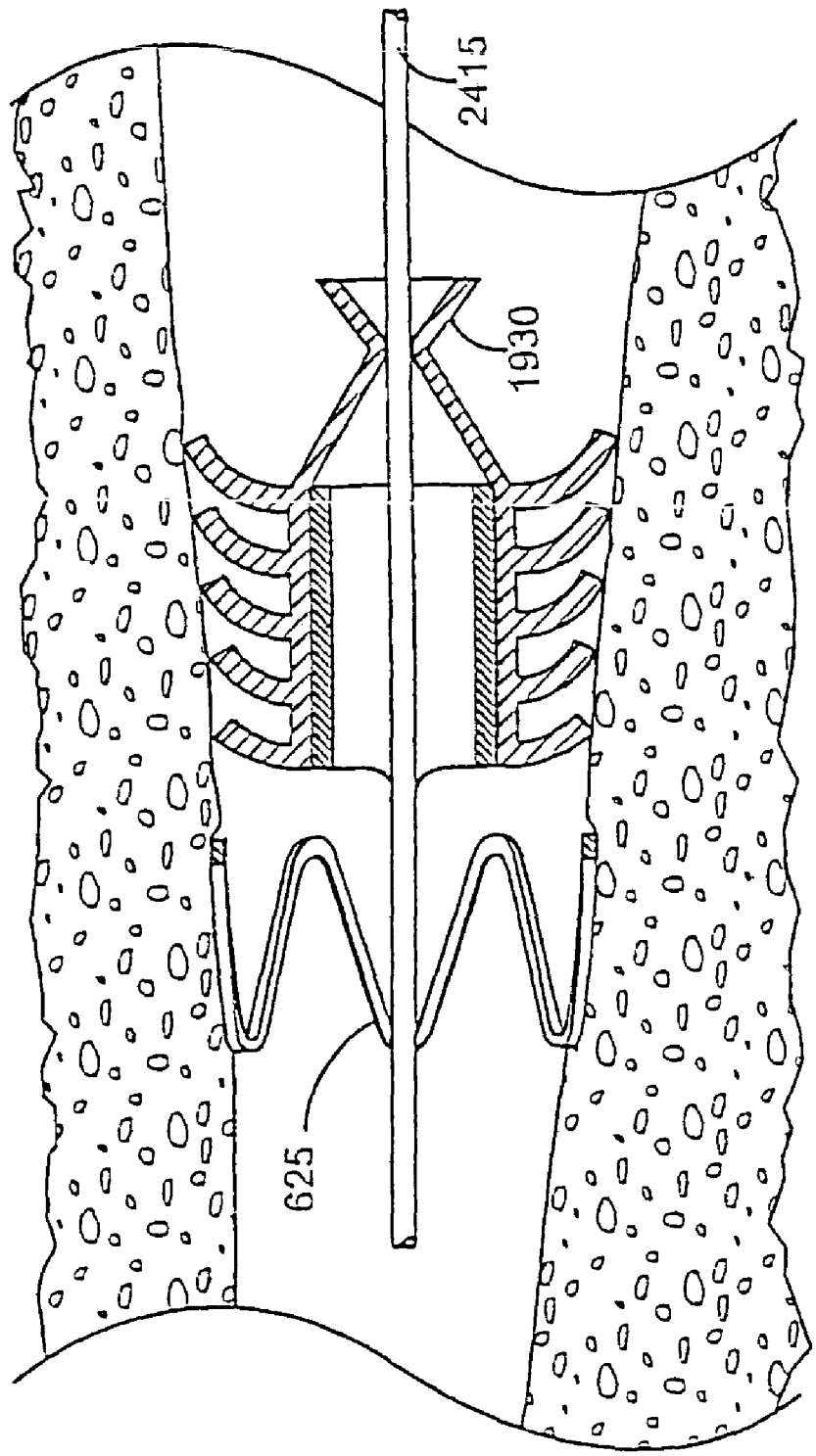
FIG. 27 shows the flow control device of FIG. 26 implanted in a bronchial passageway and dilated by a dilation device.

FIG. 26 illustrates another embodiment of the flow control device 110 that is similar to the embodiment shown in FIG. 25. However, the valve dilation member 1930 has no external support other than its attachment to the duckbill valve 1910. In addition, the duckbill valve 1910 is integrally attached to the seal member 615, although it should be appreciated that the duckbill valve and seal member could also be molded as two separate components and bonded together. FIG. 27 shows the flow control device 110 of FIG. 26 with a dilator device comprised of a dilation catheter 2415 dilating the flow control device 110 through the valve dilation member 1930. The dilation catheter 2415 was inserted from the proximal side of the flow control device 110 for use in passing fluid to or from the distal side, or for performing other therapeutic procedures, as described below.

Figure 28:
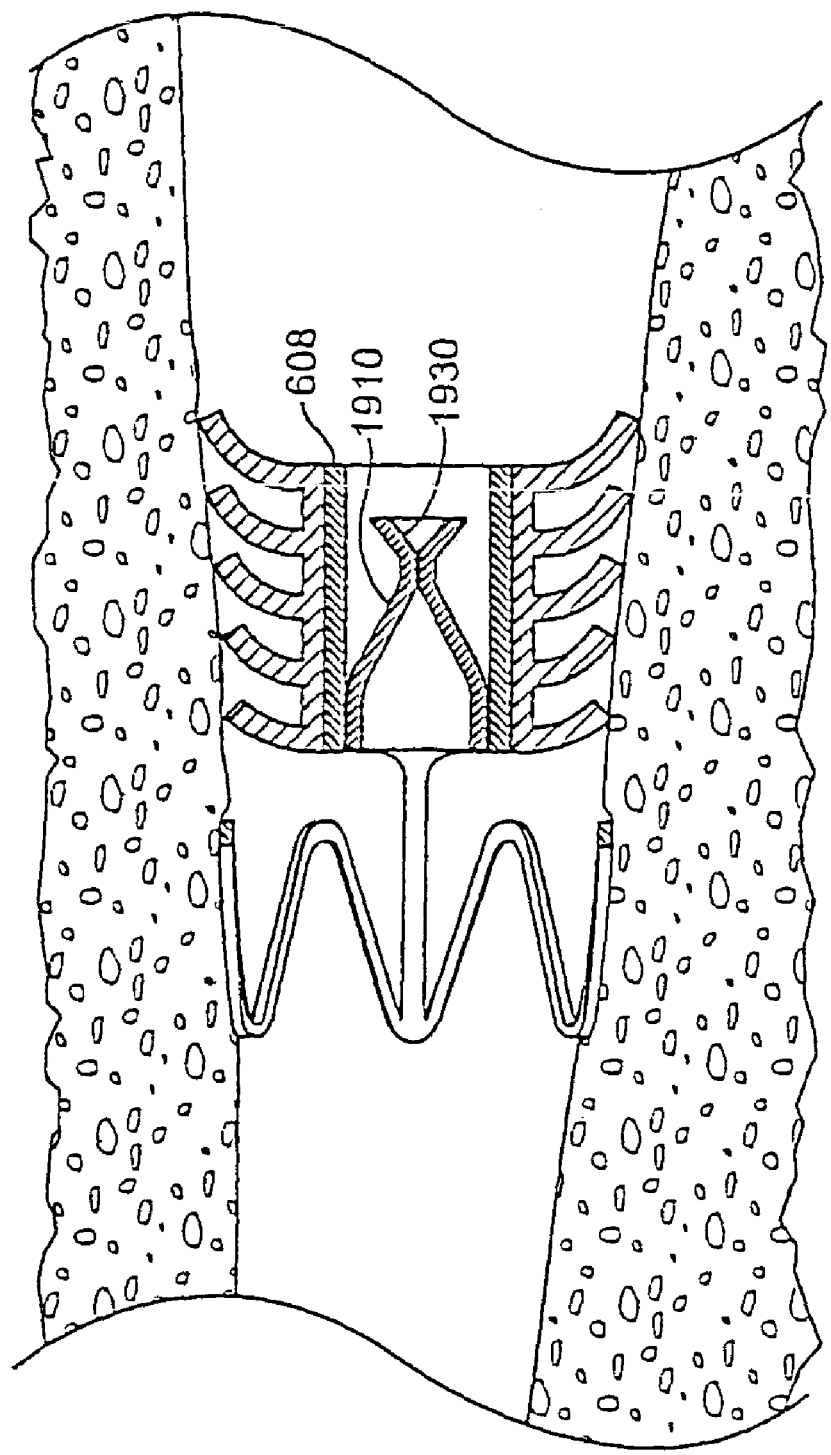
FIG. 28 shows another embodiment of a flow control device implanted in a bronchial passageway.

FIG. 28 shows yet another embodiment of the flow control device 110. In this embodiment, the duckbill valve 1910 and the valve dilation member 1930 are surrounded entirely by the annular wall 608.

Figure 29:
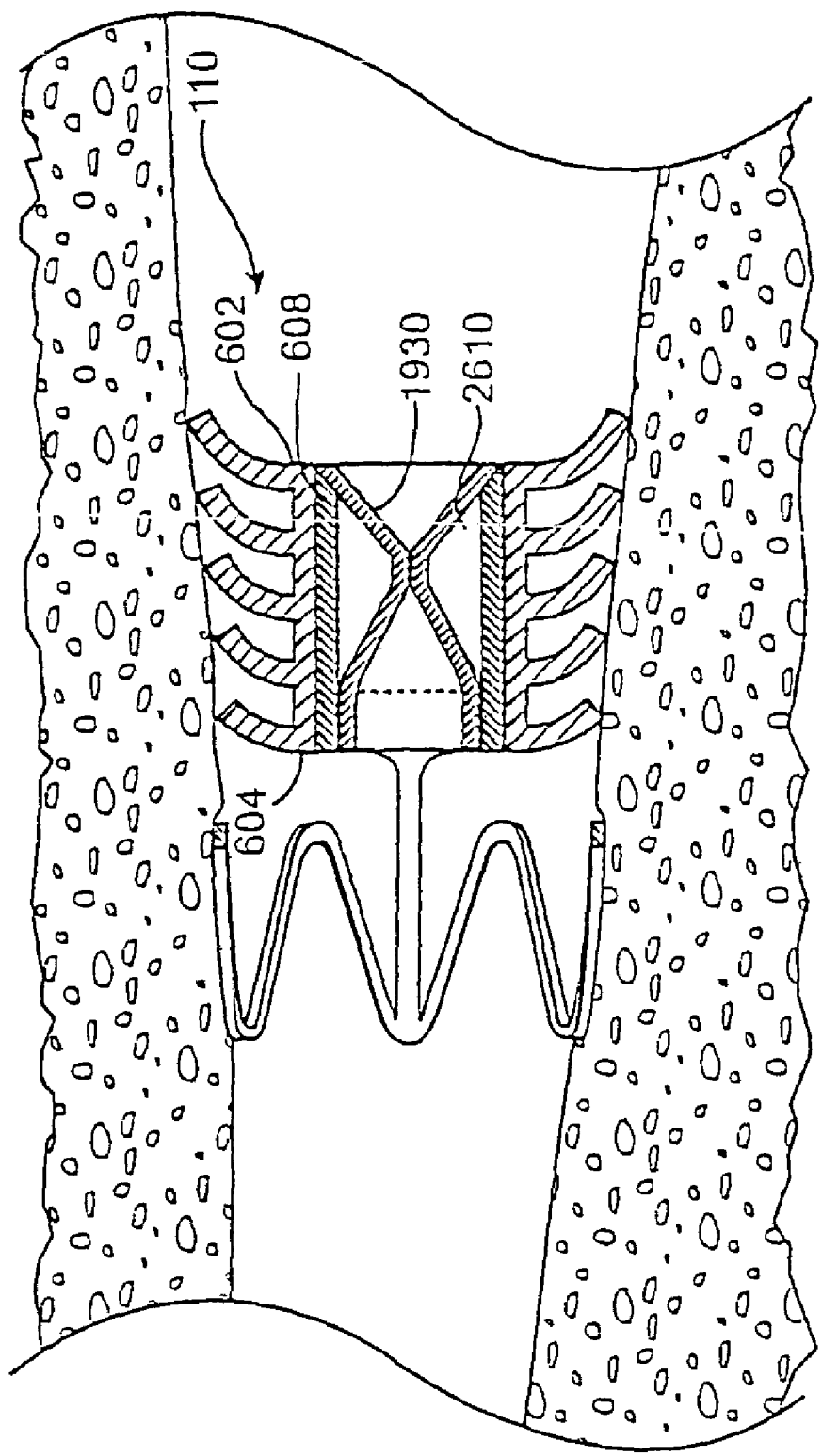
FIG. 29 shows another embodiment of a flow control device implanted in a bronchial passageway that has an internal, sealed chamber.

FIG. 29 shows yet another embodiment of the flow control device 110. The flow control device 110 of FIG. 29 includes a sealed chamber 2610 that is defined by a space between the duckbill valve 1910, the valve dilation member 1930, and the annular wall 608. This structure results in a controlled cracking pressure for flow from the proximal side 602 to the distal side 604 of the flow control device 110 in addition to a controlled cracking pressure for flow from the distal side 604 to the proximal side 602. The cracking pressure in either direction is a function of the pressure in the sealed chamber 2610, the durometer of the material used to fabricate the duckbill valve and the valve dilation member, the thickness of the material, the included angle of the cone portion of the valve member 1910/valve dilation member 1930, etc. In addition, this device allows the passage of dilation devices in the distal direction.

Figure 30:
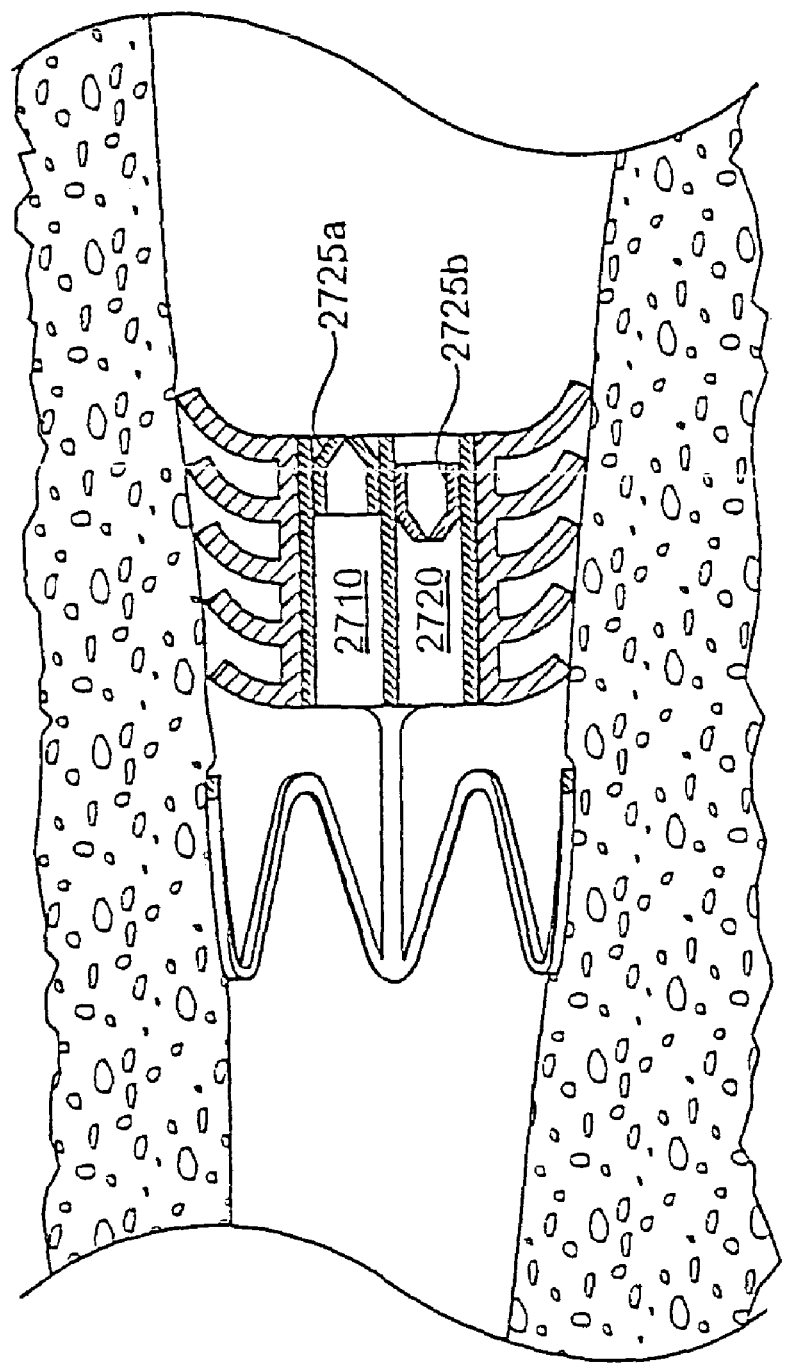
FIG. 30 shows another embodiment of a flow control device implanted in a bronchial passageway, the flow control device having a pair of internal lumens for allowing controlled, two-way fluid flow.

FIG. 30 shows yet another embodiment of the flow control device 110. In this embodiment, the flow control device 110 defines two interior lumens 2710, 2720. The flow control device 110 of FIG. 30 provides for two-way fluid flow, with the interior lumen 2710 providing for fluid flow in a first direction and the interior lumen 2720 providing for fluid flow in a second direction. There is a first one-way duckbill valve 2725a mounted in the interior lumen 2710 that allows fluid flow in a proximal direction and a second duckbill valve 2725b mounted in the interior lumen 2720 that allows fluid flow in a distal direction. This allows for different cracking pressures for fluid flow in either direction.

Figure 31:
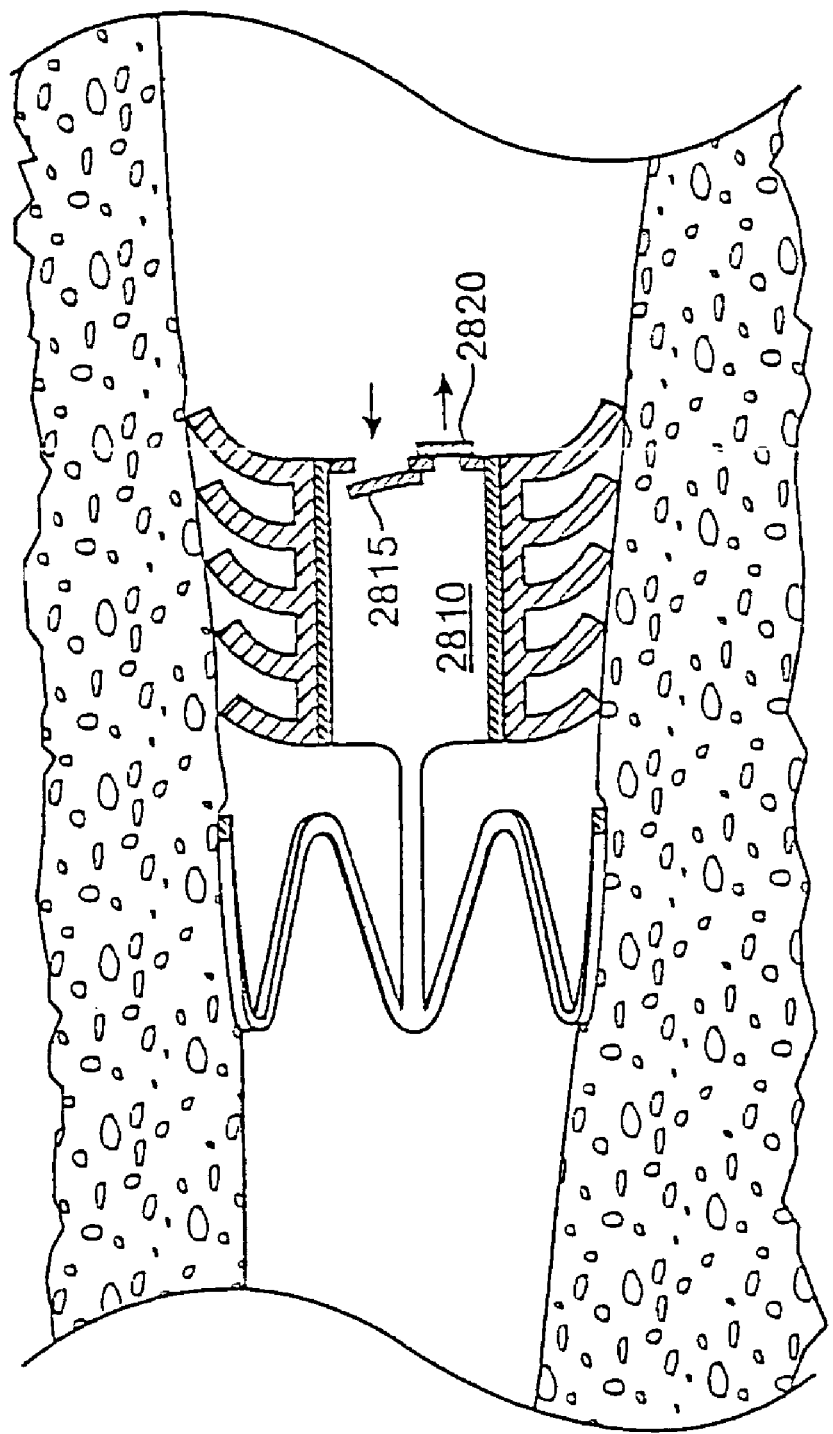
FIG. 31 shows another embodiment of a flow control device implanted in a bronchial passageway, the flow control device having a pair of flap valves for allowing controlled, two-way fluid flow.

FIG. 31 shows another embodiment of a flow control device 110 that permits controlled fluid flow in either a proximal direction or a distal direction. The flow control device 110 has a single interior lumen 2810. The flow control device 110 includes a first valve member comprised of a flap valve 2815 that is configured to permit fluid flow through the lumen 2810 in a first direction when the valve is exposed to a first cracking pressure. A second valve 2820 permits fluid flow in a second direction through the lumen at a second cracking pressure.

Cracking Pressure

The cracking pressure is defined as the minimum fluid pressure necessary to open the one-way valve member in a certain direction, such as in the distal-to-proximal direction. Given that the valve member of the flow control device 110 will be implanted in a bronchial lumen of the human lung, the flow control device 110 will likely be coated with mucus and fluid at all times. For this reason, the cracking pressure of the valve is desirably tested in a wet condition that simulates the conditions of a bronchial lumen. A representative way of testing the valve member is to use a small amount of a water based lubricant to coat the valve mouth. The testing procedure for a duckbill valve is as follows:

1. Manually open the mouth of the valve member, such as by pinching the sides of the valve together, and place a drop of a dilute water based lubricant (such as Liquid K-Y Lubricant, manufactured by Johnson & Johnson Medical, Inc.) between the lips of the valve.
2. Wipe excess lubricant off of the valve, and force 1 cubic centimeter of air through the valve in the forward direction to push out any excess lubricant from the inside of the valve.
3. Connect the distal side of the valve to an air pressure source, and slowly raise the pressure. The pressure is increased from a starting pressure of 0 inches H2O up to a maximum of 10 inches H2O over a period of time (such as 3 seconds), and the peak pressure is recorded.

This peak pressure represents the cracking pressure of the valve.

The smaller the duckbill valve, the higher the cracking pressure that is generally required to open the valve. The cracking pressure of small valves generally cannot be reduced below a certain point as the valve will have insufficient structural integrity, as the wall thickness of the molded elastomer is reduced, and the durometer is decreased. For the flow control device 110, the lower the cracking pressure is the better the performance of the implant.

In one embodiment, the cracking pressure of the valve member is in the range of approximately 2.6–4.7 inches H2O. In another embodiment, wherein the valve is larger than the previously-mentioned embodiment, the cracking pressure of the valve is in the range of 1.7–4.5 inches H2O. In yet another embodiment, wherein the valve is larger than the previously-mentioned embodiment, the cracking pressure of the valve is in the range of 2.0–4.1 inches H2O. In yet another embodiment, wherein the valve is larger than the previously-mentioned embodiment, the cracking pressure of the valve is in the range of 1.0–2.7 inches H2O. The cracking pressure of the valve member can vary based on various physiological conditions. For example, the cracking pressure could be set relative to a coughing pressure or a normal respiration pressure. For example, the cracking pressure could be set so that it is higher (or lower) than a coughing pressure or normal respiration pressure. In this regard, the coughing or normal respiration pressure can be determined based on a particular patient, or it could be determined based on average coughing or normal respiration pressures.

Delivery System

Figure 32:
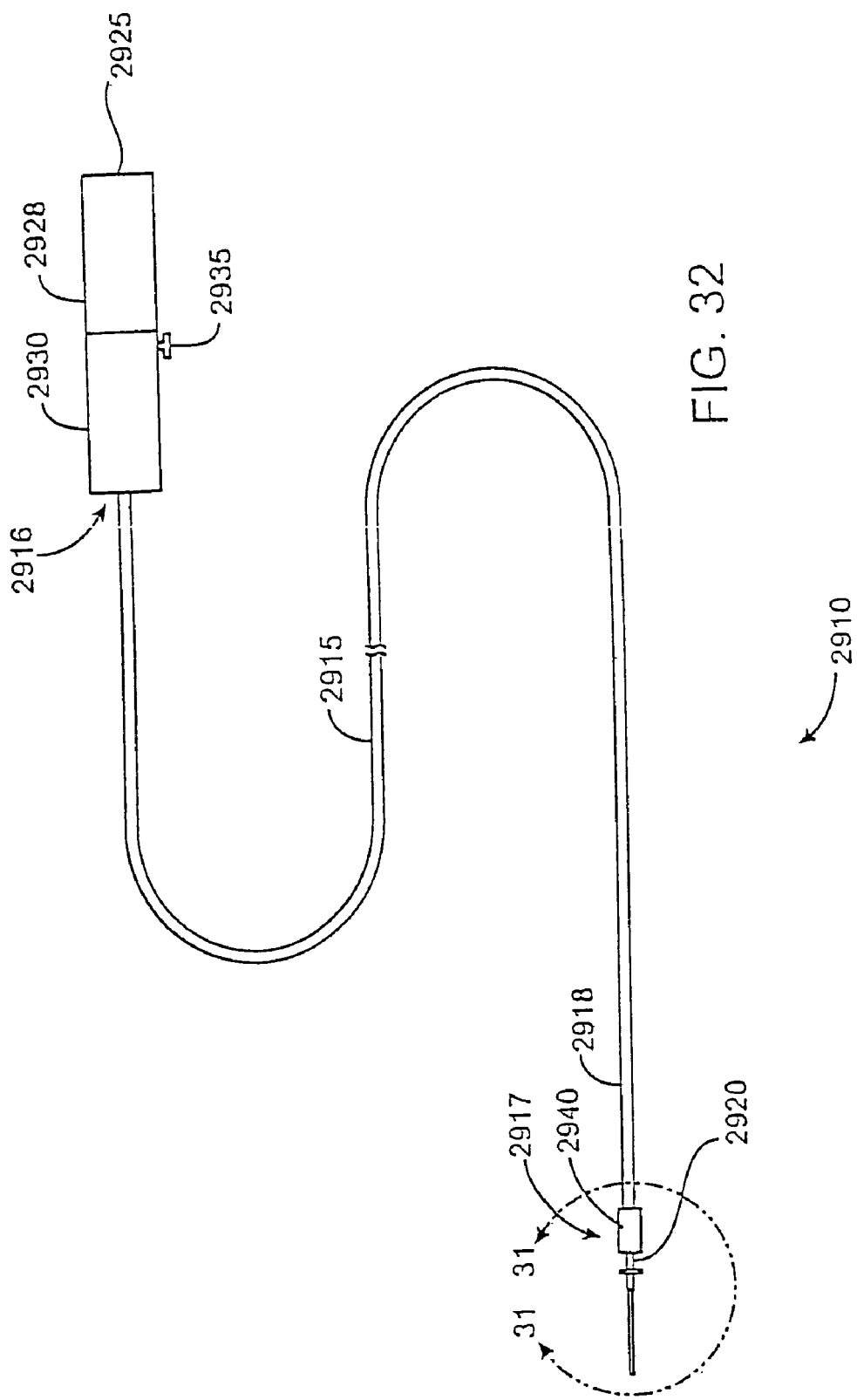
FIG. 32 shows a delivery system for delivering a flow control device to a target location in a body passageway.

FIG. 32 shows a delivery system 2910 for delivering and deploying a flow control device 110 to a target location in a bronchial passageway. The delivery system 2910 includes a catheter 2915 having a proximal end 2916, and a distal end 2917 that can be deployed to a target location in a patient's bronchial passageway, such as through the trachea. The catheter 2915 has an outer member 2918 and an inner member 2920 that is slidably positioned within the outer member 2918 such that the inner member 2920 can slidably move relative to the outer member 2918 along the length of the catheter 2915.

In this regard, an actuation member, such as a two-piece handle 2925, is located at the proximal end 2916 of the catheter 2915. The handle 2925 can be actuated to move the inner member 2920 relative to the outer member 2918 (and vice-versa). In the illustrated embodiment, the handle 2925 includes a first piece 2928 and a second piece 2930, which is slidably moveable with respect to the first piece 2928. The inner member 2920 of the catheter 2915 can be moved relative to the outer member 2918 by slidably moving the first piece 2928 of the handle 2925 relative to the second piece 2930. This can be accomplished, for example, by attaching the proximal end of the catheter inner member 2920 to the first piece 2928 of the handle 2925 and attaching the proximal end of the catheter outer member 2918 to the second piece 2930. The actuation member could also take on other structural forms that use other motions to move the inner member 2920 relative to the outer member 2918. For example, the actuation member could have scissor-like handles or could require a twisting motion to move the inner member 2920 relative to the outer member 2918.

As shown in FIG. 32, the handle 2925 also includes a locking mechanism 2935 for locking the position of the first piece 2928 relative to the second piece 2930 to thereby lock the position of the inner member 2920 of the catheter 2915 relative to the outer member 2918. The locking mechanism 2935 can comprise, for example, a screw or some other type of locking mechanism that can be used to lock the position of the first piece 2928 of the handle 2925 relative to the second piece 2930.

The outer member 2918, and possibly the inner member 2920, can include portions of differing stiffness to allow discrete portions of the members to bend and deflect more easily than other portions. In one embodiment, the distal portion of the catheter 2915, for example, the last 10 cm or so just proximal to a distally-located housing 2940, can be made to have a reduced bending stiffness. This would allow the distal end 2917 of the catheter 2915 to bend easily around angles created by branches in the bronchial tree, and could make placement of flow control devices easier in more distal locations of the bronchial tree.

The outer member 2918 of the catheter 2915 could also include wire reinforcing to improve certain desired characteristics. The outer member 2918 could be manufactured to include wire winding or braiding to resist kinking, wire braiding to improve the ability of the catheter 2915 to transmit torque, and longitudinal wire or wires to improve tensile strength while maintaining flexibility, which can improve device deployment by reducing recoil or "springiness" in the outer member 2918. The inner member 2920 could also include wire reinforcing, such as wire winding, wire braiding, or longitudinal wire(s) to resist kinking and add compressive strength to the inner member 2920.

Figure 33:
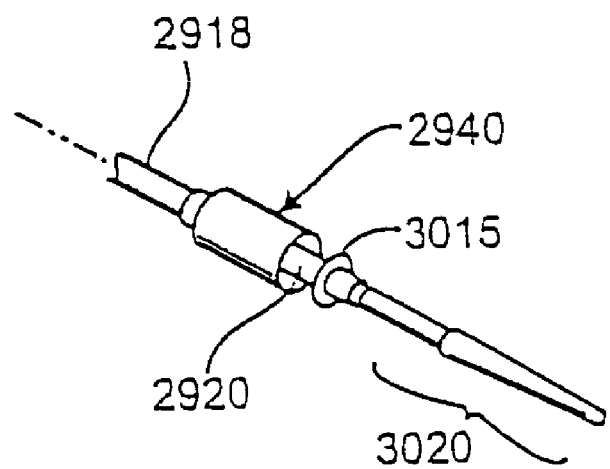
FIG. 33 shows a perspective view of a distal region of a delivery catheter of the delivery system.
Figure 34:
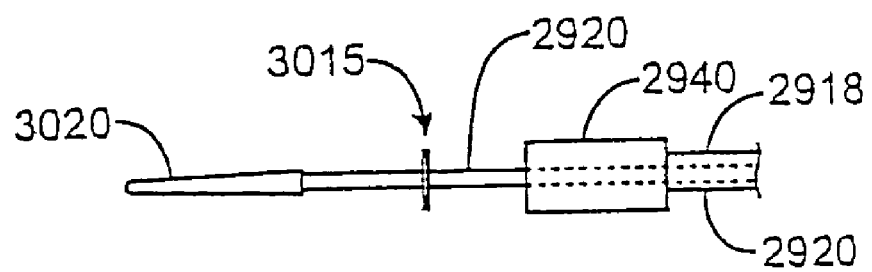
FIG. 34 shows a plan, side view of the distal region of the delivery catheter.

With reference still to FIG. 32, a housing 2940 is located at or near a distal end of the catheter 2915. The housing 2940 is attached to a distal end of the outer member 2918 of the catheter 2915 but not attached to the inner member 2920. As described in more detail below, the housing 2940 defines an inner cavity that is sized to receive the flow control device 110 therein. FIG. 33 shows an enlarged, perspective view of the portion of the distal portion of the catheter 2915 where the housing 2940 is located. FIG. 34 shows a plan, side view of the distal portion of the catheter 2915 where the housing 2940 is located. As shown in FIGS. 33 and 34, the housing 2940 is cylindrically-shaped and is open at a distal end and closed at a proximal end. The inner member 2920 of the catheter 2915 protrudes through the housing and can be slidably moved relative to the housing 2940. An ejection member, such as a flange 3015, is located at a distal end of the inner member 2920. As described below, the ejection member can be used to eject the flow control device 110 from the housing 2940. The flange 3015 is sized such that it can be received into the housing 2940. The housing can be manufactured of a rigid material, such as steel.

In one embodiment, a tip region 3020 is located on the distal end of the inner member 2920, as shown in FIGS. 33 and 34. The tip region 3020 can be atraumatic in that it can have a rounded or cone-shaped tip that facilitates steering of the catheter 2915 to a desired bronchial passageway location. The atraumatic tip region 3020 preferably includes a soft material that facilitates movement of the atraumatic tip region 3020 through the trachea and bronchial passageway(s). In this regard, the atraumatic tip region 3020 can be manufactured of a soft material, such as polyether block amide resin (Pebax), silicone, urethrane, and the like. Alternately, the tip region 3020 can be coated with a soft material, such as any of the aforementioned materials.

The inner member 2920 of the catheter 2915 can include a central guide wire lumen that extends through the entire length of the catheter 2915, including the atraumatic tip region 3020, if present. The central guide wire lumen of the inner member 2920 is sized to receive a guide wire, which can be used during deployment of the catheter 2915 to guide the catheter 2915 to a location in a bronchial passageway, as described more fully below.

In an alternative embodiment of the catheter 2915, the catheter 2915 could be fitted with a short length of flexible, bendable guide wire on the distal end of the catheter 2915. The bendable guide wire could be used to ease the passage of the catheter 2915 through the bronchial anatomy during deployment of the catheter 2915. The fixed guide wire could include a soft, flexible atraumatic tip. The wire portion could be deformed into various shapes to aid in guiding the catheter 2915 to the target location. For example, the wire could be bent in a soft "J" shape, or a "hockey stick" shape, and thus the tip of the guide wire could be directed to one side or another by rotating the catheter 2915, thereby allowing the catheter 2915 to be guided into a branch of the bronchial tree that diverts at an angle away from the main passage.

In another embodiment similar to that detailed above, the distal portion of the delivery catheter 2915, proximal to the housing 2940, could be made deformable. This would allow the distal end of the catheter 2915 to be shaped, thus allowing the catheter 2915 to be guided into a bronchial side branch by rotating the catheter shaft.

The delivery catheter 2915 could be modified to add a steerable distal tip function, such as by adding a "pull" wire located inside a new lumen in the outer member 2918 of the delivery catheter 2915. The proximal end of the pull wire would be attached to a movable control that allows tension to be applied to the wire. The distal end of the wire would be terminated at a retainer attached to the distal end of the outer member 2918 of the catheter 2915. The distal portion of the catheter 2915 could be manufactured to be much more flexible than the rest of the catheter 2915, thus allowing the distal end of the catheter 2915 to bend more easily than the rest of the catheter 2915. This distal portion could also have some elastic restoring force so that it will return on its own to a straight configuration after the tip is deflected or the shape of the tip is disturbed. When the moveable control is actuated, thus applying tension to the pull wire, the distal tip or distal portion of the catheter 2915 will deflect. In addition, other ways of constructing steering tips for this delivery catheter could be used.

An alternate embodiment of the steerable delivery catheter 2915 is one where the distal tip or distal region of the delivery catheter 2915 is permanently deformed into a bent shape, with the bent shape corresponding with the greatest desired deflection of the distal tip. The outer member 2918 of the delivery catheter can have an additional lumen running along one side, allowing a rigid or semi-rigid mandrel or stylet to be inserted in the lumen. If the mandrel is straight, as it is inserted into the side lumen of the catheter 2915, the deformed tip of the catheter 2915 will progressively straighten as the mandrel is advanced. When the mandrel is fully inserted, the outer shaft of the catheter 2915 also becomes straight. The catheter 2915 can be inserted into the patient in this straight configuration, and the mandrel can be withdrawn as needed to allow the tip to deflect. In addition, the mandrel or stylet could be formed into different shapes, and the catheter 2915 would conform to this shape when the mandrel is inserted into the side lumen.

As mentioned, the housing 2940 defines an interior cavity that is sized to receive the flow control device 110. This is described in more detail with reference to FIG. 35A, which shows a cross-sectional view of the housing 2940 with a flow control device 110 positioned within the housing 2940. For clarity of illustration, the flow control device 110 is represented as a dashed box in FIG. 35A. The housing 2940 can be sufficiently large to receive the entire flow control device 110 without any portion of the flow control device protruding from the housing 2940, as shown in FIG. 35A.

Alternately, the housing 2940 can be sized to receive just a portion of the flow control device 110. For example, the distal end 604 of the flow control device 110 can be shaped as shown in FIG. 35B, but can protrude out of the housing 2940 when the flow control device 110 is positioned within the housing 2940. In such a case, the distal end 604 of the flow control device 110 can be made of an atraumatic material to reduce the likelihood of the distal end 604 damaging a body passageway during deployment.

Alternately, or in combination with the soft material, the distal end can be tapered so that it gradually reduces in diameter moving distally away from the housing, such as is shown in FIG. 35B. The tapered configuration can be formed by a taper in the shape of the distal edge of the cuff, if the flow control device 110 has a cuff. Or, if the distal edge of the flow control device 110 is a frame, then the frame can be shaped to provide the taper. As shown in FIG. 35B, the tapered configuration of the distal end 604 of the flow control device 110 can provide a smooth transition between the outer diameter of the distal end 3020 of the catheter inner member 2920 and the outer diameter of the distal edge of the housing 2940. This would eliminate sharp transitions in the delivery system profile and provide for smoother movement of the delivery system through the bronchial passageway during deployment of the flow control device 110. The housing 2940 preferably has an interior dimension such that the flow control device 110 is in a compressed state when the flow control device 110 is positioned in the housing 2940.

Figure 35A:
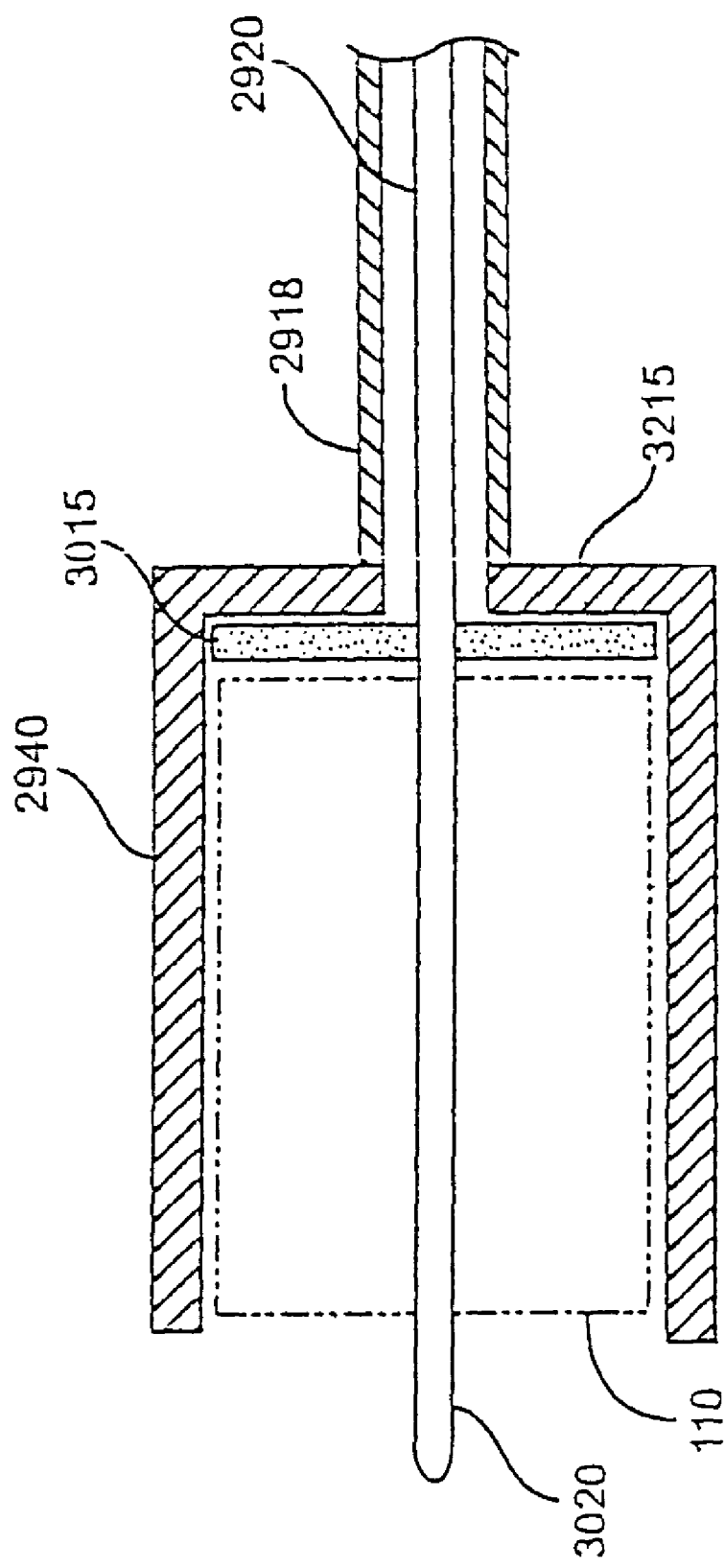
FIG. 35A shows a cross-sectional view of a housing of the delivery catheter, the housing containing a flow control device.
Figure 35B:
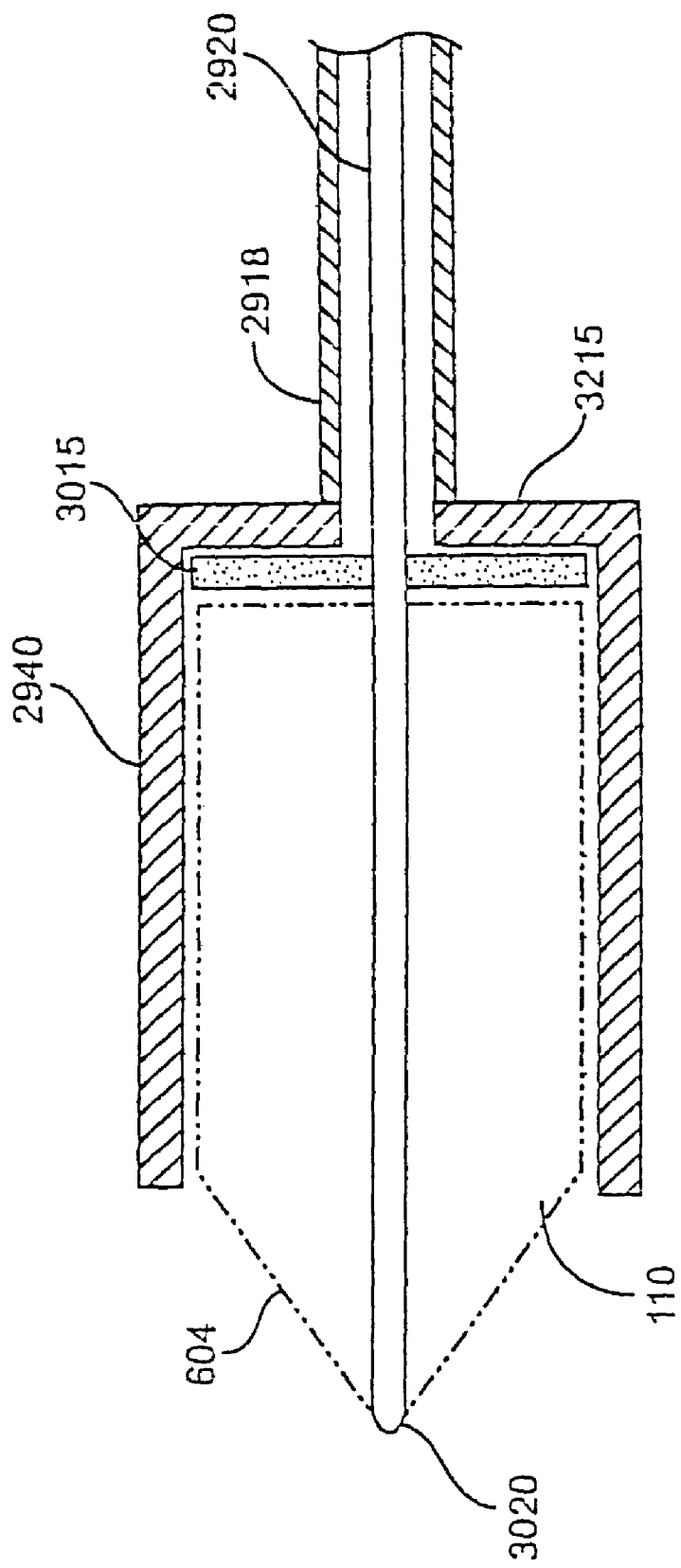
FIG. 35B shows a cross-sectional view of the housing containing a flow control device that has a distal end that protrudes from the housing.

As shown in FIGS. 35A,B, the flow control device 110 abuts or is adjacent to the flange 3015 of the catheter inner member 2920 when the flow control device is positioned within the housing 2940. As mentioned, the catheter inner member 2920 is moveable relative to the housing 2940 and the catheter outer member 2918. In this regard, the flange 3015 can be positioned to abut a base portion 3215 of the housing 2940 so that the flange 3015 can act as a detent for the range of movement of the catheter inner member 2920 relative to the catheter outer member 2918.

As described in more detail below, the catheter 2915 can be used to deliver a flow control device 110 to a desired bronchial passageway location. This is accomplished by first loading the flow control device into the housing 2940 of the catheter 2915. The distal end of the catheter 2915 is then deployed to the desired bronchial passageway location such that the housing (and the loaded flow control device 110) are located at the desired bronchial passageway location. The flow control device 110 is then ejected from the housing 2940.

Figure 36A:
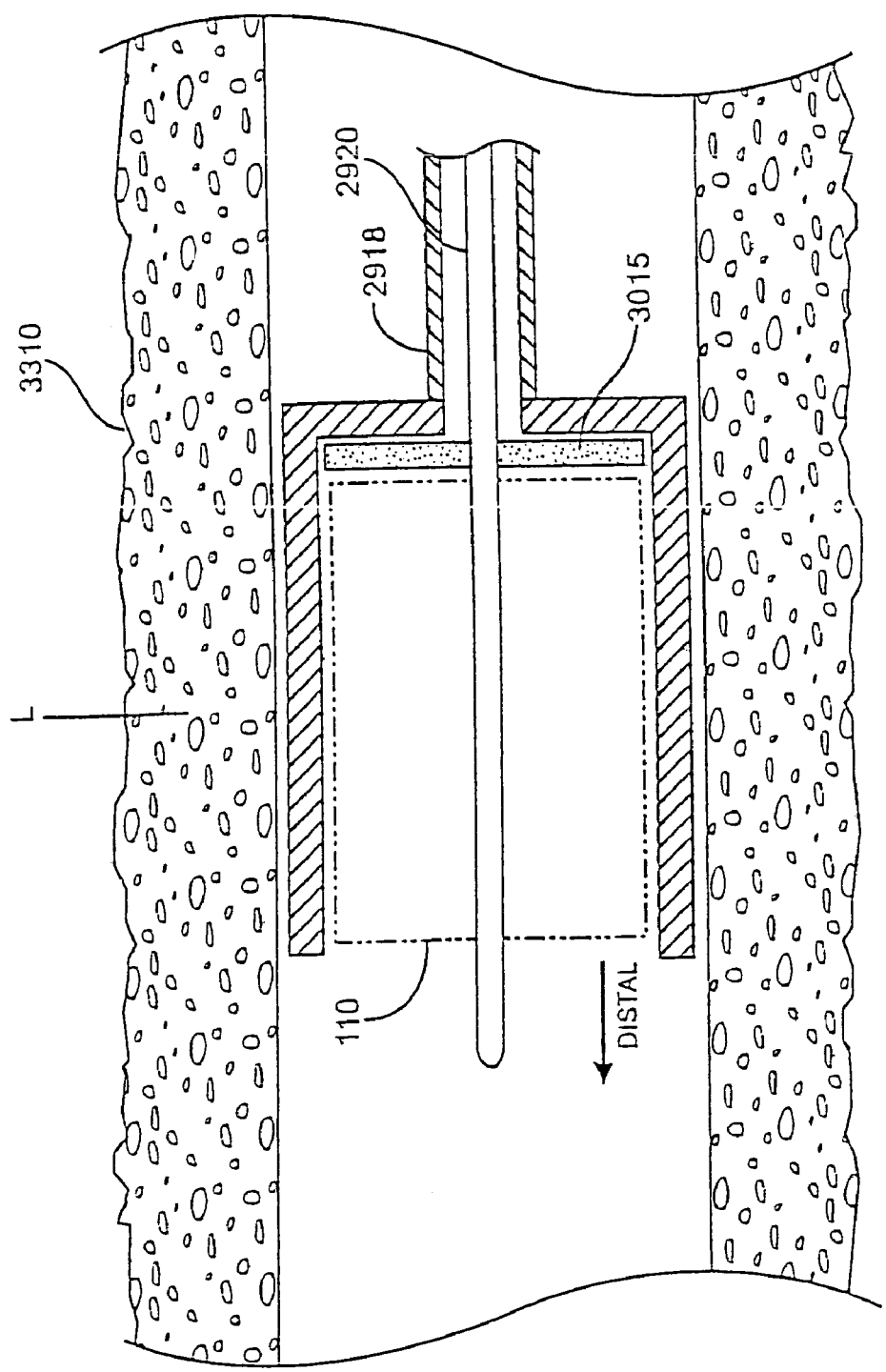
FIG. 36A shows the delivery catheter housing containing a flow control device and implanted at a location L of a bronchial passageway.
Figure 36B:
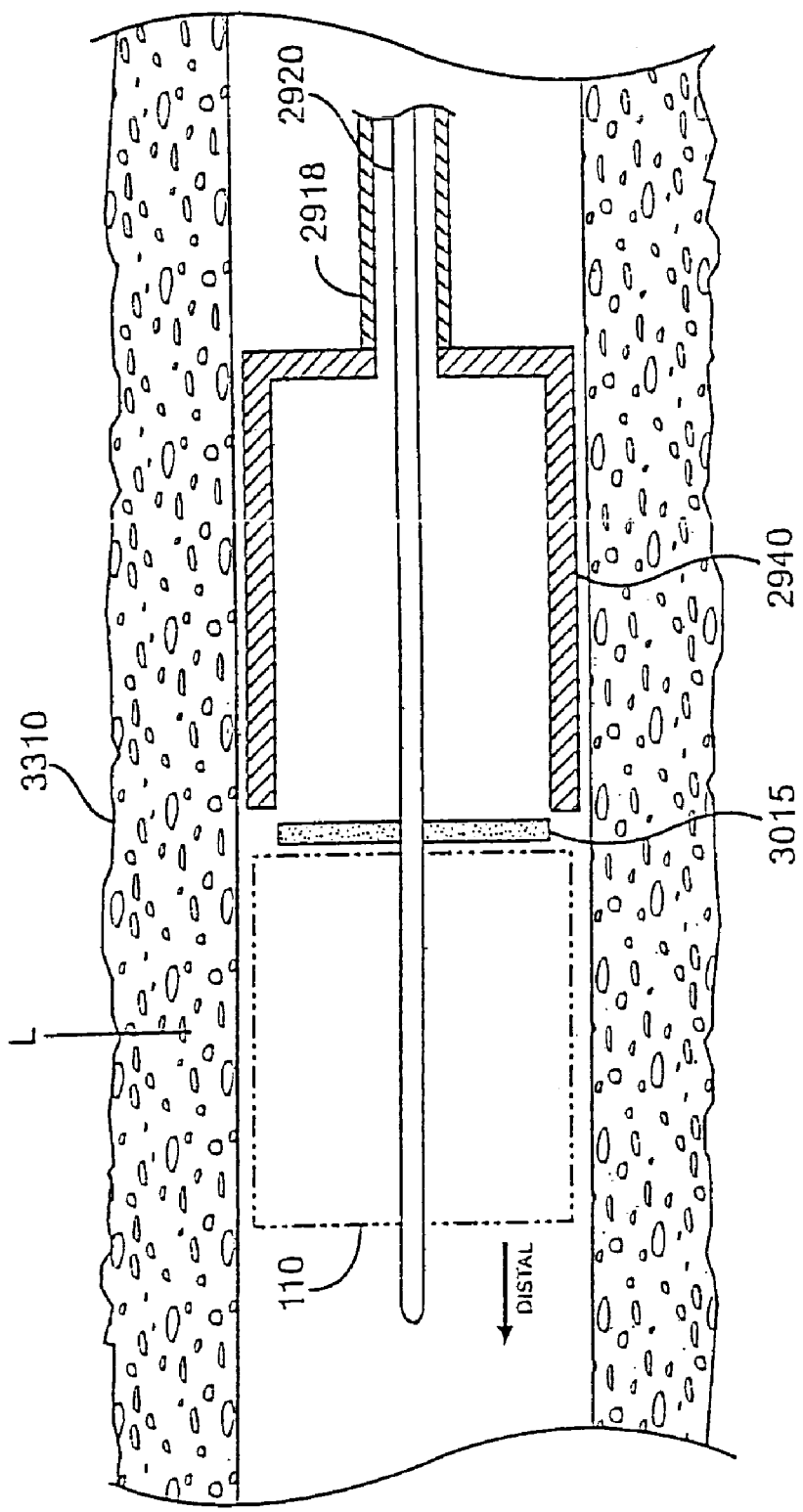
FIG. 36B shows the delivery catheter deploying the flow control device at the location L of the bronchial passageway.

The ejection of the flow control device 110 from the housing 2940 can be accomplished in a variety of ways. For example, as shown in FIG. 36A, the catheter 2915 is deployed to a target location L of a bronchial passageway 3310. The catheter handle 2925 is then actuated to move the outer catheter member 2918 in a proximal direction relative to the location L, while maintaining the location of the flow control device 110, inner member 2920, and flange 3015 fixed with respect to the location L. The proximal movement of the outer member 2918 will cause the attached housing 2940 to also move in a proximal direction, while the flange 3015 will act as a detent that prevents the flow control device 110 from moving in the proximal direction. This will result in the housing 2940 sliding away from engagement with the flow control device 110 so that the flow control device 110 is eventually entirely released from the housing 2940 and implanted in the bronchial passageway, as shown in FIG. 36B. In this manner, the flow control device 110 can be implanted at the location L where it was originally positioned while still in the housing 2940.

Figure 37:
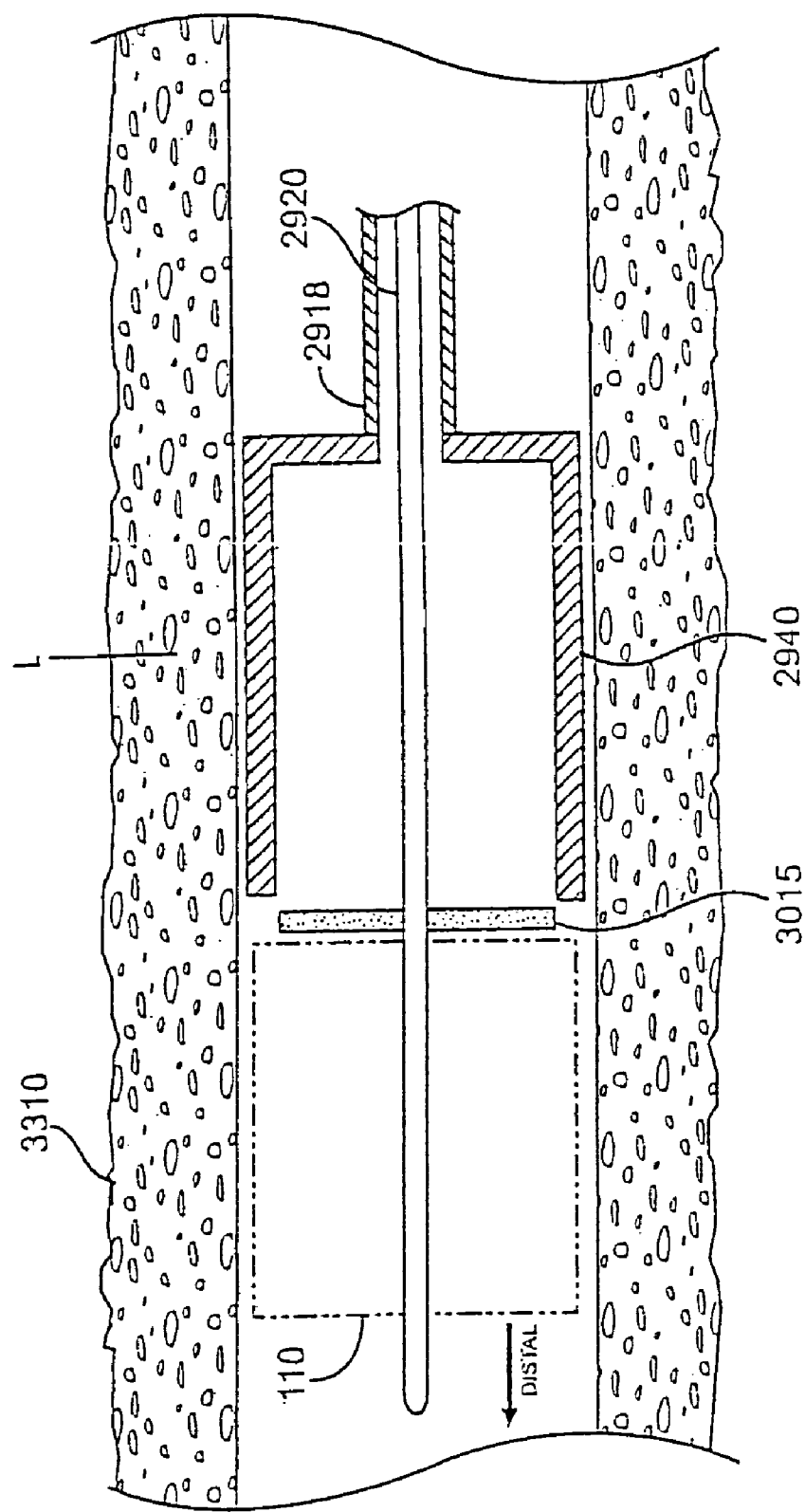
FIG. 37 shows the delivery catheter deploying the flow control device distally of the location L of the bronchial passageway.

According to another procedure for ejecting the flow control device 110 from the housing, the catheter 2915 is implanted to a location L of a bronchial passageway 3310, as shown in FIG. 36A. The catheter handle 2925 is then actuated to move the inner catheter member 2920 (and the attached flange 3015) in a distal direction relative to the location L, while maintaining the location of the outer member 2918 and the housing 2940 fixed with respect to the location L. The distal movement of the flange 3015 will cause the flange 3015 to push the flow control device 110 in a distal direction relative to the location L, while the location of the housing 2940 will remain fixed. This will result in the flow control device 110 being ejected from engagement with the housing 2940 so that the flow control device 110 is eventually entirely released from the housing 2940 and implanted in the bronchial passageway distally of the original location L, as shown in FIG. 37.

Loader System

Figure 38:
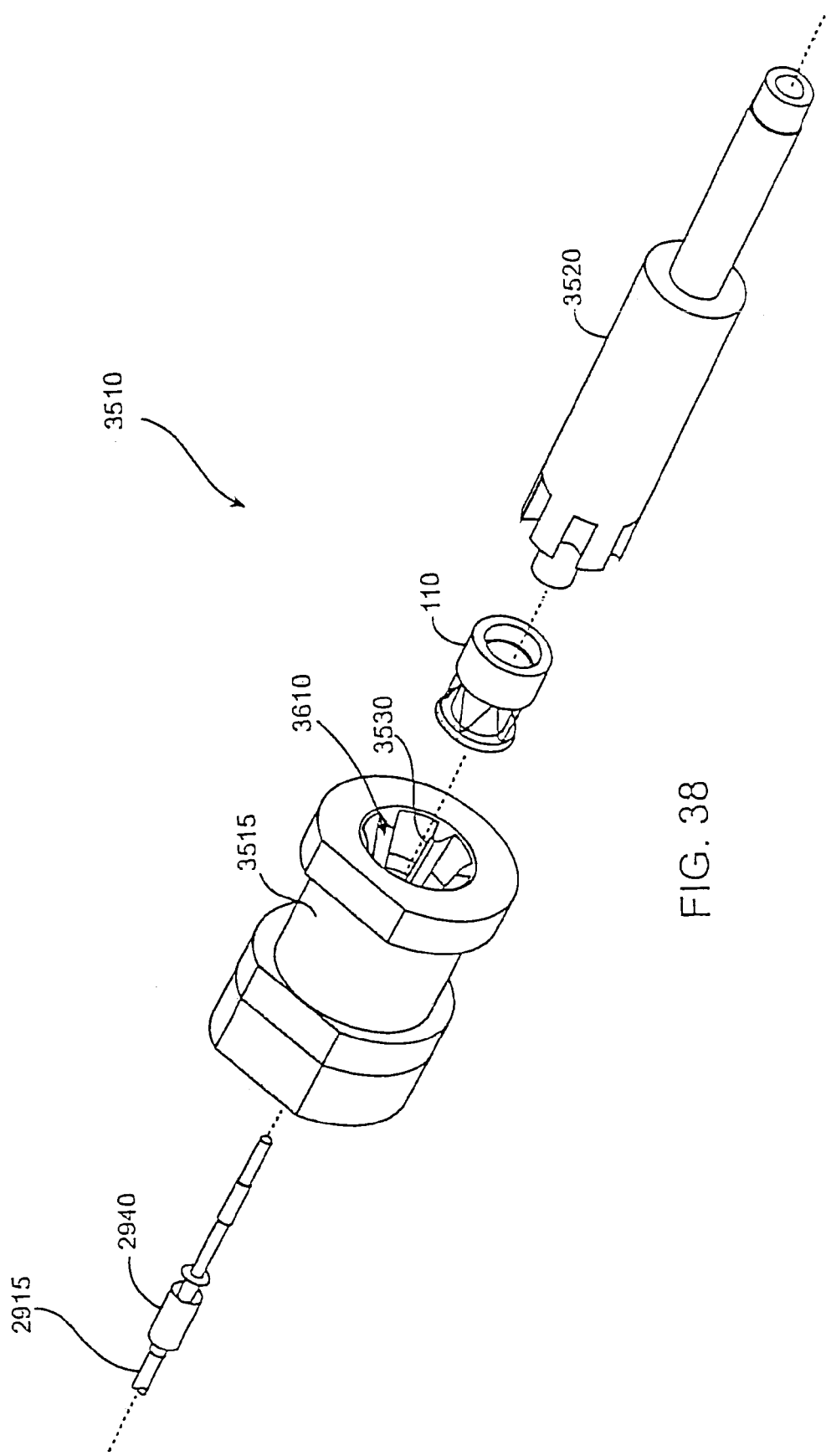
FIG. 38 is a perspective view of a loader system for loading the flow control device onto a delivery catheter.

As discussed above, the flow control device 110 is in a compressed state when it is mounted in the housing 2940 of the delivery catheter 2915. Thus, the flow control device 110 should be compressed to a smaller diameter prior to loading the flow control device 110 into the housing 2940 so that the flow control device 110 can fit in the housing. FIG. 38 shows a perspective view of one embodiment of a loader system 3510 for compressing the flow control device 110 to a smaller diameter and for inserting the flow control device 110 into the delivery catheter housing 2940. The loader system 3510 can be used to securely hold the catheter housing 2940 in place and to properly align the housing 2940 relative to the flow control device 110 during insertion of the flow control device 110 into the housing 2940. This facilitates a quick and easy loading of the flow control device 110 into the housing 2940 and reduces the likelihood of damaging the flow control device 110 during loading.

The loader system 3510 includes a loader device 3515 and a pusher device 3520. As described in detail below, the loader device 3515 is used to compress the flow control device 110 to a size that can fit into the housing 2940 and to properly align the flow control device 110 with the housing 2940 during insertion of the flow control device 110 into the housing 2940. The pusher device 3520 is configured to mate with the loader device 3515 during loading, as described more fully below. The pusher device 3520 is used to push the flow control device 110 into the loader device 3515 and into the housing 2940 during loading, as described in more detail below.

Figure 39:
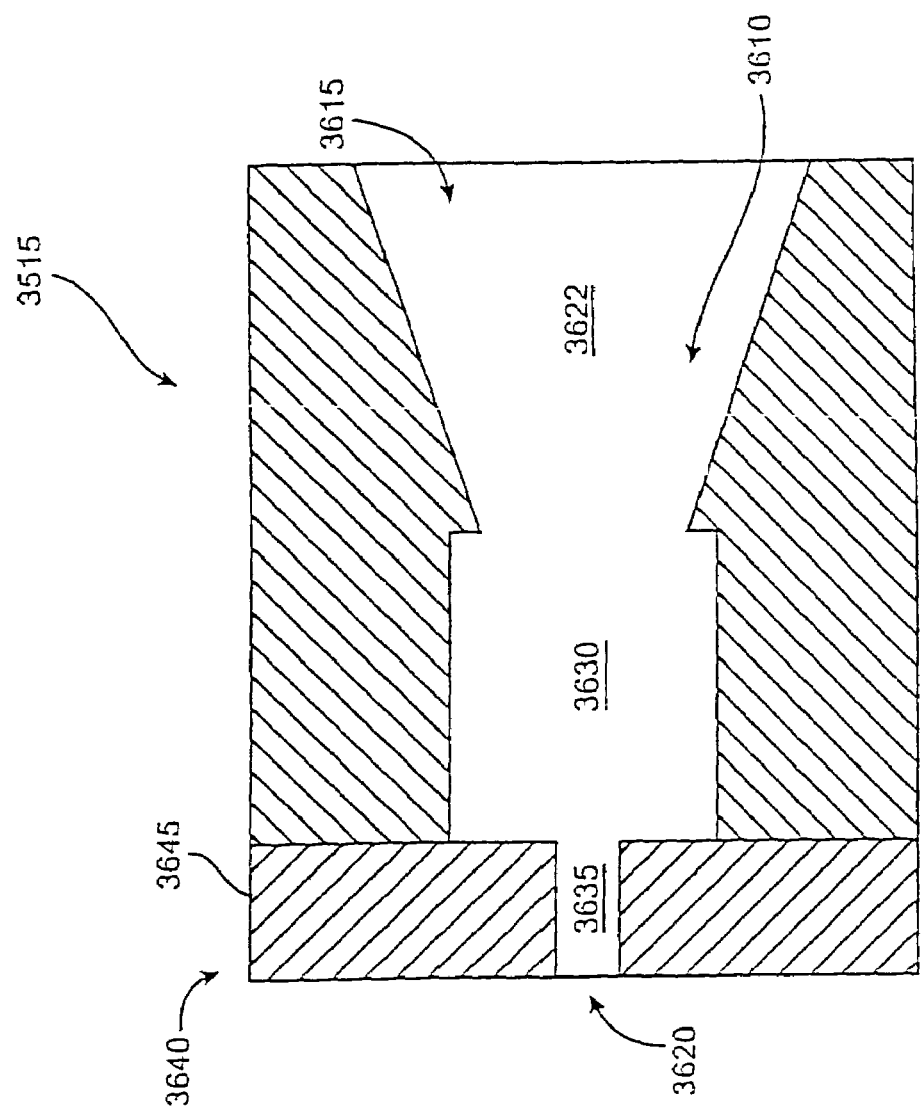
FIG. 39 shows a cross-sectional side view of a loader device of the loader system.

FIG. 39 is a schematic, cross-sectional view of the loader device 3515. A loading tunnel 3610 extends entirely through a main body of the loader device 3515 so as to form a front opening 3615 and an opposed rear opening 3620. The loading tunnel 3610 can have a circular cross-sectional shape, although it should be appreciated that the loading tunnel 3610 could have other cross-sectional shapes. The loading tunnel 3610 has three regions, including a funnel-shaped loading region 3622, a housing region 3630, and a catheter region 3635. The loading region 3622 of the loading tunnel 3610 gradually reduces in diameter moving in a rearward direction (from the front opening 3615 toward the rear opening 3620) so as to provide the loading region 3622 with a funnel shape. The housing region 3630 has a shape that substantially conforms to the outer shape of the catheter housing 2940 so that the catheter housing 2940 can be inserted into the housing region 3630, as described below. The catheter region 3635 is shaped to receive the outer member 2918 of the catheter 2915.

The loader device 3515 can also include a catheter locking mechanism 3640 comprised of a door 3645 that can be opened to provide the catheter 2915 with access to the housing region 3630 of the loading tunnel 3610. The door 3645 can be manipulated to vary the size of the rear opening 3620 to allow the housing 2940 to be inserted into the housing region 3630, as described in more detail below.

Figure 40:
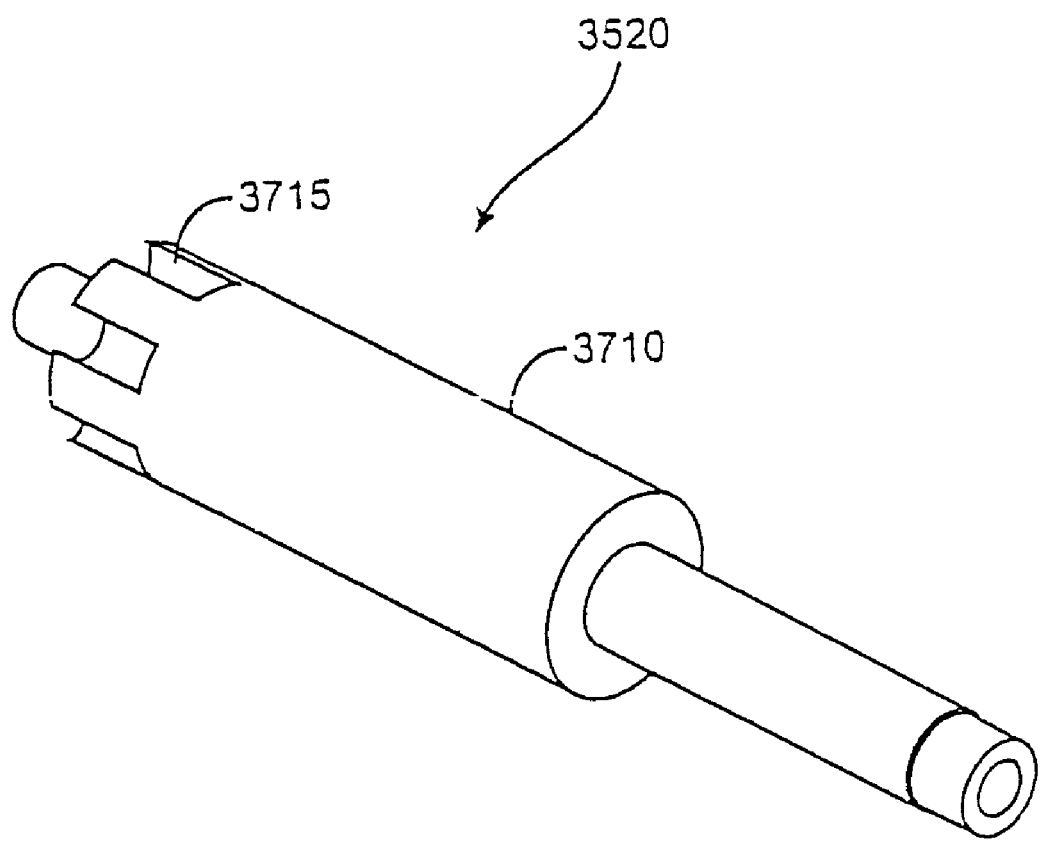
FIG. 40 shows a perspective view of a pusher device of the loader system.

FIG. 40 shows a perspective view of a first embodiment of the pusher device 3520. Additional embodiments of the pusher device 3520 are described below. The pusher device 3520 has an elongate shape and includes at least one piston 3710 that is sized to be axially-inserted into at least a portion of the loading region 3622 of the loader device loading tunnel 3610. The piston 3710 can have a cross-sectional shape that substantially conforms to the cross-sectional shape of the loading region 3622 in order to facilitate insertion of the piston 3710 into the loading region 3622. In one embodiment, the piston has one or more registration grooves 3715 that conform to the shape of corresponding registration grooves 3530 (shown in FIG. 38) in the loading tunnel 3610. When the grooves 3715, 3530 are used, the piston 3710 can be inserted into the loading tunnel 3610 of the loader device 3515 by aligning and mating the grooves to one another prior to insertion. The registration grooves 3715, 3530 can be used to ensure that the piston 3710 can only be inserted into the tunnel in a predetermined manner.

Figure 41:
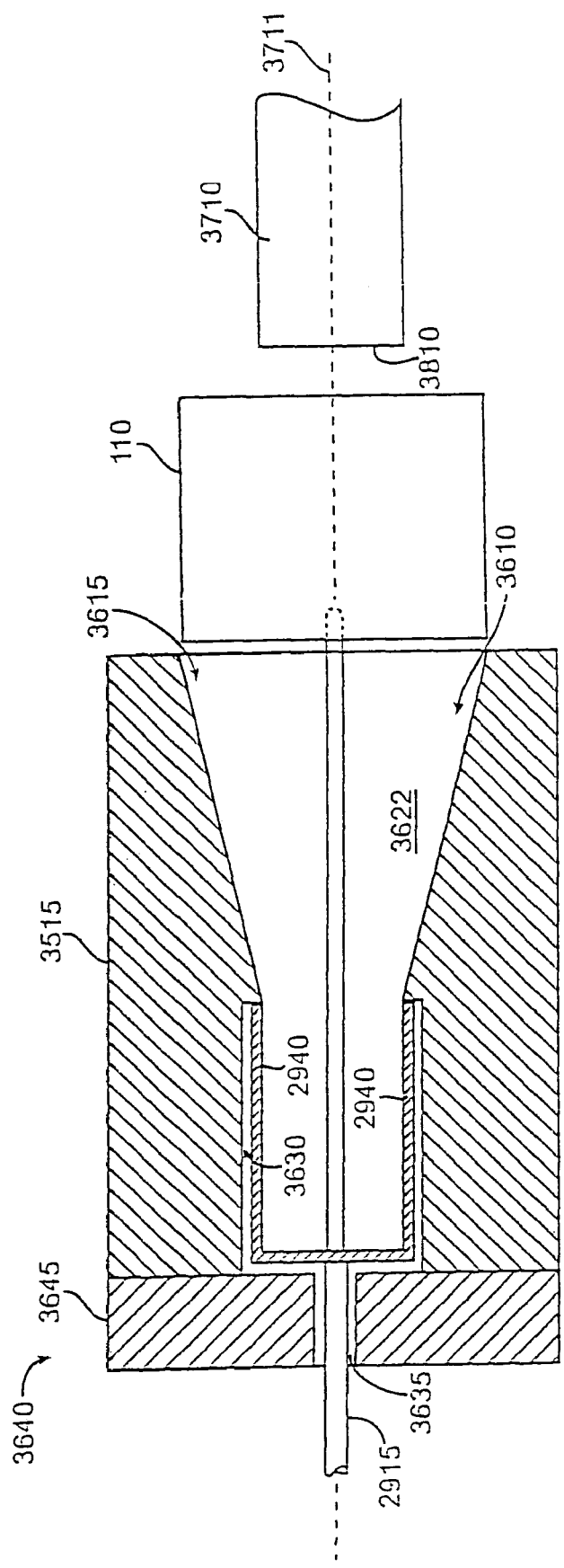
FIG. 41 shows the loader system readied for loading the flow control device into the housing of the delivery catheter.

With reference to FIGS. 41–44, the loader device 3515 is used in combination with the pusher device 3520 to compress the flow control device 110 and insert the flow control device 110 into the housing 2940 of the catheter 2915. As shown in FIG. 41, the delivery catheter 2915 is mated to the loader device 3515 such that the housing 2940 is positioned within the housing region 3630 of the loader device loading tunnel 3610 and the catheter 2915 is positioned within the catheter region 3635 of the loading tunnel 3610. When properly mated, the catheter housing 2940 is fixed in position relative to the loading region 3622 of the loading tunnel 3610. (A process and mechanism for mating the delivery catheter 2915 to the loader device 3515 is described below.) Furthermore, when the housing 2940 is positioned within the housing region 3630, the housing interior cavity is open to the loading region 3622 of the loader device 3515, such that the open end of the housing 2940 is registered with a rear edge of the loading region 3622.

With reference still to FIG. 41, after the catheter 2915 is mated with the loader device 3515, the flow control device 110 is positioned adjacent the front opening 3615 of the loading region 3622 of the loader device 3515. As shown in FIG. 41, the front opening 3615 is sufficiently large to receive the flow control device 110 therein without having to compress the size of the flow control device 110. Alternately, a slight compression of the flow control device 110 can be required to insert the flow control device 110 into the opening 3615. The pusher device 3520 is then positioned such that an end 3810 of the piston 3710 is located adjacent to the flow control device 110. The housing 2940, flow control device 110 and the piston 3710 are preferably all axially aligned to a common longitudinal axis 3711 prior to loading the flow control device 110 into the housing 2940. However, even if these components are not all axially aligned, the structure of the loader device 3515 will ensure that the components properly align during the loading process.

Figure 42:
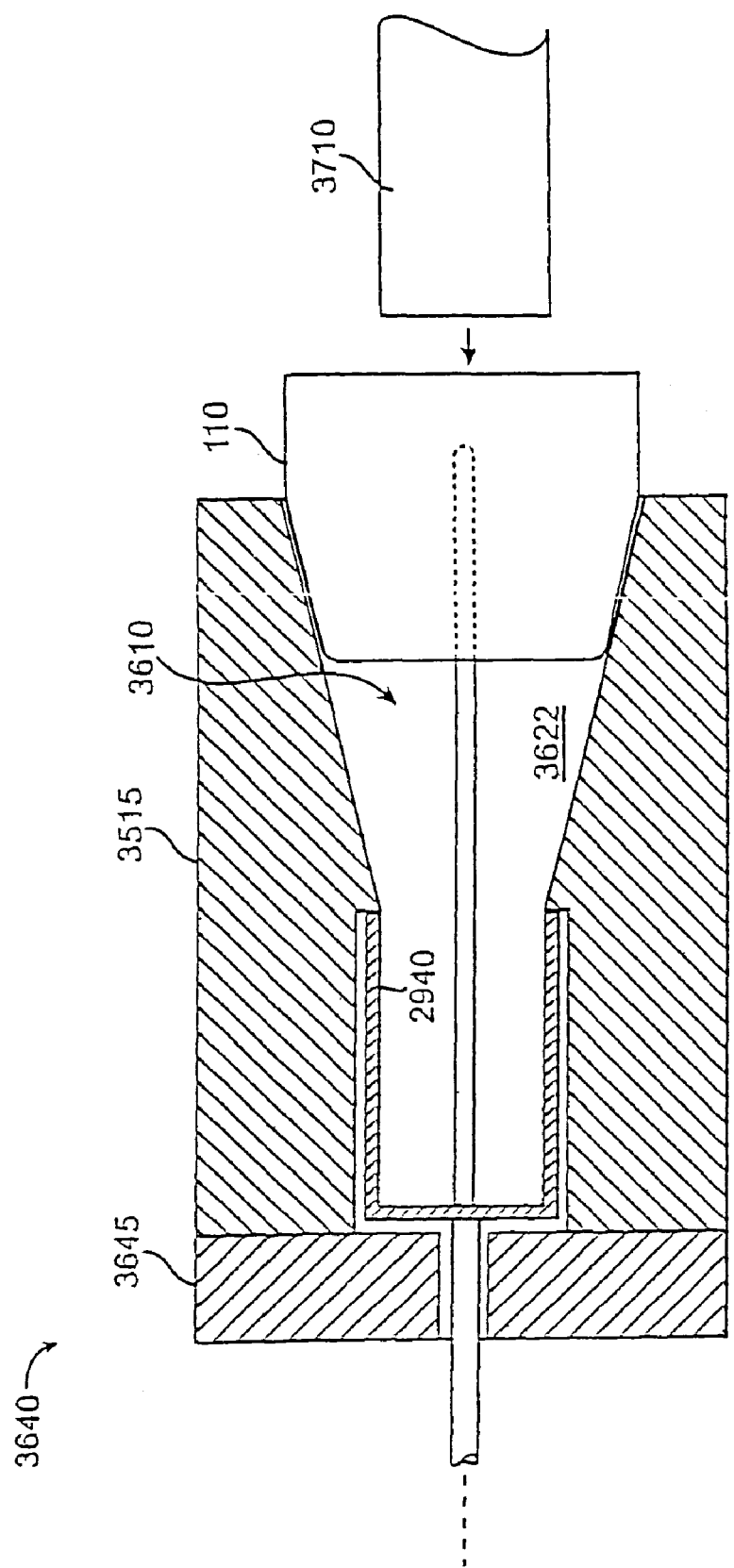
FIG. 42 shows the loader system being used to compress the flow control device during loading of the flow control device into the housing of the delivery catheter.

With reference now to FIG. 42, the piston 3710 of the pusher device 3520 is then used to push the flow control device into the loading region 3622 of the loading tunnel 3610 through the front opening 3615 in the tunnel. In this manner, the flow control device 110 moves through the loading tunnel 3610 toward the housing 2940. As this happens, the funnel-shape of the loading region 3622 will cause the flow control device 110 to be gradually compressed such that the diameter of the flow control device is gradually reduced as the flow control device 110 moves toward the housing 2940. The walls of the loading tunnel 3610 provide an equally balanced compressive force around the entire circumference of the flow control device 110 as the flow control device is pushed through the loading tunnel 3610. This reduces the likelihood of deforming the flow control device during compression.

Figure 43:
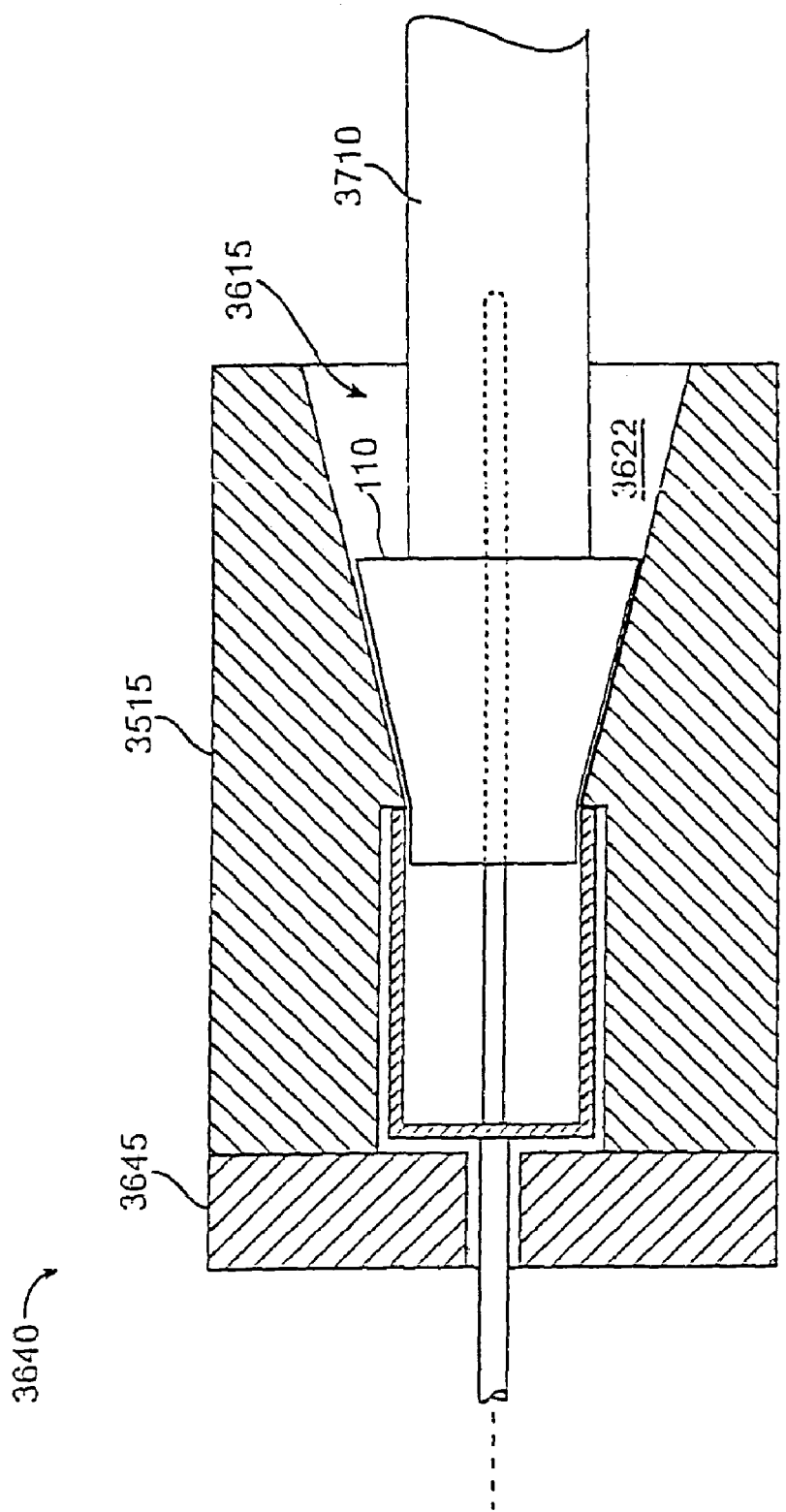
FIG. 43 shows the loader system being used to compress the flow control device during insertion of the flow control device into the housing of the delivery catheter.

As shown in FIG. 43, as the flow control device is pushed toward the housing 2940, the flow control device 110 will eventually be compressed to a size that permits the flow control device to be pushed into the housing 2940. In one embodiment, the loading region 3622 of the loading tunnel 3610 reduces to a size that is smaller than the opening of the housing 2940 so that the flow control device 110 can slide easily into the housing 2940 without any snags. Alternately, the opening in the housing 2940 can be substantially equal to the smallest size of the loading region 3622.

Figure 44:
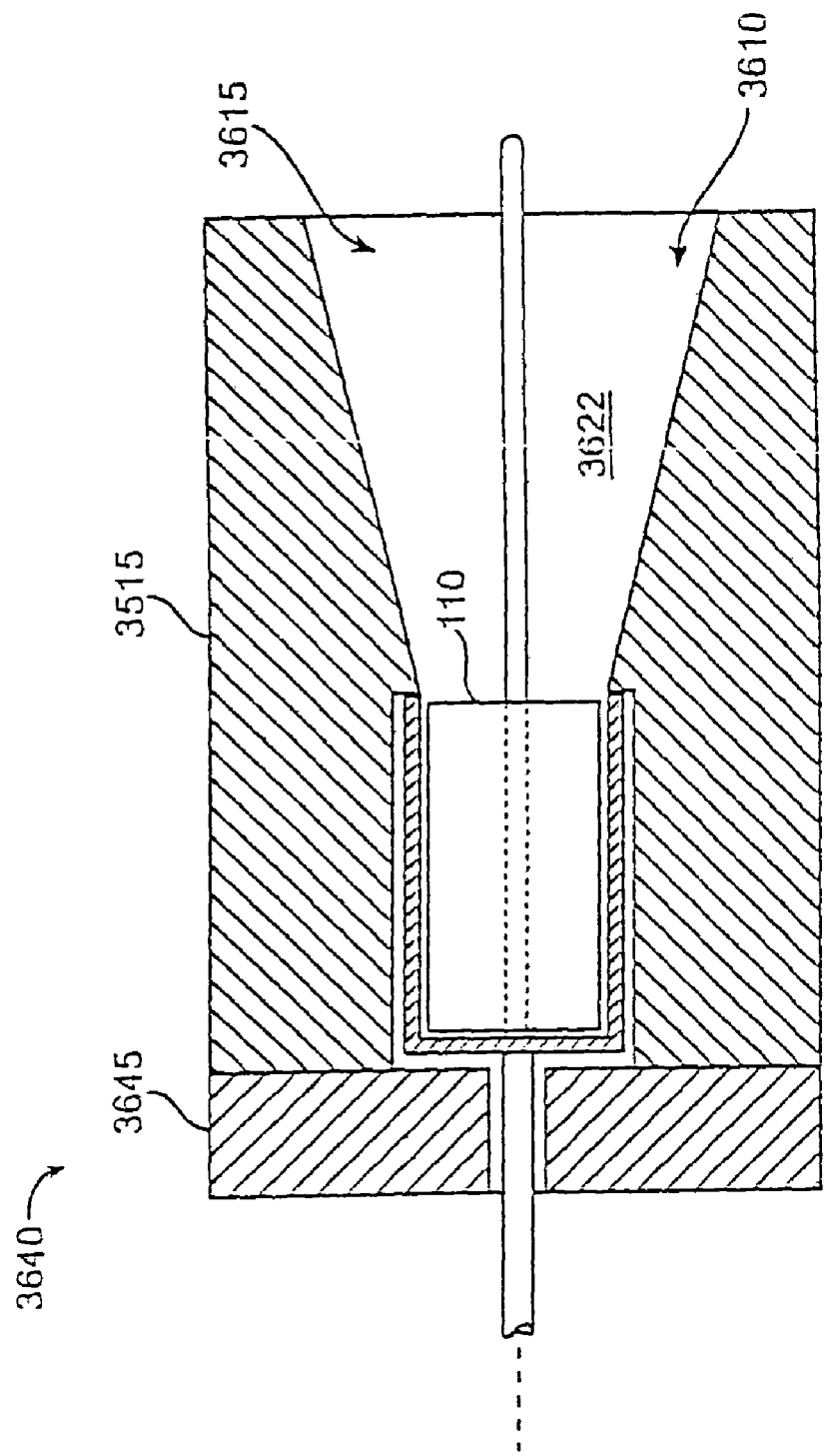
FIG. 44 shows the loader system with the flow control device fully loaded into the housing of the delivery catheter.
Figure 45:
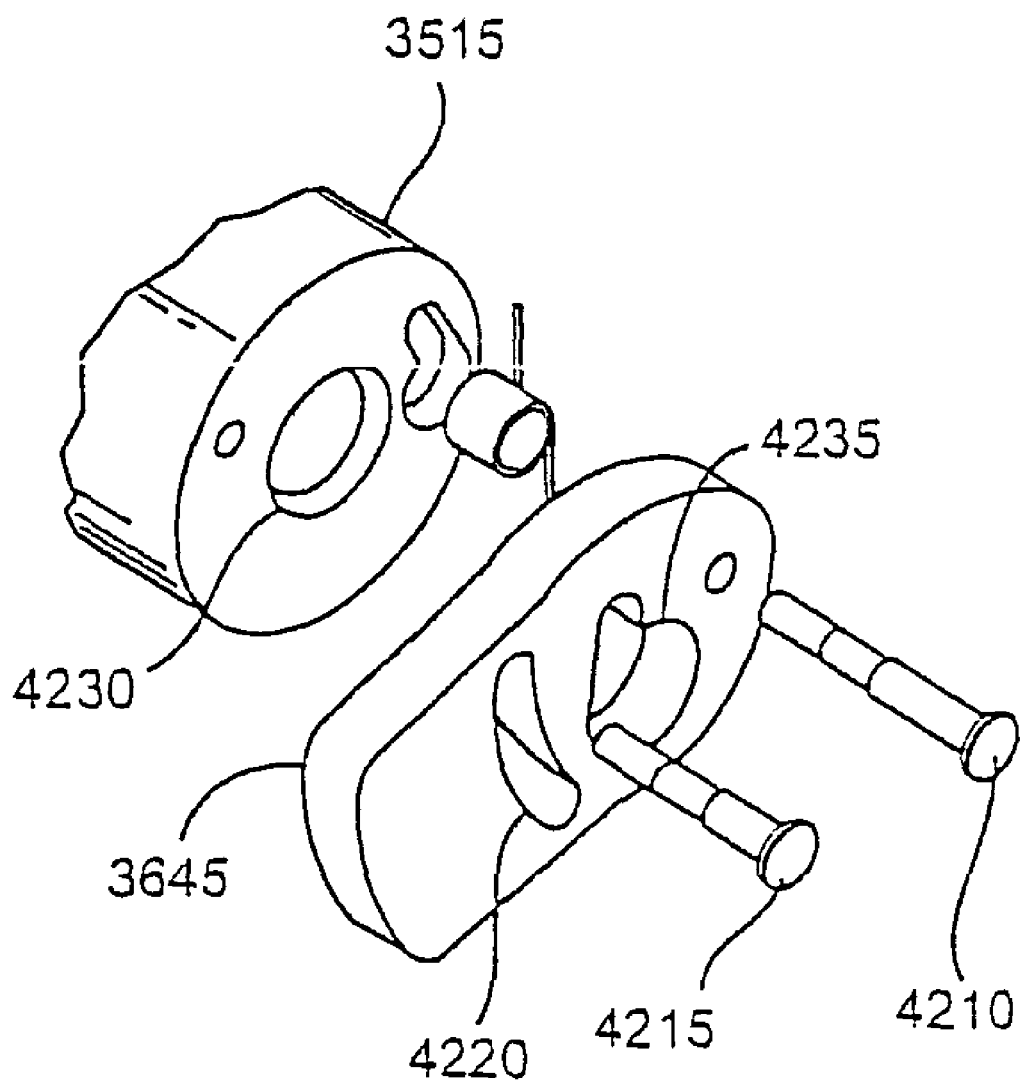
FIG. 45 shows an exploded, perspective rear view of the loader device of the loader system.

As shown in FIG. 44, the pusher device 3520 continues to push the flow control device 110 into the loader device 3515 until the entire flow control device 110 is located inside the housing 2940. The pusher device 3520 can then be removed from the loader device 3515. The catheter 2915 and the housing 2940 (which now contains the loaded flow control device 110) can then also be removed from the loader device 3515.

As mentioned above, the loader device 3515 includes a locking mechanism 3640 that is used to lock and position the catheter 2915 and catheter housing 2940 relative to loader device 3515 during loading of the flow control device 110 into the housing 2940. An exemplary locking mechanism 3640 is now described with reference to FIGS. 45–48, although it should be appreciated that other types of locking mechanisms and other locking procedures could be used to lock and position the catheter 2915 and catheter housing 2940 relative to loader device 3515 during loading.

As mentioned, the locking mechanism can comprise a door 3645 that can be moved to facilitate insertion of the catheter housing 2940 into the loader device 3515. Such a locking mechanism 3640 is described in more detail with reference to FIG. 45, which shows an exploded, rear, perspective view of the loading member 3515. The locking mechanism 3640 comprises a door 3645 that is pivotably-attached to a rear surface of the loader device 3515 by a first pin 4210. A second pin 4215 also attaches the door 3645 to the loader device 3515. The second pin extends through an arc-shaped opening 4220 in the door 3645 to provide a range of pivotable movement for the door 3645 relative to the loader device 3515, as described more fully below. The rear surface of the loader device 3515 has an opening 4230 that opens into the housing region 3630 of the loading tunnel 3610 in the loader device 3515. When mounted on the loader device 3515, the door 3645 can partially block the opening 4230 or can leave the opening unblocked, depending on the position of the door 3645. The door 3645 includes an irregular shaped entry port 4235 through which the catheter 2915 and catheter housing 2940 can be inserted into the opening 4230.

Figure 46:
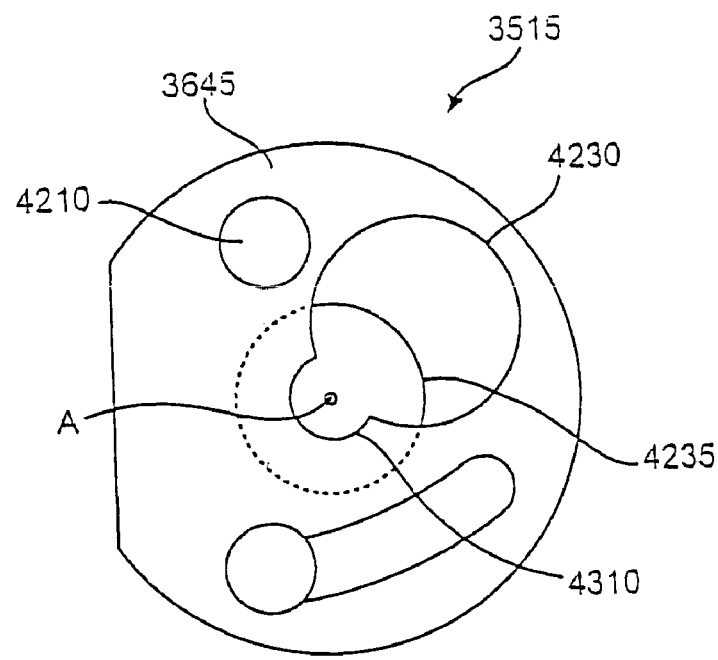
FIG. 46 shows a plan, rear view of the loader device of the loader system with a delivery door in a closed position.
Figure 47:
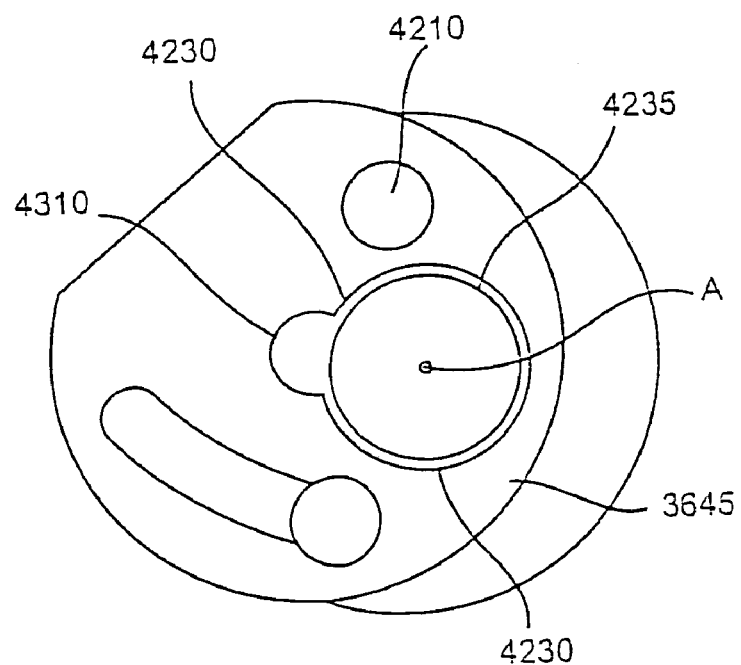
FIG. 47 shows a plan, rear view of the loader device of the loader system with a delivery door in an open position.
Figure 48A:
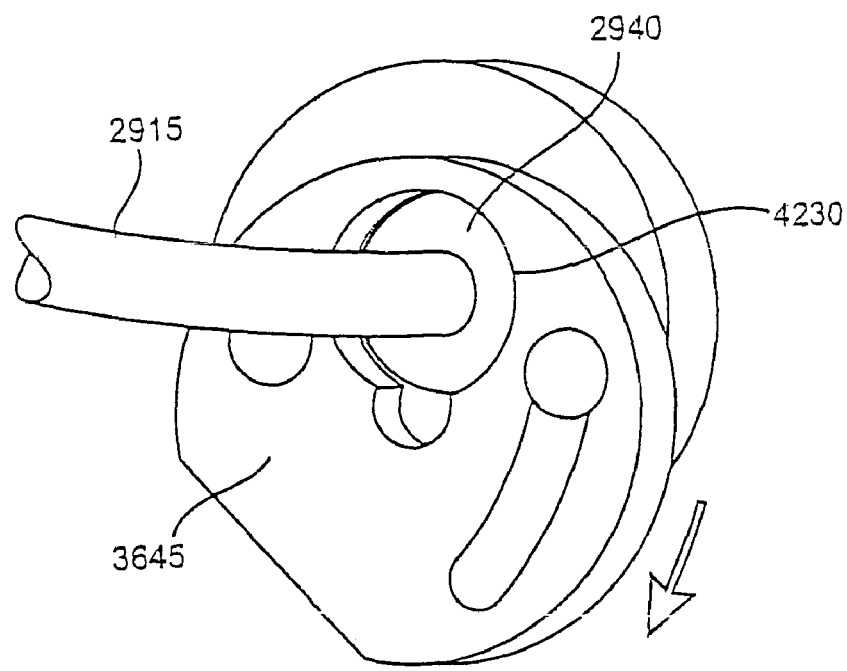
FIG. 48A shows a perspective, rear view of the loader device of the loader system with the delivery door in an open position and the catheter housing inserted into the loader device.
Figure 48B:
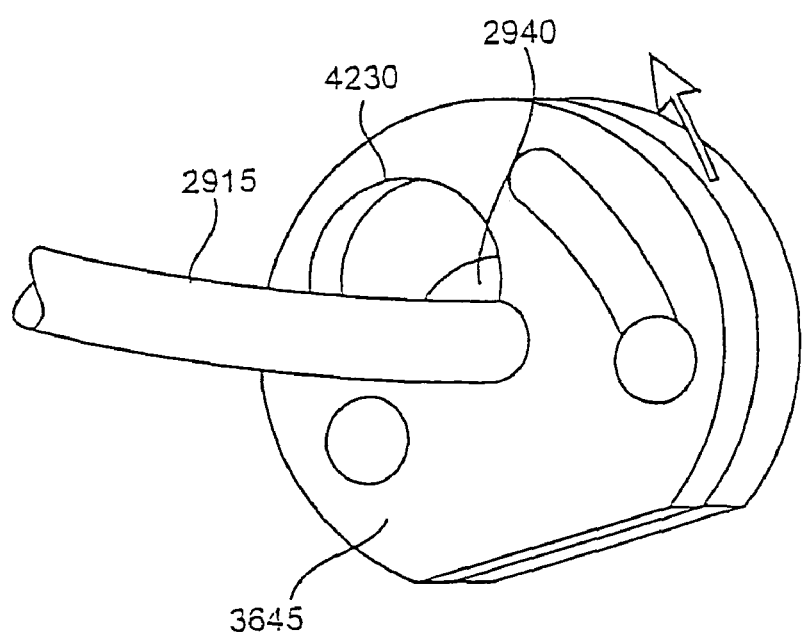
FIG. 48B shows a perspective, rear view of the loader device of the loader system with the delivery door in a closed position and the catheter housing mated with the loader device.

FIG. 46 shows a rear view of the loader device 3515 with the door 3645 in a default, closed state. When in the closed state, the door partially occludes the opening 4230. The entry port 4235 includes a catheter region 4310 that is sized to receive the outer member 2918 of the catheter 2915. The catheter region 4310 is aligned with a central axis A of the opening 4230 in the loader device 3515 when the door 3645 is closed. As shown in FIG. 47, the door 3645 can be moved to an open position by rotating the door 3645 about an axis defined by the first pin 4210. When the door is in the open position, the entry port 4230 is positioned such that a large portion of the entry port 4235 is aligned with the opening 4230 in the loader device 3515 so that the opening 4230 is unblocked. This allows the housing 2940 of the catheter 2915 to be inserted into the housing region 3630 through the aligned entry port 4235 and opening 4230 while the door 3645 is in the open position, as shown in FIG. 48A. The door 3645 can then be released and returned to the closed position, such that the door 3645 partially blocks the opening 4230 and thereby retains the housing 2940 within the housing region 3630, as shown in FIG. 48B. The door 3645 can be spring-loaded so that it is biased toward the closed position.

Figure 49:
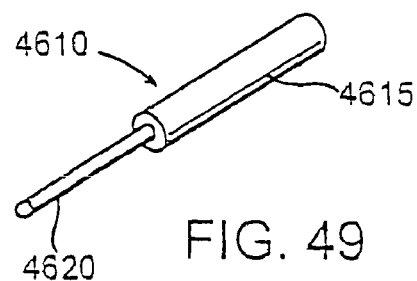
FIG. 49 shows a perspective view of a loading tube of the loader system.
Figure 50A:
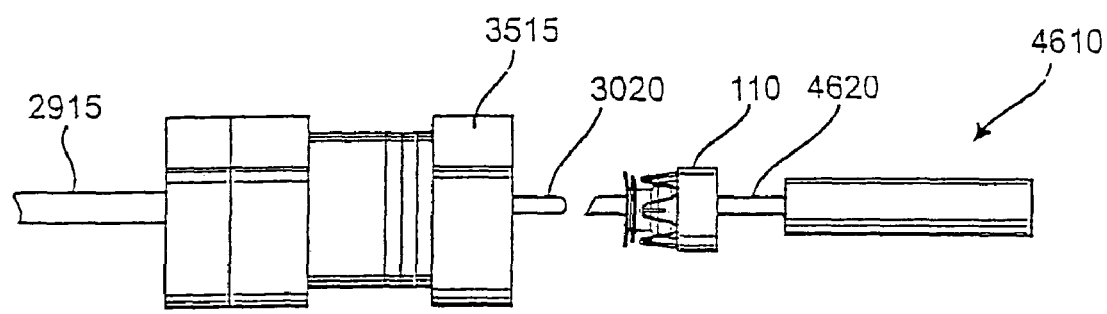
FIG. 50A shows the loading tube being used to initially insert the flow control device into the loader device.

As discussed above, during loading of the flow control device 110, the flow control device 110 is initially positioned within the loading tunnel 3610 of the loader device 3515. The initial positioning of the flow control device 110 can be facilitated through the use of a loading tube 4610, shown in FIG. 49, which is comprised of a handle 4615 and an elongate tube region 4620 having a diameter that can fit within the internal lumen of the flow control device 110. The elongate tube region 4620 can be hollow so as to define an interior lumen that can fit over the front nose region 3020 (shown in FIGS. 33 and 50A) of the catheter 2915. The loading tube 4610 is used as follows: the flow control device 110 is first mounted on the tube region 4620 by inserting the tube region 4620 into the interior lumen of the flow control device 110, such as is shown in FIG. 50A. The tube region 4620 can optionally have an outer diameter that is dimensioned such that the tube region fits somewhat snug within the interior lumen of the flow control device 110 so that the flow control device 110 is retained on the tube region 4620 through a press-fit.

Figure 50B:
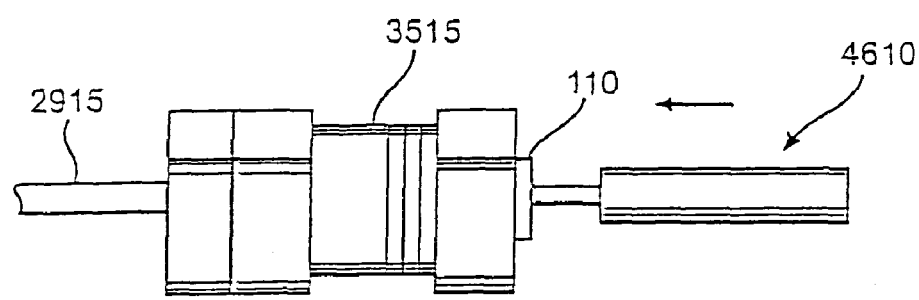
FIG. 50B shows the loading tube being used to initially insert the flow control device into the loader device.

As shown in FIG. 50B, the loading tube 4610 is then used to insert the flow control device 110 over the tip region 3020 and into the tunnel of the loader device 3515. The handle 4615 can be grasped by a user to easily manipulate the positioning of the flow control device 110 relative to the loader device 3515. The loading tube 4610 can then be removed from the flow control device 110 while keeping the flow control device 110 mounted in the loader device 3515 in an initial position. The pusher device 3715 is then used to push the flow control device 110 entirely into the loader device 3515, as was described above with reference to FIGS. 41–44.

Figure 51:
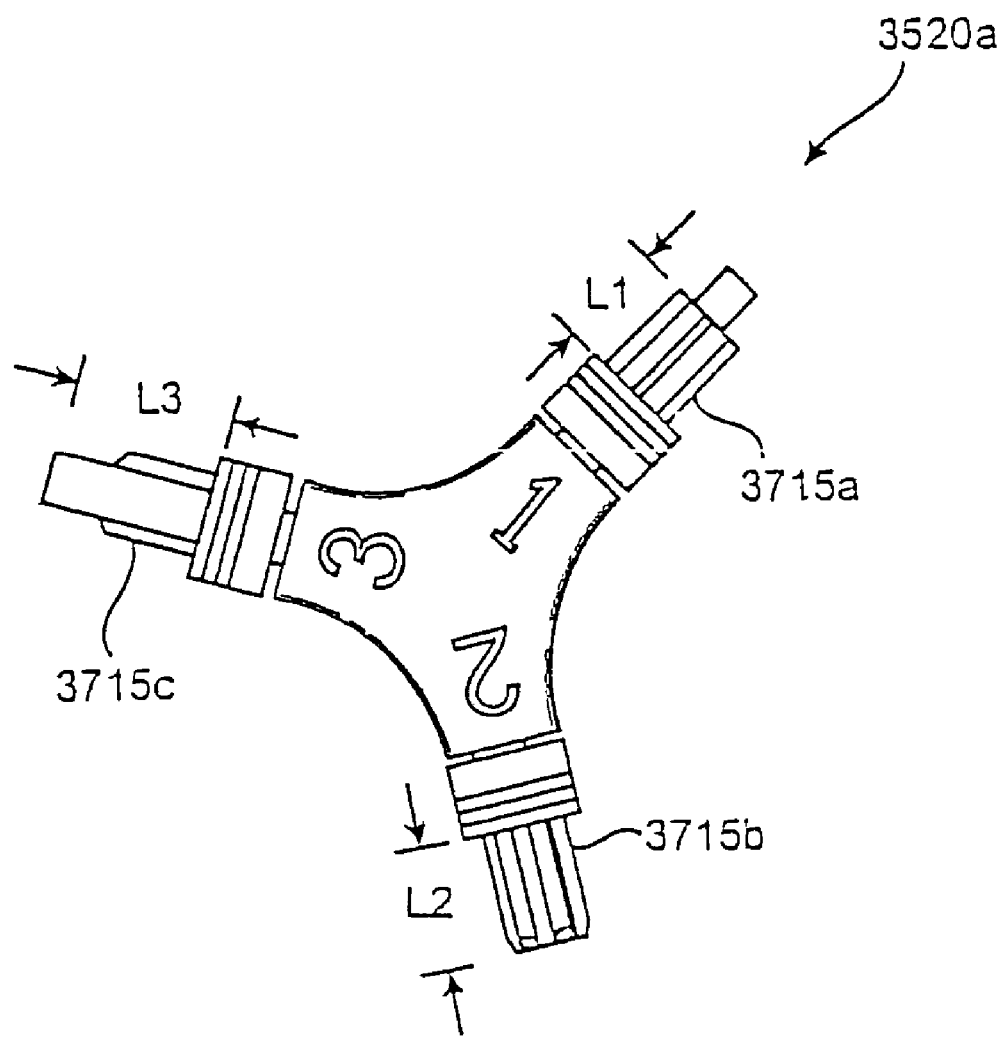
FIG. 51 shows another embodiment of a pusher device.
Figure 52A:
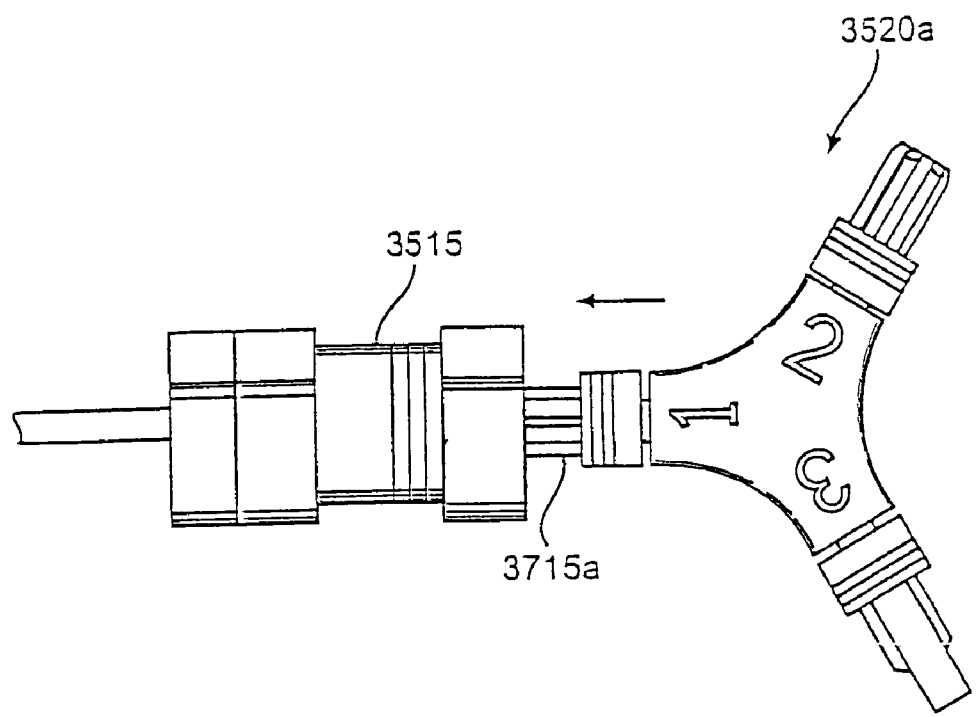
FIG. 52A shows the pusher device of FIG. 51 initially inserted into the loader device.
Figure 52B:
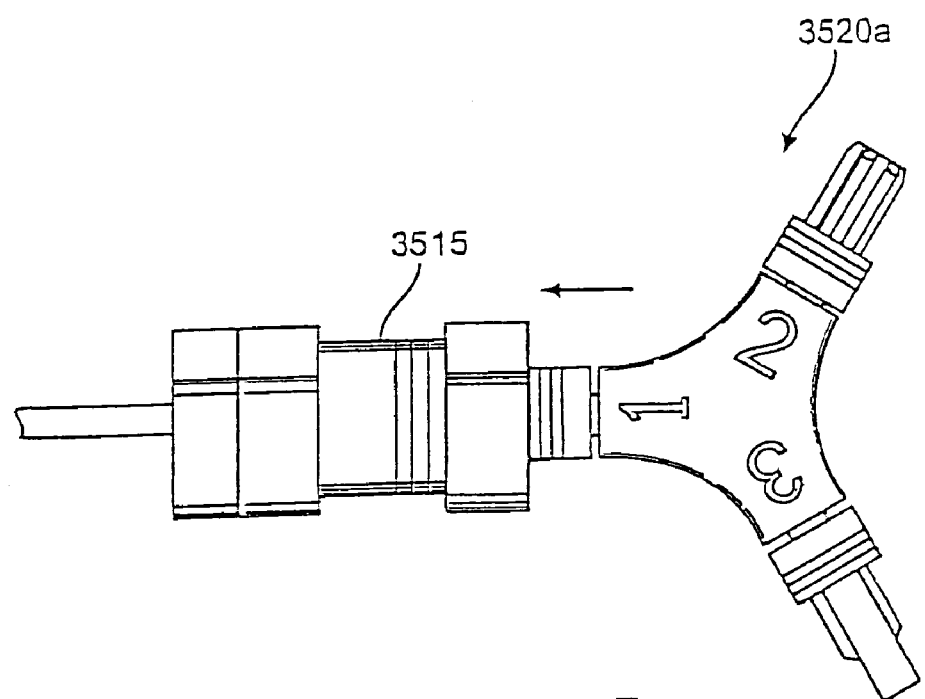
FIG. 52B shows the pusher device of FIG. 51 fully inserted into the loader device.

FIG. 51 shows another embodiment of the pusher device 3520, which is referred to using the reference numeral 3520a. The pusher device 3520a includes three separate pistons 3715a, 3715b, 3715c that each extend radially outward from a center of the pusher device 3520 in a pinwheel fashion. Each of the pistons 3715a, 3715b, 3715c has a different length L. In particular, the piston 3710a has a length L1, the piston 3615b has a length L2, and the piston 3710c has a length L3. The pistons 3715a,b,c can be used in series to successively push the flow control device 110 to increasingly greater depths into the tunnel of the loader device 110. For example, the piston 3710a can be used first to push the flow control device 110 to a first depth L1, as shown in FIGS. 52A and 52B. The piston 3710b can be used next to push the flow control device 110 to a second depth deeper than the first depth. The third piston 3710c can finally be used to push the flow control device 110 entirely into the housing. The pistons 3710a,b,c can also have different diameters from one another. The varying diameters of the pistons can correspond to the varying diameter of the loading tunnel in which the piston will be inserted. For example, the piston with the shortest length can have a larger diameter, as such as piston will be inserted into the region of the loading tunnel that has a relatively large diameter. A large diameter will prevent the piston from being inserted to a location of smaller diameter in the tunnel. The piston with the longest length can have a smaller diameter, as such a piston will be inserted deeper into the loading tunnel, where the diameter is smaller. In this way, the piston length and diameter can be optimized for insertion into a particular location of the loading tunnel. In addition, the use of a pusher device 3520 with pistons of varying length can reduce the likelihood of pushing the flow control device into the loader device 3515 at too fast of a rate.

Figures 53, 54:
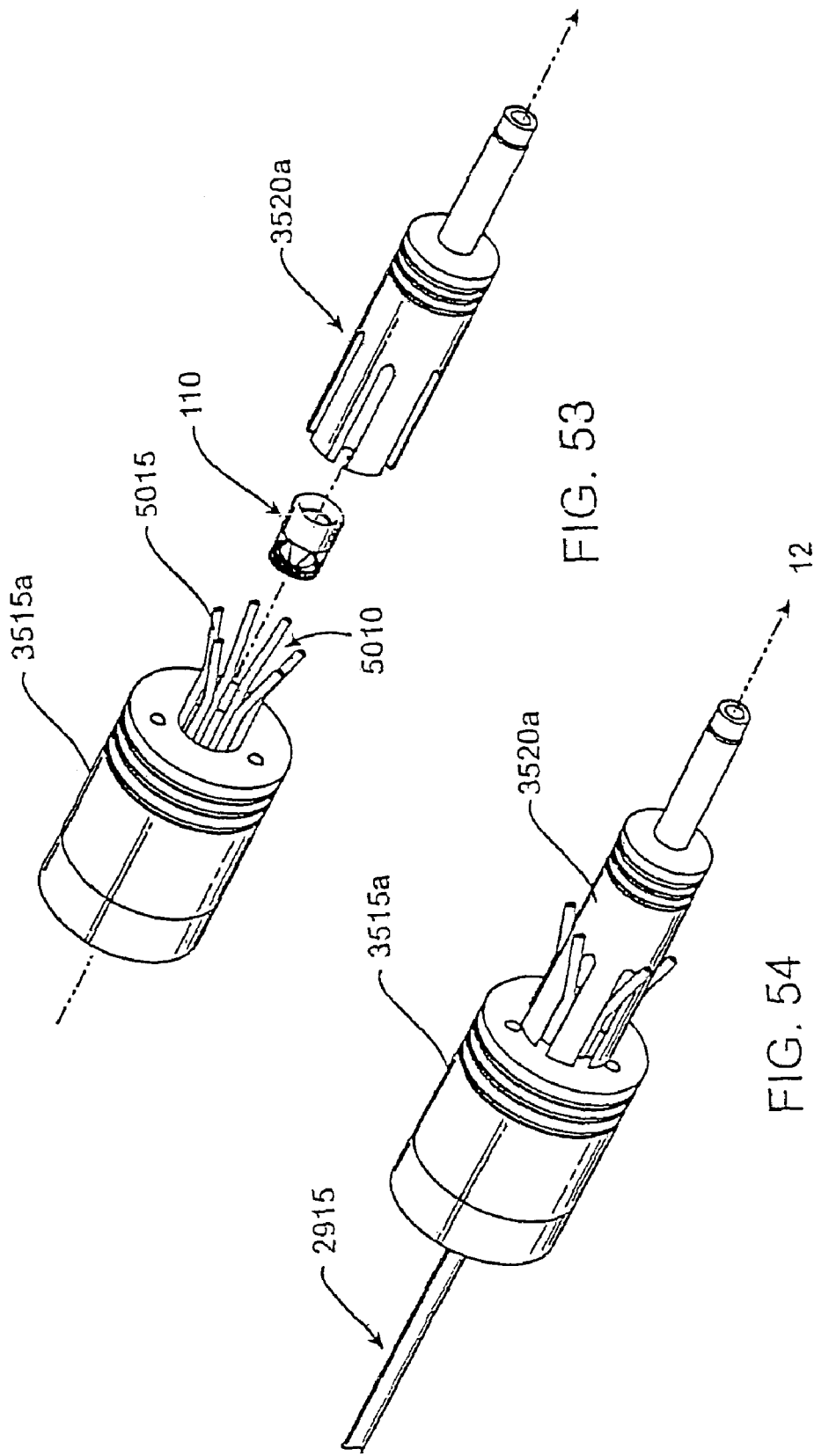
FIG. 53 shows an exploded, perspective another embodiment of the loader system.
FIG. 54 shows an exploded, perspective another embodiment of the loader system with the pusher device inserted into the loader device.

FIG. 53 shows another embodiment of a loader device, which is referred to as loader device 3515a, as well as another embodiment of a corresponding pusher device 3520, which is referred to using the reference numeral 3520a. The loader device 3515a has plurality of prongs 5015 that are arranged in an annular fashion so as to define a funnel-shaped loading region 5010. Thus, the loading region 5010 is defined by a series of prongs, rather than an internal tunnel, as in the embodiment of the loader device shown in FIG. 38. As shown in FIG. 54, the pusher device 3520a can be inserted into the loading region 5010 of the loader device 3515a to load the flow control device 110 into the housing of the catheter 2915 when the catheter 2915 is mated with the loader device 3515a. It should be appreciated that other structures could be used to define the loading region of the loader device. The pusher device 3520a has a piston with ridges that are dimensioned to mate with the prongs 5015.

Figure 55:
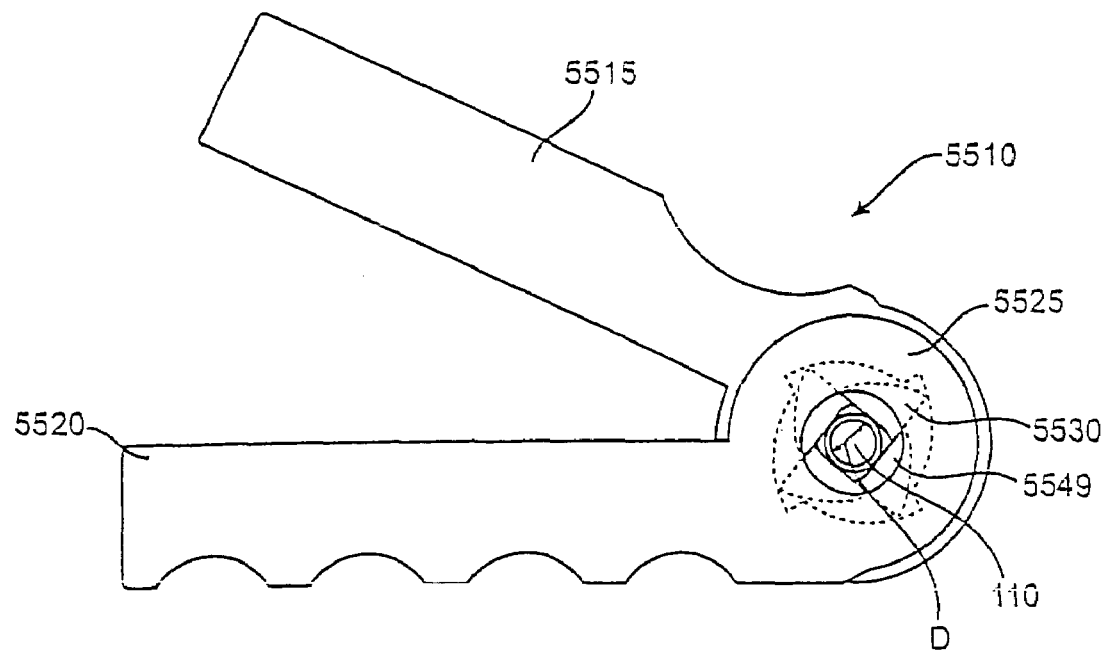
FIG. 55 shows a front, plan view of another embodiment of a loader device.
Figure 56:
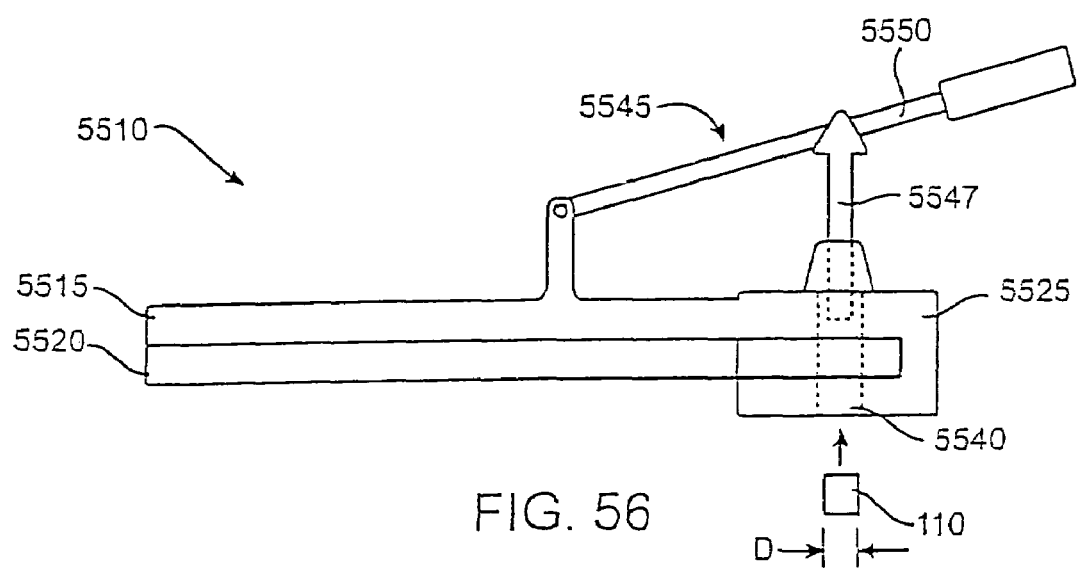
FIG. 56 shows a side, plan view of the loader device of FIG. 55.

FIGS. 55–58 show another embodiment of a loader device, which is referred to as loader device 5510. FIG. 55 shows a front, plan view of the loader device 5510 in an open state and FIG. 56 shows a side, plan view of the 20 loader device 5510 in an open state. The loader device 5510 includes a first handle 5515 and a second handle 5520. The handles 5515, 5520 can be moved with respect to one another in a scissor fashion. The handles 5515, 5520 are attached to a loader head 5525. A compression mechanism 5530 is contained in the loader head 5525. The compression mechanism 5530 comprises a series of cams 5549 that are mechanically-coupled to the handles 5515, 5520, as described in more detail below.

Figure 57:
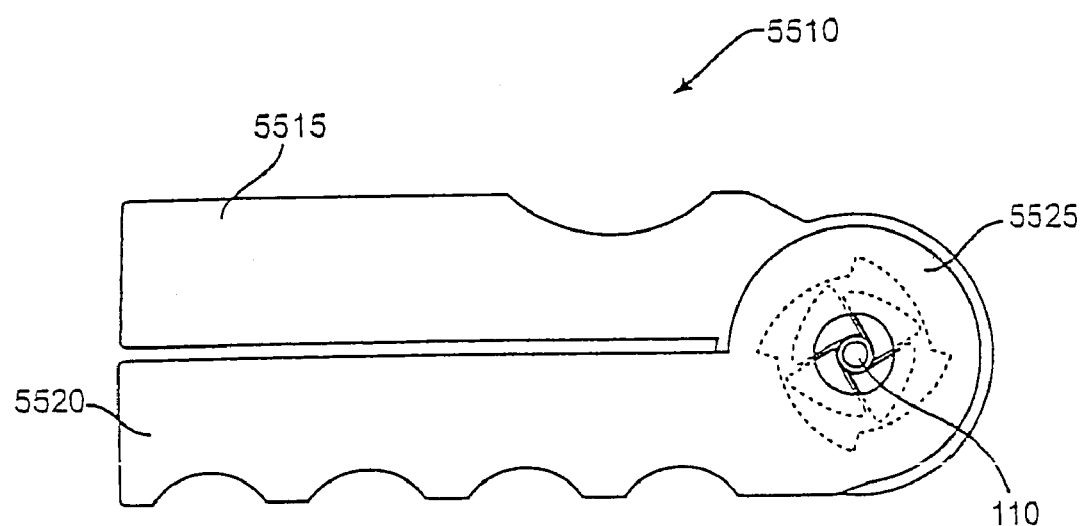
FIG. 57 shows a front, plan view of the loader device of FIG. 55 in a closed state.

The compression mechanism 5530 defines a loading tunnel 5540 that extends through the loader head 5525. The cams 5549 have opposed surfaces that define the shape of the loading tunnel 5540. In the illustrated embodiment, there are four cams 5549 that define a rectangular-shaped tunnel looking through the tunnel when the device in the open state. As described below, when the handles 5515, 5520 are closed, the cams 5549 reposition so that the loading tunnel takes on a circular or cylindrical shape, as shown in FIG. 57. In the open state, the loading tunnel 5540 can accept an uncompressed flow control device 110 that has a diameter D. In alternative embodiments, the compression mechanism 5530 may contain three, five or more cams 5549.

With reference to FIG. 56, the loader device 5510 has a piston mechanism 5545 that includes a piston 5547 that is slidably positioned in the loading tunnel 5540. The piston 5547 is attached at an upper end to a lever 5550 that can be used to slide the piston 5547 through the loading tunnel 5540. In an alternative embodiment, the piston 5547 is advanced manually, without the use of the lever 5550, by pushing the piston 5547 into the loading tunnel 5540.

As mentioned, the first handle 5515 and the second handle 5520 are movable with respect to one another in a scissor fashion. In this regard, FIG. 55 shows the handles 5515, 5520 in an open state. FIG. 57 shows the handles 5515, 5520 in a closed state. The movement of the handles 5515, 5520 with respect to one another actuates the compression mechanism 5530 by causing the cams 5549 of the compression mechanism 5530 to change position and thereby change the size of the loading tunnel 5540. More specifically, the diameter D of a flow control device 110 inserted into the loading tunnel 5540 is larger when the handles 5515, 5520 are open (as shown in FIG. 55) and smaller when the handles 5515, 5520 are closed (as shown in FIG. 57). When the handles 5515, 5520 are open, the size of the loading tunnel 5540 is sufficiently large to receive a flow control device 110 of diameter D in the uncompressed state.

Thus, as shown in FIG. 56, the flow control device 110 (represented schematically by a box 110) can be inserted into the loading tunnel 5540. Once the flow control device 110 is inserted into the loading tunnel 5540, the handles 5515, 5520 can be closed, which will cause the size of the loading tunnel 5540 to decrease. The decrease in the size of the loading tunnel 5540 will then compress the diameter of the flow control device 110, which is contained in the loading tunnel 5540. The flow control device 110 is compressed to a size that will permit the flow control device 110 to fit within the housing 2940 of the catheter delivery system 2910 (shown in FIG. 32). When the handles 5515, 5520 are closed, the loading tunnel 5540 is at its minimum size. The cams 5549 have a shape such that when the loading tunnel 5540 is at its minimum size, the loading tunnel 5540 preferably forms a cylinder. The loading tunnel 5540 may also form other shapes when the device is in the closed state, however a cylindrical shape is preferable.

Figure 58:
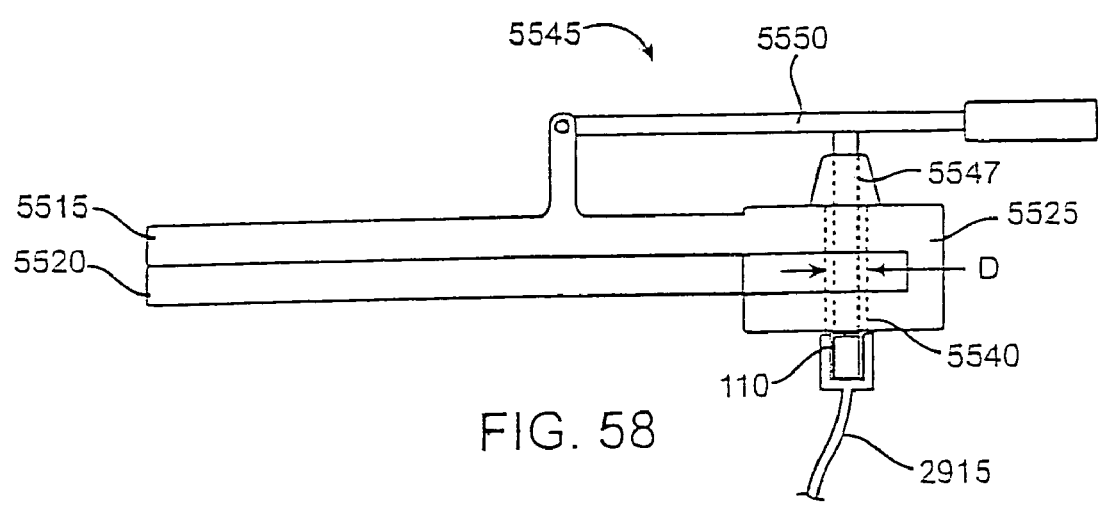
FIG. 58 shows a side, plan view of the loader device of FIG. 55.

With reference to FIGS. 56 and 58, the piston 5547 can then be used to push the flow control device 110 into the housing 2940. As mentioned, the lever 5550 can be used to slidably move the piston 5547 through the loading tunnel 5540. As shown in FIG. 56, when the lever 5550 is in a raised position, the 10 piston 5547 is only partially inserted into the loading tunnel 5540. As shown in FIG. 58, the lever 5550 can be moved toward the loader head 5525 to cause the piston 5547 to slide deeper into the loading tunnel 5540 to a depth such that the piston 5547 will push the flow control device 110 out of the loading tunnel 5540. The catheter housing 2940 can be placed adjacent to the loading tunnel 5540 so that the housing 2940 can receive the flow control device 110 as it is pushed out of the loading tunnel 5540 by the piston 5547. Although FIGS. 55–58 show the piston mechanism 5545 attached to the loader 5510, it should be appreciated that the piston mechanism 5545 could be removably attached or a separate device altogether.

Both the second handle 5520 and the lever 5550 for operating the piston 5547 are capable of being attached to one or more stops that allow the user to limit the amount of compression of the loading tunnel 5540 or to limit the distance the piston 5547 moves into the loading tunnel 5540. In this manner, the loader 5510 can be set to compress a flow control device 110 to a particular size (where the stop corresponds to a desired diameter) and insertion to a particular length (where the stop corresponds to a movement of the piston 5547). It should be appreciated that the loader 5510 can also be configured such that the second handle 5520 can actuate both the compression mechanics as well as the piston 5547 (or a piston substitute), such that when the second handle 5520 is closed to a certain point, the flow control device 110 will be fully compressed. Continuing to actuate the handle 5520 will cause the flow control device 110 to be loaded into the housing 2940 of the catheter 2915.

The loader 5510 advantageously allows a user to compress and load the 10 flow control device into the housing

2940 using a single hand. The user can load the flow control device 110 into the loading tunnel 5540 of the loader 5510 and then use one hand to close the handles 5515, 5520, which will cause the loader 5510 to compress the flow control device 110 to a size that will fit within the housing 2940. The user can then actuate the piston mechanism 5545 to eject 15 the flow control device 110 out of the loading tunnel 5540 and into the housing 2940.

Leaf Petal Style Flow Control Devices

Figure 59:
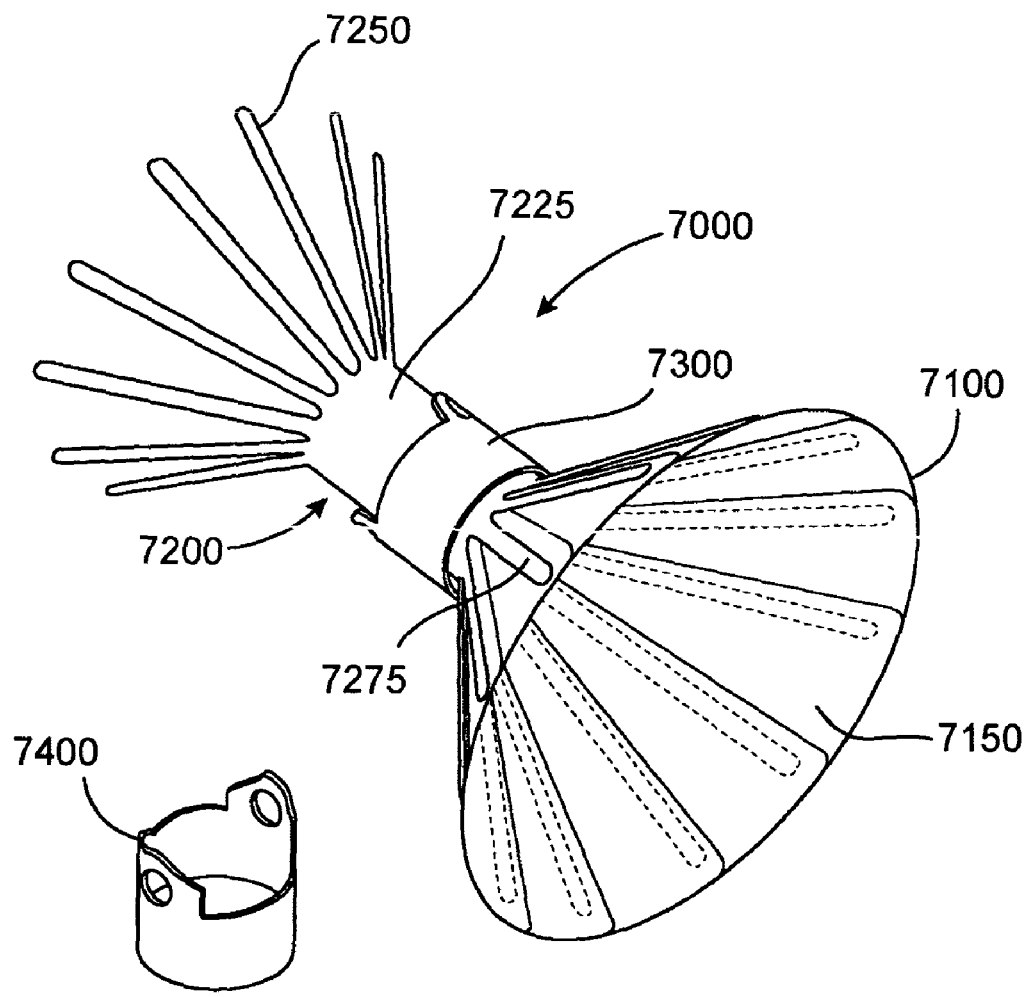
FIG. 59 shows a perspective view of a flow control device having a segmented valve/seal component.

FIG. 59 depicts a leaf petal style flow control device 7000. The leaf petal style flow control device 7000 is a one-way valve isolation device, which includes a combined valve and sealing component 7100 that is conical or cone-like in shape as shown in FIG. 59. The valve and sealing component 7100 shown in FIG. 59 is generally conical or cone-like in shape, but other shapes may also be used. The valve/seal component 7100 is formed of a plurality of segments 7150 that overlap like the petals of a flower. Each segment 7150 has a radial edge that is configured to overlap an adjacent overlapping segment 7150. The radial edge can be connected or connected to the adjacent overlapping segment 7150.

The flow control device 7000 also includes a frame 7200 that is used to position the device 7000 in a bronchial lumen and to support the valve/seal component 7100. The frame 7200 includes a central core 7225. A first set of outwardly biased deployable arms 7250 extend distally from the core 7225. A second set of deployable arms 7275 extends proximally from the core 7225. The second set of deployable arms 7275 can also be outwardly biased. The leaf petal style flow control device 7000 also may include a frame retainer sleeve 7300 that is used to retain outwardly biased deployable arms 7250 and that can be used to radially retract the deployable arms 7250. The frame retainer sleeve 7300 is mounted coaxially over the frame 7200 and can slide along the length of the frame 7200. The flow control device 7000 can also include a second sleeve 7400 (shown in a disengaged state for clarity) that can be used to retain deployable arms 7275.

The isolation device 7000 is implanted in a bronchial lumen such that the valve/seal component 7100 engaged the bronchial lumen wall. Air and liquid can pass between the valve/seal component 7100 and the bronchial lumen wall in the exhalation direction, but when flow is reversed during inhalation, the valve/seal component 7100 is compressed against the bronchial lumen wall, the segments 7150 are pressed against each other and flow of gas or liquid in the inhalation direction is prevented.

Figure 60:
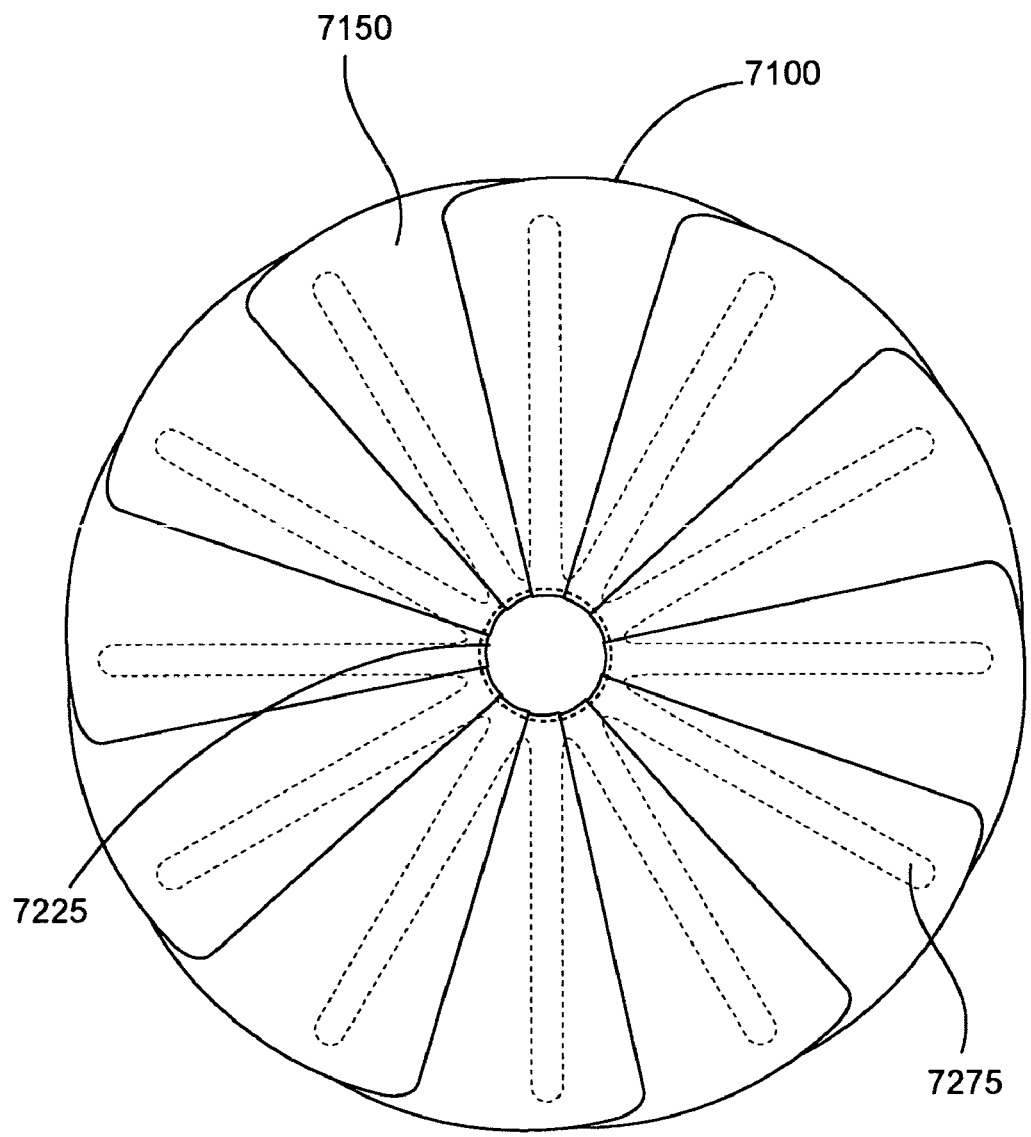
FIG. 60 is a front plan view of the valve/seal component of the flow control device depicted in FIG. 59.

Turning to FIG. 60, the valve/seal component 7100 is shown in an expanded state. The valve/seal component 7100 can be constructed from a flexible material such as, for example, molded silicone. Many other flexible materials, such as urethane, can also be used. The valve/seal component 7100 is formed of a plurality of segments 7150 that overlap like the petals of a flower. FIG. 60 shows twelve overlapping segments 7150, but the valve/seal component 7100 can be formed of two, three, four, five, six, seven, eight, nine, ten, eleven, twelve or more overlapping segments 7150 to accommodate various sized bronchial lumens and to suit varying needs. With a valve/seal component 7100 formed of individual overlapping segments 7150, the segments can slide relative to one another when compressed to smaller diameters, and create a seal without wrinkles. The device 7000 will still vent fluid easily in the exhalation direction; however, the overlapping segments 7150 will seal against each other and against the bronchial lumen wall during inhalation, thus preventing fluid from flowing past the device 7000 in the inhalation direction. This sealing effect can be maintained across a range of bronchial lumen diameters.

Figure 60B:
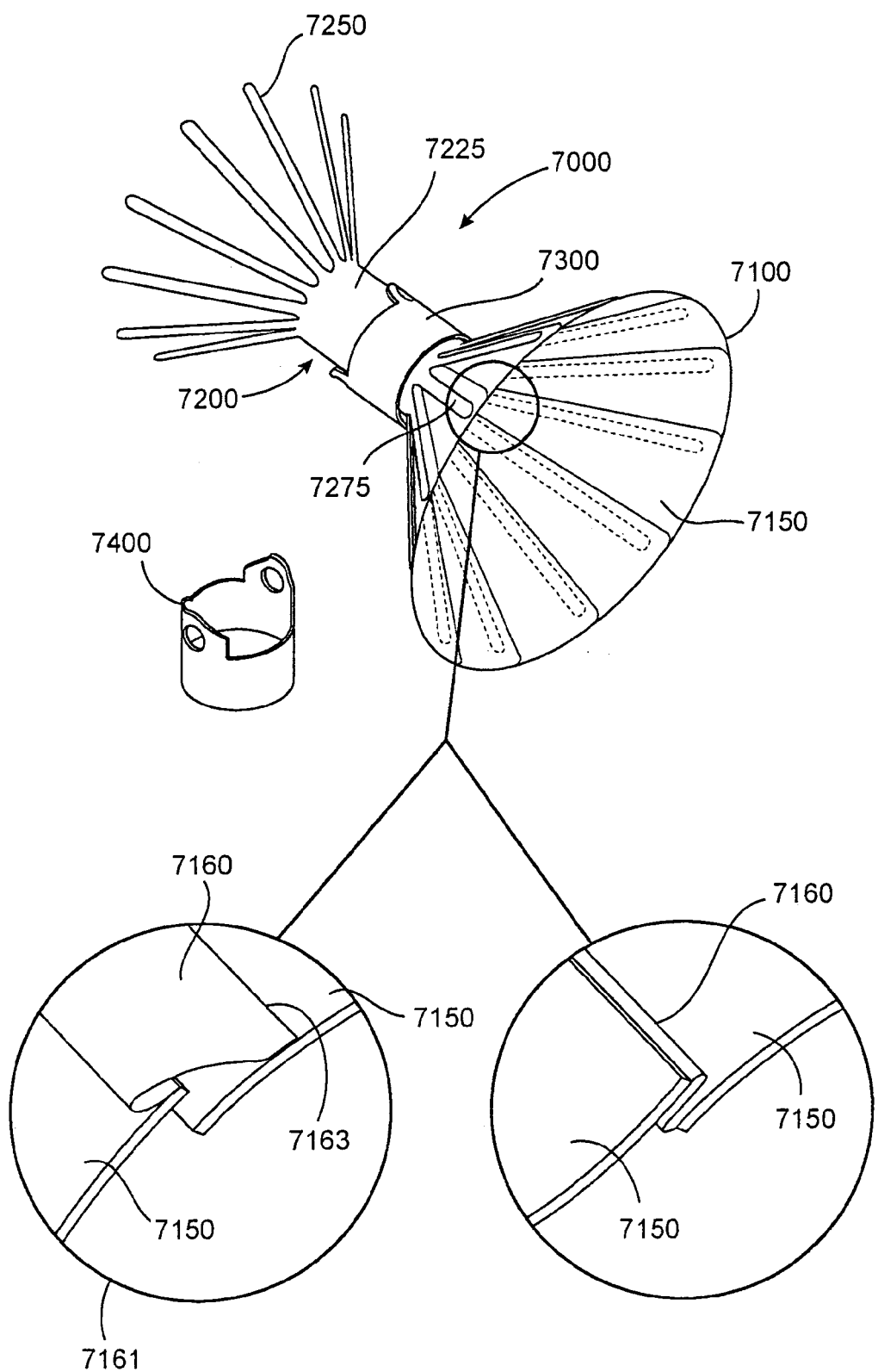
FIG. 60B shows a perspective view of a flow control device having a segmented valve/seal component and shows enlarged views of two embodiments of foldable sections.

Alternately, the individual overlapping segments 7150 may be joined to each other with foldable sections 7160 as shown in FIG. 60B. The foldable section can includes a radial edge that overlaps with and connects to an adjacent overlapping segment 7150. The foldable sections 7160 are flexible enough to allow the overlapping segments 7150 to slide relative to each other in order to maintain a seal with the bronchial wall at various bronchial wall diameters. The foldable sections 7160 act as a secondary seal to prevent the flow of fluid past the device 7000 in the inhalation direction in the situation where the seal between adjacent overlapping segments 7150 is compromised. The foldable sections 7160 may be formed from the same material as the overlapping segments 7150, or may be formed from a different material. The foldable sections may be thinner or may be formed from a lower durometer material to make them more flexible or less stiff than the overlapping segments 7150.

FIG. 60B shows one embodiment of the foldable sections 7160 in the enlarged view 7161. In this embodiment, the foldable section 7160 includes a single fold and a radial edge of the segment 7150 is positioned to overlap with the adjacent segment 7150. The radial edge 7163 can be free to slide over the adjacent segment 7150 or it can be attached to the adjacent segment. In another embodiment, shown in the view 7165 of FIG. 60B, the foldable section 7160 includes two or more folds and the segment 7150 is integrally attached to an adjacent segment 7150.

Figure 61:
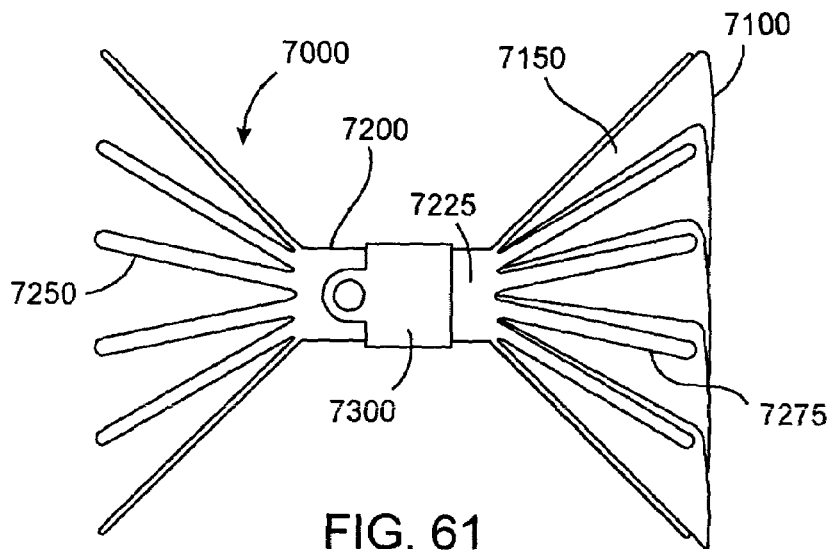
FIG. 61 is a side view of the flow control device depicted in FIG. 59.
Figure 62:
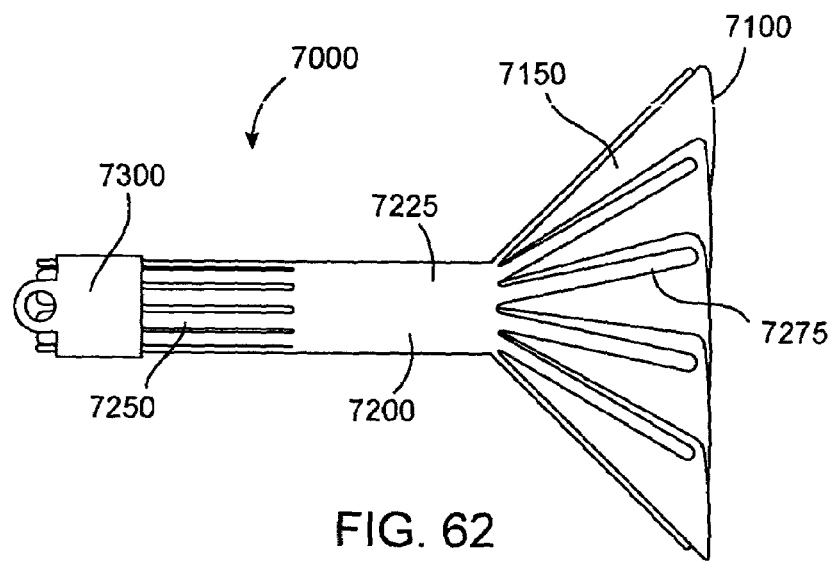
FIG. 62 is a side view of the flow control device depicted in FIG. 59, wherein the flow control device is partially deployed.
Figure 63:
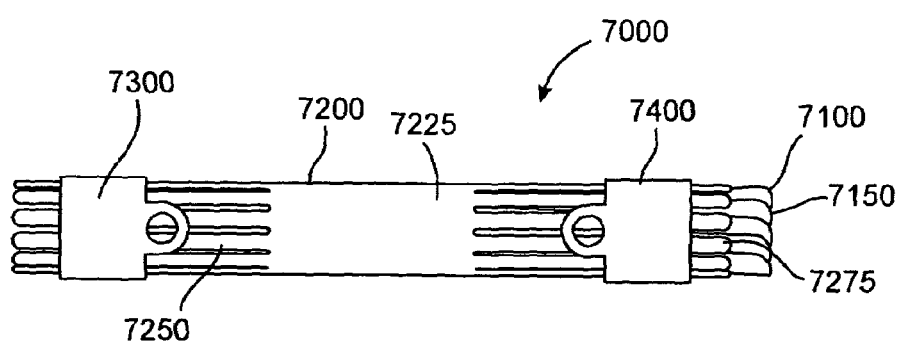
FIG. 63 is a side view of the flow control device depicted in FIG. 59, wherein the flow control device is fully retracted.

As best shown in FIGS. 61–63, the valve/seal component 7100 is supported by a frame 7200. The frame includes a first set of outwardly biased or self-expanding deployable arms 7250 that are used to anchor the device 7000 to the wall of a bronchial lumen. The deployable arms 7250 thus serve the purpose of preventing migration of the device 7000 after implantation in the bronchial lumen in either the inhalation or the exhalation direction. The frame 7000 also includes a second set of deployable arms 7275, which may be self-expanding, or outwardly biased as well. The second set of deployable arms 7275 serve at least two purposes. The first is to further anchor the device 7000 after implantation in the bronchial lumen and to prevent the device from migrating in either the inhalation or the exhalation direction. The second purpose that the deployable arms 7275 serve is to support the valve/seal component 7100 that rests against the deployable arms 7275 on the proximal end of the frame 7200 so that the shape of the valve/seal component 7100 is maintained during inhalation, thus preventing the valve/seal component 7100 or any of the overlapping segments 7150 from turning inside out during a rapid inhalation. The overlapping segments 7150 can be bonded to the deployable arms 7275, or they can rest freely against the deployable arms 7275. The frame 7200 can have as many deployable arms 7275 as there are overlapping segments 7150 in the valve/seal component 7100. Thus, if the valve/seal component 7100 has twelve overlapping segments 7150 as shown in FIGS. 59–65, the frame 7200 can have twelve deployable arms 7275 extending proximally to support each one of the overlapping segments 7150. Likewise, if the valve/seal component 7100 has six overlapping segments 7150, then the frame 7200 can have six deployable arms 7275 to support each of the six overlapping segments 7150. Thus, the frame can have two, three, four, five, six, seven, eight, nine, ten, eleven, twelve or more deployable arms 7275 to match the number of overlapping segments 7150. Alternately, the number of deployable arms 7275 can be different than the number of overlapping segments 7150.

The valve/seal component 7100 can be bonded to the core section 7225 of the frame 7200. The distal ends of the overlapping segments 7150 can be bonded to the proximal end of the core 7225 of the frame 7200 in an overlapping configuration. This leaves the proximal ends of the overlapping segments 7150 free to expand and contract to different diameters. Other retainer configurations are also suitable, as long as the valve/seal component 7100 is supported, and migration in both the inhalation (distal) and the exhalation (proximal) directions is prevented.

FIG. 61 shows the flow control device 7000 in a fully expanded and deployed condition. The retaining sleeve 7300 has been shifted in a proximal direction to release the outwardly biased deployable arms 7250.

FIG. 62 shows the flow control device 7000 in a partially expanded and deployed condition. In this condition, the flow control device 7000 can be introduced into the bronchial lumen and advanced into position to a desired location along the length of the bronchial lumen. The retainer sleeve 7300 is shown in a distalmost position along the length of the frame 7200, such that it is retaining the outwardly-biased deployable arms 7250 in a contracted condition.

FIG. 63 shows the flow control device 7000 in a completely contracted condition. As with the condition shown in FIG. 62, the flow control device 7000 as shown in FIG. 63 can be introduced into the bronchial lumen and advanced into position to a desired location along the length of the bronchial lumen. The retainer sleeve 7300 is shown in a distalmost position along the length of the frame 7200, such that it is retaining the outwardly biased deployable arms 7250. The second retainer sleeve 7400, which is optional, is shown in a proximalmost position along the length of the frame 7200, such that it is retaining the deployable arms 7275 and the overlapping segments 7150 of the valve/seal component 7100 in a contracted condition.

Figure 64:
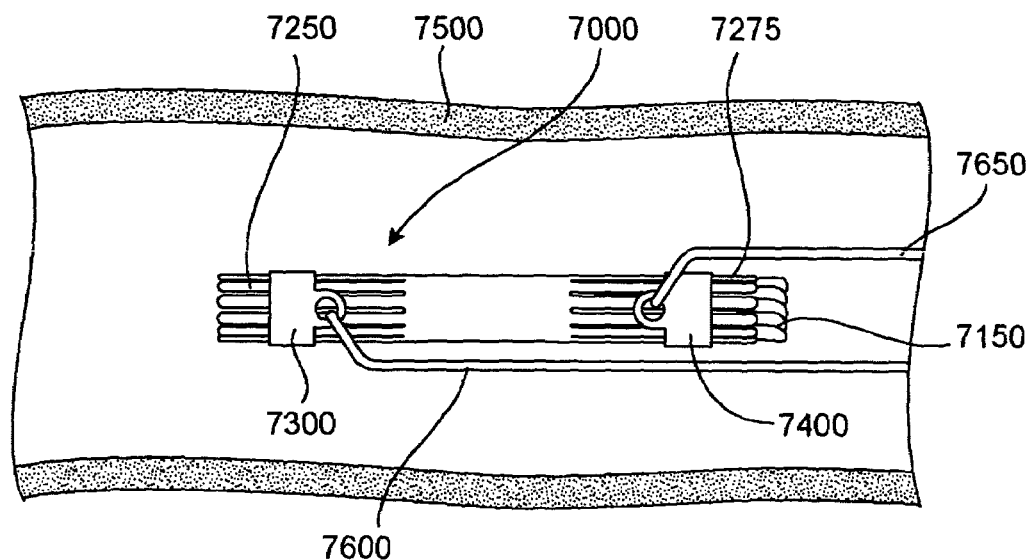
FIG. 64 is a side view of the flow control device depicted in FIG. 59 placed within a bronchial lumen.
Figure 65:
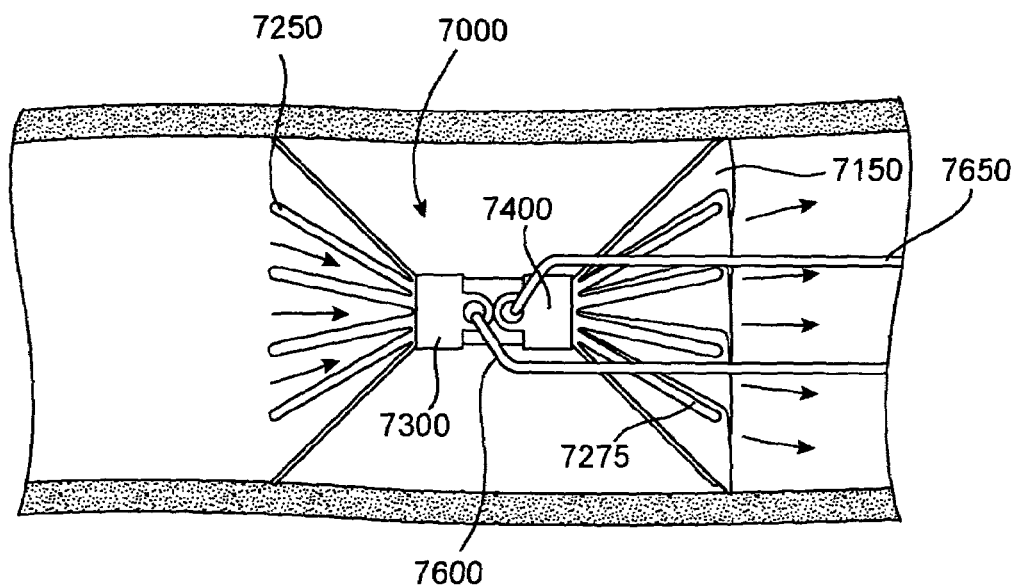
FIG. 65 is a side view of the flow control device depicted in FIG. 64 fully deployed.

One feature of the flow control device 7000 is removability after implantation. FIGS. 64 and 65 show the flow control device 7000 with a retainer sleeve 7300 retaining the outwardly biased deployable arms 7250, and a retainer sleeve 7400 retaining the deployable arms 7275 and the overlapping segments 7150. Removably coupled to a receptacle, such as, for example, a hole, in the retainer sleeve 7300 is an actuation element, such as, for example, a rigid wire or rod 7600, that extends proximally outside of the bronchial lumen 7500. Removably coupled to a receptacle, such as, for example, a hole, in the second retainer sleeve 7400 is a second actuation element, such as, for example, a rigid wire or rod 7650, that also extends proximally outside of the bronchial lumen 7500.

The actuation elements can be used to push or pull the sleeves 7300, 7400. Once the flow control device 7000 is advanced into position in the bronchial lumen, the rod 7600 can be pulled or moved in a proximal direction to slide the sleeve 7300 proximally, thus releasing the outwardly biased deployable arms 7250. Either simultaneously, before, or after the outwardly biased deployable arms 7250 are released, the rod 7650 can be pushed or moved in a distal direction toward the retainer sleeve 7300, thus releasing the deployable arms 7275 and the overlapping segments 7150. Described slightly differently, the motion of moving the two sleeves towards one another can be created by moving the ends of the two rods 7600 and 7650 towards each other. In one embodiment, not shown, this motion can be accomplished by a tool that can hook onto the two wires and pull them together. In any case, the result will be a flow control device 7000 that allows exhaled air and fluid to flow out of the bronchial tube as shown in FIG. 65, but prevents the flow of air or fluid past the flow control device 7000 in the inhalation direction.

When it is time to remove the flow control device 7000, the rod 7600 can be pushed or moved distally to retract the outwardly biased deployable arms 7250, and the rod 7650 can be pulled or moved proximally to retract the deployable arms 7275 and the overlapping segments 7150, thus resulting in the radial collapse of the flow control device 7000. Once collapsed, the flow control device 7000 can be pulled out of the bronchial lumen.

In another embodiment, as shown in FIGS. 61 and 62, the flow control device 7000 has only one retainer sleeve 7300. A rod, not shown, is attached to it. In the insertion stage, the retainer sleeve 7300 retains the outwardly biased deployable arms 7250, and in the removal stage, the retainer sleeve 7300 is moved proximally to retain the deployable arms 7275 and the overlapping segments 7150. Alternatively, rather than using a rod, a forceps or other instrument can be used to grasp the retainer sleeve 7300 and pull it proximally to retain the deployable arms 7275 and the overlapping segments 7150 prior to removal.

The flow control device 7000 can be compressed and constrained inside the outer tube of a delivery catheter, such as a catheter that is comprised of an inner tube and an outer tube. The catheter is located in the desired implant site, and the device is released by withdrawing the outer tube while holding the inner tube in position. Once released, the flow control device 7000 expands to contact and seal against the bronchial lumen. This delivery catheter can be made small enough to be inserted through the biopsy channel of a bronchoscope. This way the bronchoscope can be used to guide the delivery catheter to the target location. The catheter is then advanced into the target lumen, and the flow control device 7000 released.

Umbrella Style Flow Control Devices

Figure 66B:
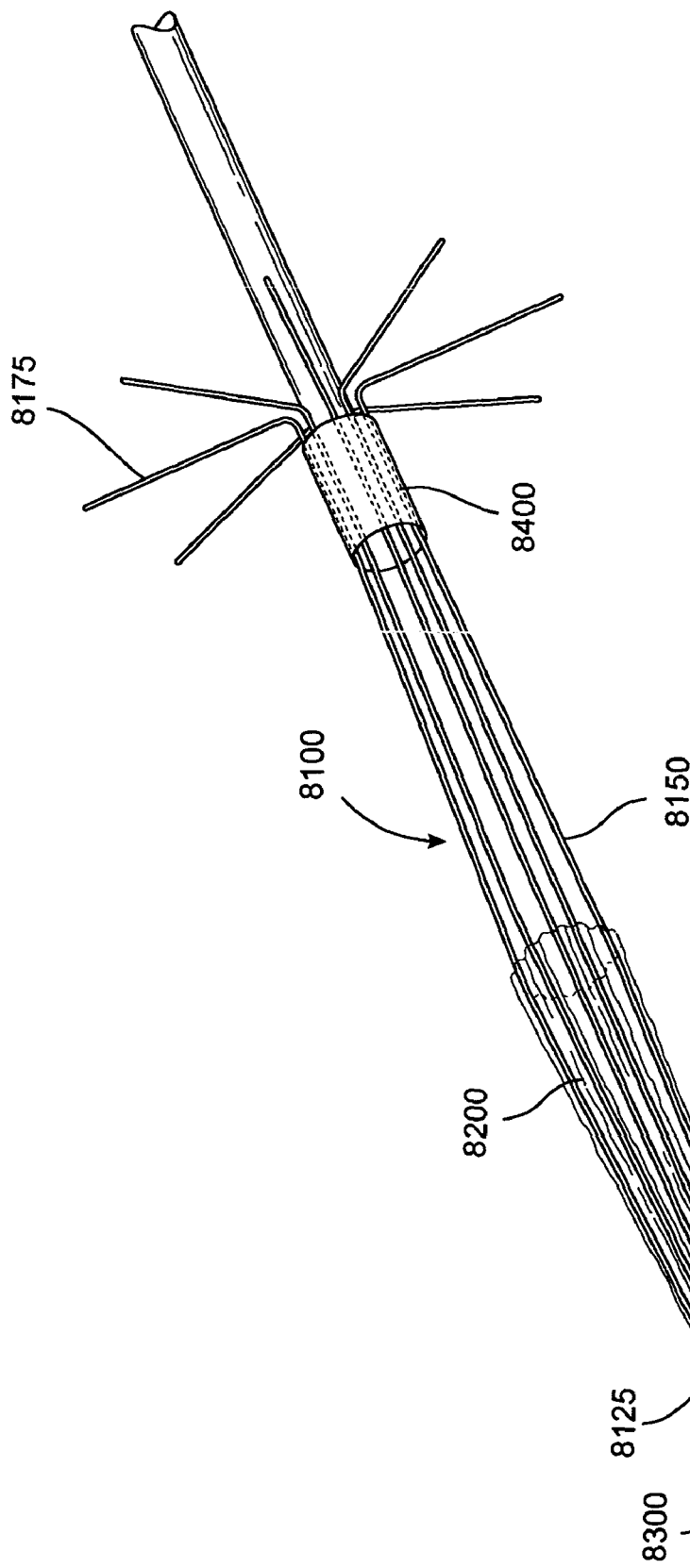
FIG. 66B shows a perspective view of the flow control device of FIG. 66 in a contracted state.

Like numerals are used to refer to like components in the umbrella style flow control devices described in this section. FIGS. 66–70 depict various embodiments of umbrella style flow control devices. FIGS. 66A and 66B show one embodiment of an umbrella style flow control device 8000. The flow control device 8000 is an "umbrella" style one-way valve device in that it is comprised of a frame 8100 with membrane struts 8150 (similar to the tines of an umbrella) that are covered with a thin elastomeric membrane 8200. The membrane 8200 is draped over the membrane struts 8150, thus forming the umbrella shape. The membrane 8200 can be formed of a thin, approximately 0.002 inches thick, polyurethane sheet material. However, other elastomeric materials, such as silicone, may be used, and many other thicknesses, both thicker and thinner than 0.002 inches, may also be used. In one embodiment, the membrane 8200 has a durometer in the range of about 40 Shore A to about 100 Shore A. The membrane 8200 may be bonded to the full length of the membrane struts 8150 running along the inner surface of the membrane, bonded in selected locations along the strut 8150, or not bonded at all.

Each membrane strut 8150 is connected at a distal end to a distal hub 8300 and at a proximal end to a proximal hub 8400. The membrane struts 8150 radiate outwardly (i.e. laterally) from the distal hub 8300 and the proximal hub 8400 to form a ring having a flexible diameter 8500. The membrane struts 8150 can be spring biased outwardly (as shown) so that when the flow control device 8000 is implanted in a bronchial lumen, the struts bias and hold the membrane against the wall of the bronchial lumen.

Figure 67:
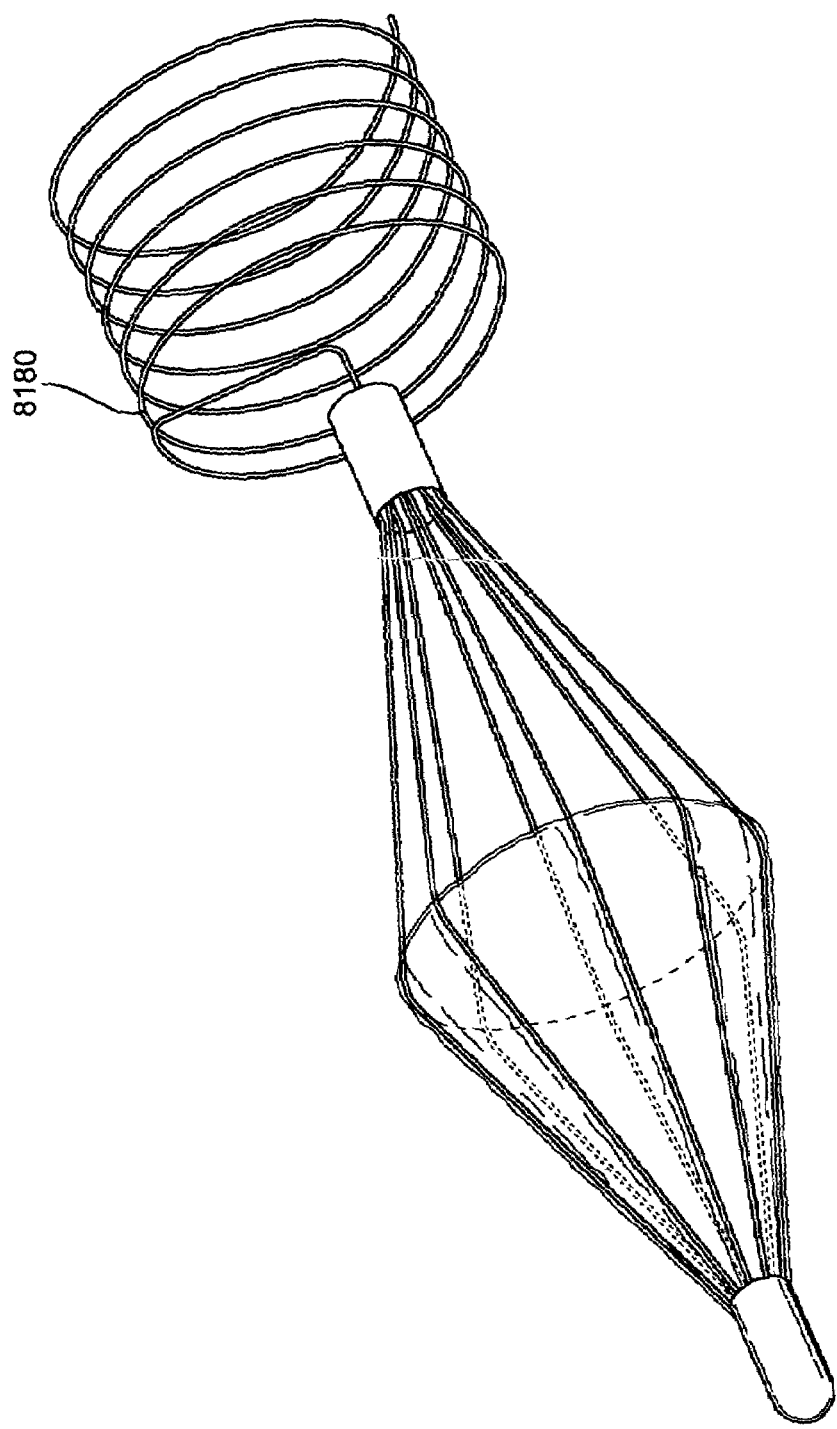
FIG. 67 shows a perspective view of an umbrella style flow control device with a retention spring according to another embodiment.

In the embodiments shown in FIGS. 66A, 66B, and 67, the membrane struts 8150 are attached or bonded together at the distal hub 8300, and again at the proximal hub 8400. When the flow control device 8000 is compressed for loading, as shown in FIG. 66B, the two connectors move away from one another to allow the diameter 8500 of the device to decrease and the device 8000 to radially collapse. When the flow control device 8000 is released or ejected from the delivery catheter housing and allowed to expand, the membrane struts 8150 expand to their former shape and press the membrane 8200 against the bronchial lumen wall. The struts 8150 can have a stiffness sufficient to tension the membrane when deployed in the bronchial lumen or sufficient to exert pressure against the lumen and deform the lumen into a polygonal shape. The membrane can be sufficiently flexible to seal with the wall of the bronchial lumen when the membrane is not tensioned by the struts. The flow control device 8000 can conform to different lumen diameters, and when placed in smaller diameters, the membrane 8200 may pleat or fold to seal against the lumen wall during inhalation.

In another embodiment, not shown, the distal hub 8300 and proximal hub 8400 may be linked by an axial member, such as a cable, rod, or shaft, that allows the distance between the two connectors to be adjusted. In this way, the outer diameter 8500 of the device may be increased by drawing the two connectors together, or may be reduced by spreading the connectors father apart. Accordingly, the flow control device 8000 may be sized to the bronchial lumen, or if desired, the load of the struts against the bronchial lumen wall may be increased or decreased. If the connectors are spread apart, the flow control device 8000 may be collapsed for removal from the bronchial lumen.

In one embodiment, the connectors are linked by a threaded rod (not shown). The rod is captured by the distal hub 8300 but is free to rotate in the distal hub 8300. The proximal hub 8400 is threaded such that it will translate along the threaded rod when the rod is rotated. In this manner, the outer diameter 8500 of the device 8000 may be varied by rotating the threaded rod in one direction or the other. This would allow the device 8000 to be collapsed for delivery without the need for a delivery catheter with a restraining housing, and could be expanded for a good fit within the bronchial lumen by rotating the threaded rod.

Alternatively, the connectors 8300 and 8400 can be linked by a flexible member (not shown) that is fixed to the distal hub 8300, and is threaded through the proximal hub 8400 that includes a locking feature (not shown). In this way, the device can be expanded by pulling the flexible member through the proximal hub 8400 until the device 8000 expands to the desired diameter, and then locked in place at the proximal hub 8400. Of course, other adjustment members and methods are also possible.

Fluid (gas or liquid) will flow past the flow control device 8000 in the proximal direction, for example during exhalation, by flowing along the bronchial lumen wall between the membrane struts 8150 by pushing the membrane 8200 away from the wall thus creating flow channels between each pair of membrane struts 8200. When flow is reversed, for example during inhalation, the fluid flow in the distal direction will force the membrane 8200 against the bronchial lumen wall, thus sealing the passage and preventing flow past the flow control device 8000. There are also two or more retention elements comprised of retainer struts 8175 on the distal end, the proximal end (as shown in FIGS. 66A and 66B), or both ends. The retention struts 8175 protrude laterally from the frame, For example, the retention struts 8175 can have a shape, such as an outwardly-flared shape, that serves to grip the bronchial lumen wall to prevent migration of the flow control device 8000 in either the distal or proximal directions. The retainer struts 8175 are shown in FIG. 66B in a deployed state, but they would be retracted if loaded into a delivery catheter, returning to their deployed position only upon release from the delivery catheter. In the deployed position, the retainer struts 8175 are at an angle of approximately ninety degrees relative to the connector 8400, though angles greater than or less than ninety degrees may be used.

Figure 66C:
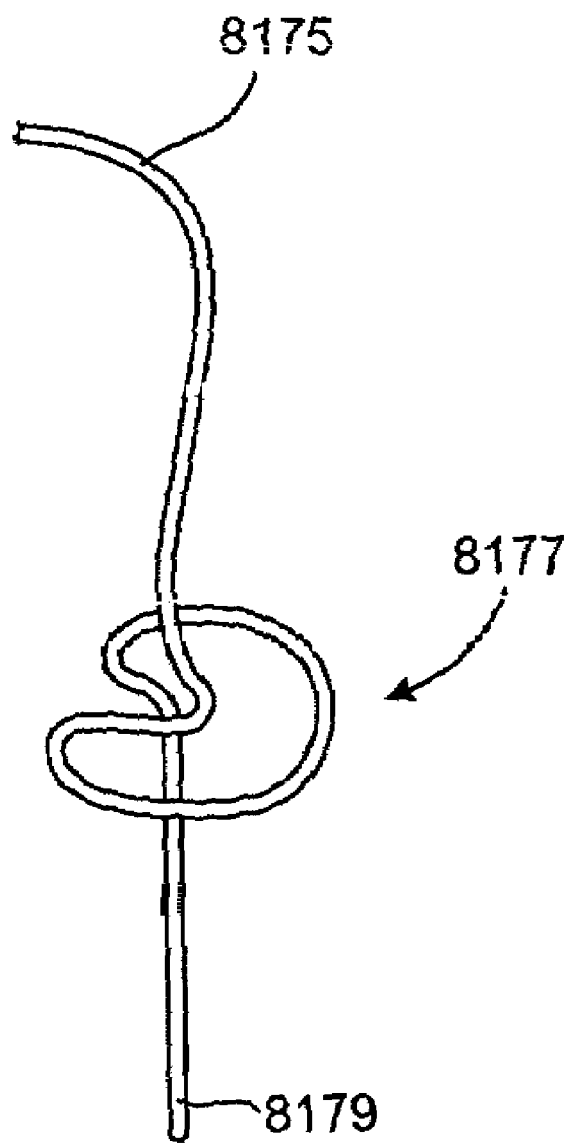
FIG. 66C shows an enlarged view of one embodiment of a retention strut.

Alternately, the end of the retention struts 8175 may be formed into the shape shown in FIG. 66C. The retention strut 8175 includes an enlarged section 8177 that can be formed, for example, by bending or twisting a portion of the retention strut 8175 to form a foot. With this shape, the depth of penetration of the distal end 8179 of the retention strut 8175 into the bronchial lumen wall is limited, and will prevent the distal end 8175 of the strut from penetrating beyond a predetermined distance into the lumen wall. In this embodiment, the retention strut end is formed from the strut material, however other configurations are possible such as attaching a strut end to the retention strut 8175 that is formed as a separate component.

As shown in FIGS. 66A and 66B, the frame 8100 has eight membrane struts 8100, but it can have two, three, four, five, six, seven, eight, nine, ten, eleven, twelve, or more struts 8100. The struts shown in the figures are plain end wires, however other configurations may be used. The membrane struts 8150 and the retention struts 8175 (or retention coil 8180) can be made of nickel-titanium alloy (such as Nitinol) wire. Nitinol can be chosen for its superelastic properties so that the flow control device 8000 can be compressed to a small diameter for insertion in a delivery catheter, yet still expand to its original shape after deployment. It should be appreciated that many other elastic materials would work well including stainless steel, plastic, etc.

As mentioned above with respect to FIG. 66C, a bend in the wire end, or a foot could be attached to the retention struts to prevent migration. In an alternative embodiment, as shown in FIG. 67, the retention element comprises a retention coil 8180 that can be used instead of retention struts 8175 to prevent migration. The retention spring can extend proximally from the proximal hub 8400 and can expand to fit different sized bronchial lumens.

Figure 68:
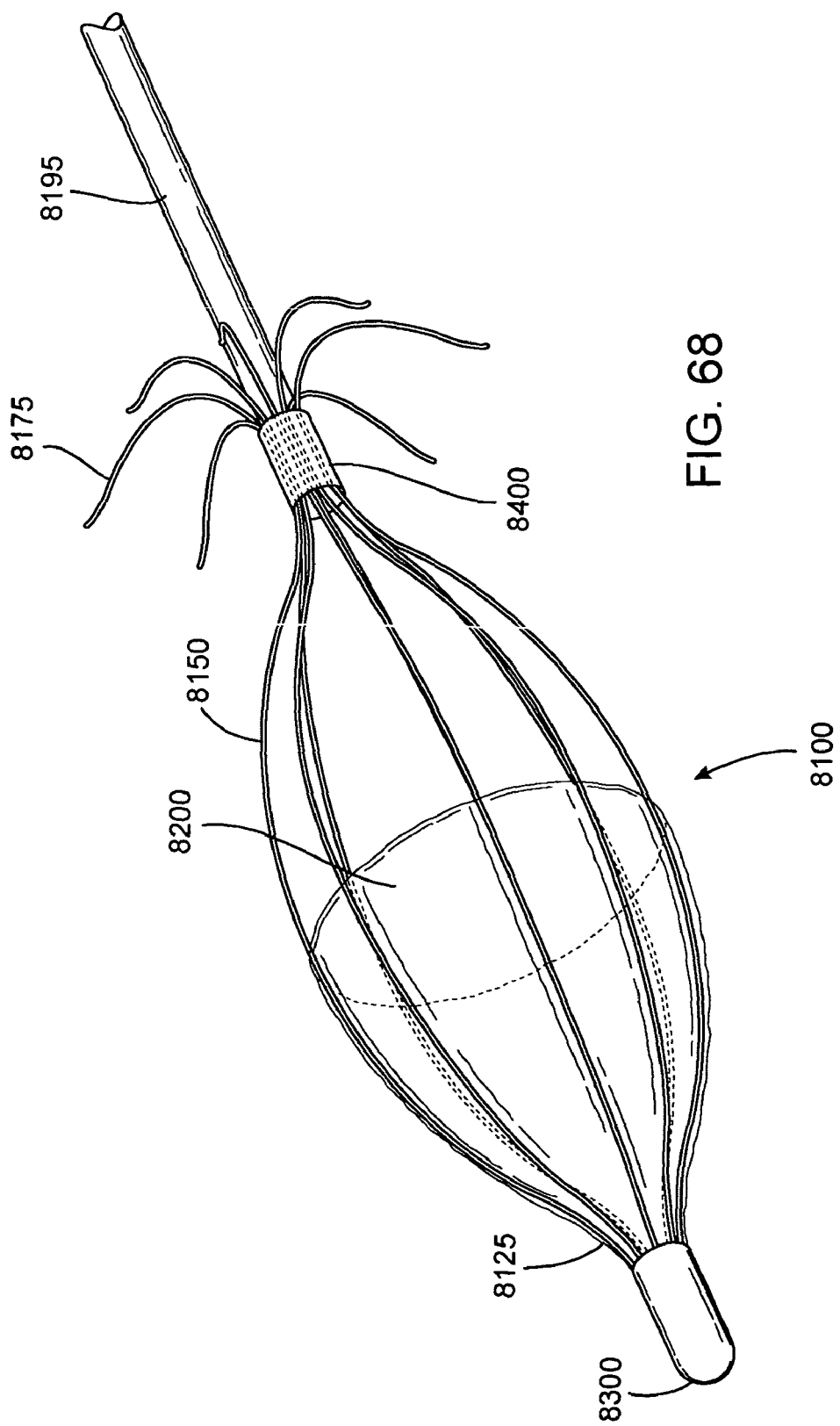
FIG. 68 shows a perspective view of an umbrella style flow control device with curved struts according to another embodiment.

In another embodiment, as shown in FIG. 68, the membrane struts 8150 have a curved shape where they contact the membrane 8200, rather than the straight shape shown in the embodiments depicted in FIGS. 66A, 66B, and 67. In this way, the membrane 8200 may conform more closely to the bronchial lumen wall when placed in bronchial lumens of different diameters.

Figure 69:
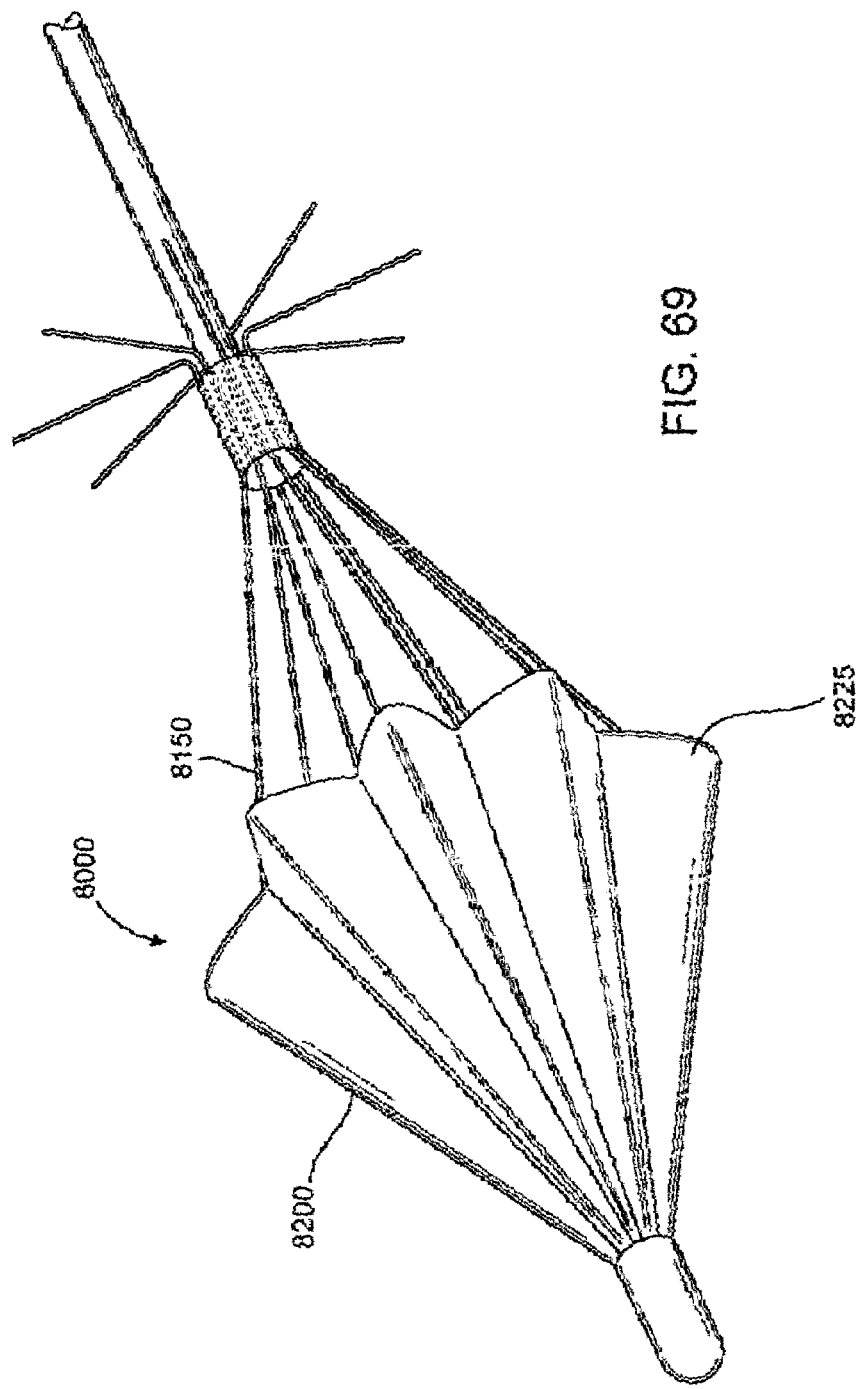
FIG. 69 shows a perspective view of an umbrella style flow control device with pleated membrane according to another embodiment.

In another embodiment as shown in FIG. 69, pleats 8225 are formed into the membrane 8200 between the membrane struts 8150. In this embodiment, the pleats 8225 are preformed so that the shape and aspect of the pleats will be controlled in order to improve the sealing performance of the flow control device 8000. In this embodiment, the membrane 8200 is pleated when placed in all diameters of bronchial lumens. It may also be beneficial to extend the length of the pleats 8225 so that the pleat 8225 is under the adjacent membrane strut 8150 at all diameters of the device 8000. This way the membrane strut 8150 will ensure that the pleat 8225 is held against the bronchial lumen wall.

Figure 70:
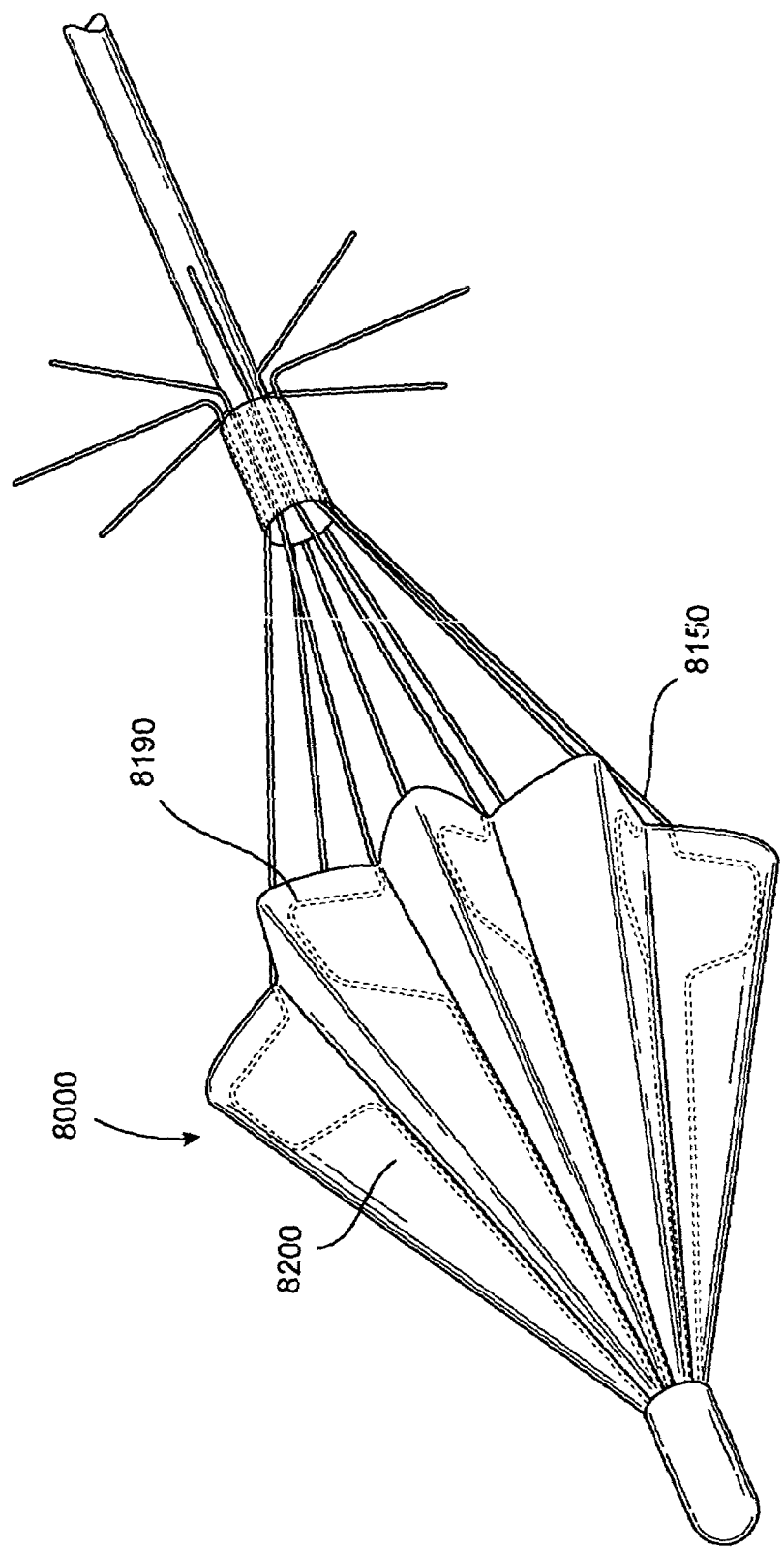
FIG. 70 shows a perspective view of an umbrella style flow control device with bended struts according to another embodiment.

In yet another embodiment as shown in FIG. 70, preformed pleats 8225 in the membrane 8200 are supported by bends 8190 in the membrane struts 8150. The bends 8190 in the membrane struts 8150 hold the pleats 8225 firmly against the wall of the bronchial lumen after placement, and they ensure that when flow is reversed from exhalation to inhalation, the membrane seals against the bronchial lumen wall. As with the other embodiments, the frame 8100 can have two, three, four, five, six, seven, eight, nine, ten, eleven, twelve, or more struts 8150, each with a bend 8190. Alternatively, alternating struts 8150 can have one or more bends 8190. Also, the membrane 8200 can be bonded to the full length of the membrane struts 8150, or just to selected locations such as the bends 8190, or not bonded at all.

The umbrella style flow control devices depicted in FIGS. 66–70, may be compressed inside a housing of a delivery catheter for delivery into the target bronchial lumen. As housing may be retracted, or the flow control device pushed out of the housing, in order to release the device in the target bronchial lumen and allow it to expand to contact the lumen wall. Alternatively, they may be positioned in a bronchial tube with a push catheter 8195 as shown in FIGS. 66A, 66B, and 68.

Methods of Use

Disclosed is a method of deploying a flow control device 110 to a bronchial passageway in order to regulate or eliminate airflow to or from a targeted lung region. The deployed flow control device 110 can eliminate air flow into the targeted lung region and result in collapse of the targeted lung region. However, the deployed flow control device 110 need not result in the collapse of the targeted lung region in order to gain a beneficial effect. Rather, the flow control device 110 can regulate airflow to and from the targeted lung region to achieve an improved air flow dynamic, such as by eliminating airflow into the targeted lung region during inhalation, but not resulting in collapse. The deployment of the flow control device 110 can channel or redirect the inhaled air to a non-isolated, healthier region of the lung, thus improving ventilation to the healthier lung tissue, and improving ventilation-perfusion matching in the healthier lung region. The exhaled air of the targeted lung region can still be vented through the implanted one-way flow control device 110, and thus the exhalation dynamics of the targeted lung region need not be affected by the presence of the flow control device. This can result in an increase in the efficiency of oxygen uptake in the lungs.

The method of deployment and treatment can be summarized according to the following steps, which are described in more detail below. It should be appreciated that some of the steps are optional and that the steps are not necessarily performed in the order listed below. The steps include:

(a) identifying a targeted lung region and determining a target location in bronchial passageway(s) to which the flow control device will be deployed;

(b) determining the diameter of the target location in the bronchial passageway(s) and selecting an appropriately sized flow control device for deploying in the lumen of the bronchial passageway; as described below, this step is optional, as a flow control device can be manufactured to span a wide range of bronchial diameters so that lumen measurement would not be necessary;

(c) loading the selected flow control device into a delivery device, such as the delivery catheter described above, for delivering and deploying the flow control device to the bronchial passageway; this step is optional, as the flow control device can be manufactured or obtained pre-loaded in a delivery device;

(d) positioning the delivery catheter within the bronchial passageway so that the flow control device is positioned at the target location in the bronchial passageway;

(e) deploying the flow control device at the target location in the bronchial passageway;

(f) removing the delivery device;

(g) performing one or more procedures on the targeted lung region and/or allowing reactions to occur in the targeted lung region as a result of the presence of the flow control device.

According to step (a), a physician or technician evaluates the diseased area of a patient's lung to determine the targeted lung region and then determines the bronchial passageway(s) that provide airflow to the targeted lung region. Based on this, one or more target locations of bronchial passageways can be determined to which one or more flow control devices can be deployed.

In step (b), the proper size of a flow control device for insertion into the bronchial passageway is determined. As mentioned, this step is optional, as a flow control device can be manufactured to span a wide range of bronchial diameters so that lumen measurement would not be necessary. It should be appreciated that a precise match between the size of the flow control device 110 and the lumen of the bronchial passageway is not required, as the compressibility and expandability of the flow control device 110 provides a variation in size. In one embodiment, the flow control device is selected so that its size is slightly larger than the size of the bronchial passageway.

Various methods of measuring a bronchial passageway diameter are known and understood in the art. For example, a balloon having a known ratio of inflation to diameter can be used, thus allowing an accurate way of determining a bronchial passageway diameter. A loop or measuring device such as a marked linear probe may also used. The diameter could also be measured using a high resolution computerized tomography (CT) scan. Even an "eye-ball" estimate could also be sufficient, wherein the sizing is done visually without using a measuring tool, depending on the skill of the physician.

In step (c), the flow control device is loaded onto a delivery system, such as the delivery system 2910 comprised of the catheter 2915 that was described above with reference to FIG. 31. If the delivery system 2910 is used, the flow control device 110 is loaded into the housing 2940 at the distal end of the catheter 2915, such as by using the loader system 3510, described above. Alternately, the flow control device 110 can be loaded into the housing 2940 by hand. As mentioned, the loading step can be optional, as the flow control device 110 can be manufactured or obtained with the flow control device pre-loaded. It should be appreciated that other delivery systems could also be used to deliver the flow control device to the bronchial passageway.

In step (d), the delivery catheter is inserted into the bronchial passageway so that the flow control device 110 is positioned at a desired location in the bronchial passageway. This can be accomplished by inserting the distal end of the delivery catheter 2915 into the patient's mouth or nose, through the trachea, and down to the target location in the bronchial passageway. The delivery of the delivery catheter 2915 to the bronchial passageway can be accomplished in a variety of manners. In one embodiment, a bronchoscope is used to deliver the delivery catheter 2915. For example, with reference to FIG. 71, the delivery catheter 2915 can be deployed using a bronchoscope 5210, which in an exemplary embodiment has a steering mechanism 5215, a shaft 5220, a working channel entry port 5225, and a visualization eyepiece 5230. The bronchoscope 5210 has been passed into a patient's trachea 225 and guided into the right primary bronchus 510 according to well-known methods.

Figure 71:
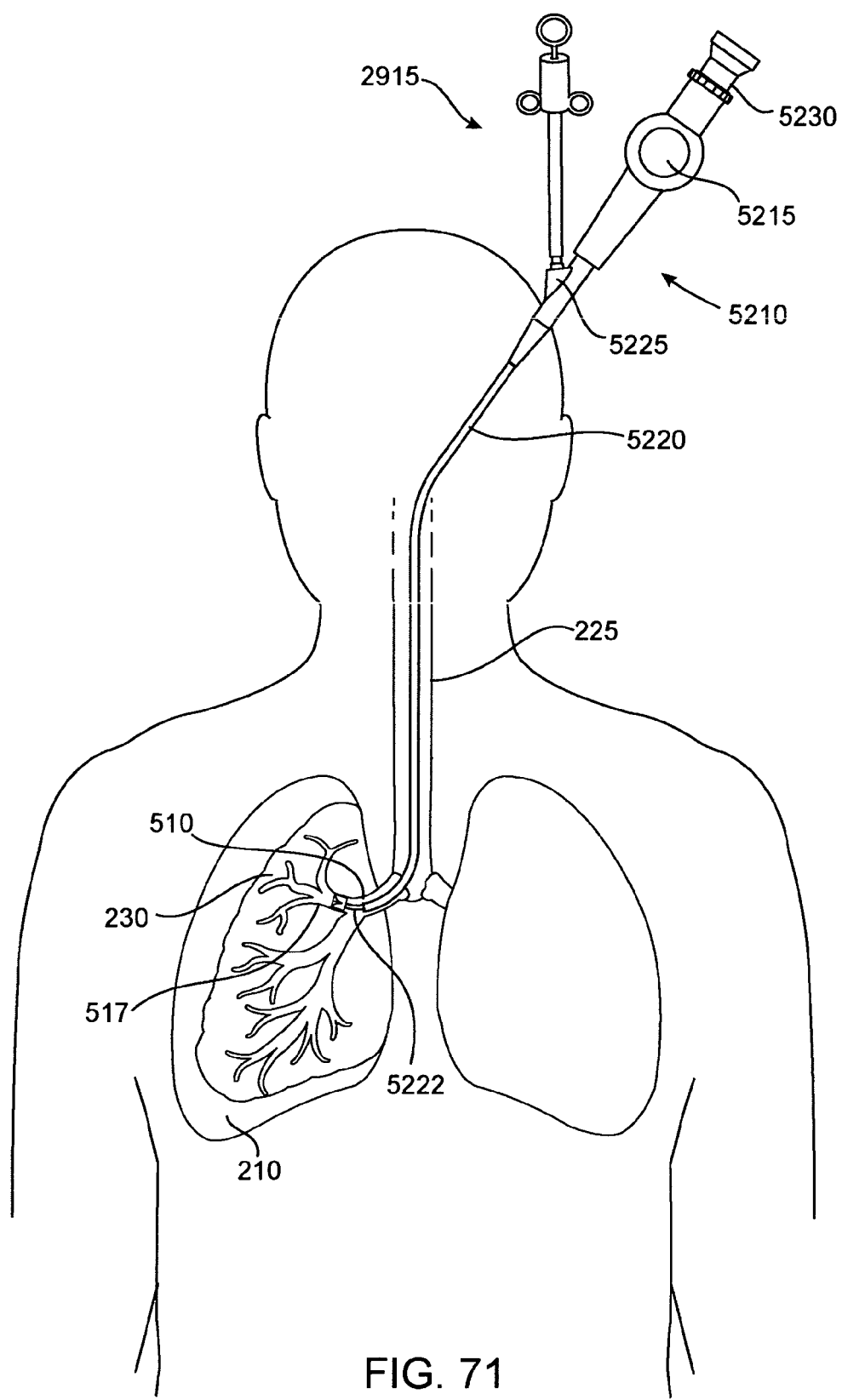
FIG. 71 shows a bronchoscope deployed within a bronchial tree of a patient.

It is important to note that the distal end of the bronchoscope is preferably deployed to a location that is at least one bronchial branch proximal to the target bronchial lumen where the flow control device will be implanted. If the distal end of the bronchoscope is inserted into the target bronchial lumen, it is impossible to properly visualize and control the deployment of the flow control device in the target bronchial lumen. For example, if the bronchoscope is advance into the right primary bronchus 510 as shown in FIG. 71, the right upper lobar bronchi 517 can be visualized through the visualization eyepiece of the bronchoscope. The right upper lobar bronchi 517 is selected as the target location for placement of a flow control device 110 and the distal end of the bronchoscope is positioned one bronchial generation proximal of the bronchial passageway for the target location. Thus, the distal end of the bronchoscope is deployed in the right primary bronchus 510. The delivery catheter 2915 is then deployed down a working channel (not shown) of the bronchoscope shaft 5220 and the distal end 5222 of the catheter 2915 is guided out of the distal tip of the bronchoscope and advanced distally until the delivery system housing containing the compressed flow control device is located inside the lobar bronchi 517.

The steering mechanism 5215 can be used to alter the position of the distal tip of the bronchoscope to assist in positioning the distal tip of the delivery catheter 5222 such that the delivery catheter housing can be advanced into the desired bronchi (in this case the lobar bronchi 517). It should be appreciated that this technique can be applied to any desired delivery target bronchi in the lungs such as segmental bronchi, and not just the lobar bronchi.

Alternately, the delivery catheter 2915 can be fed into the bronchoscope working channel prior to deploying the bronchoscope to the bronchial passageway. The delivery catheter 2915 and the bronchoscope 5210 can then both be delivered to the bronchial passageway that is one generation proximal to the target passageway as a single unit. The delivery catheter can then be advanced into the target bronchi as before, and the flow control device 110 delivered.

In another embodiment, the inner member 2920 of the delivery catheter 2915 has a central guidewire lumen, so that the catheter 2915 is deployed using a guidewire that guides the catheter 2915 to the delivery site. In this regard, the delivery catheter 2915 could have a well-known steering function, which would allow the catheter 2915 to be delivered with or without use of a guidewire. FIGS. 60–61 illustrate how the catheter 2915 can be used to deliver the flow control device 110 using a guidewire.

Figure 72:
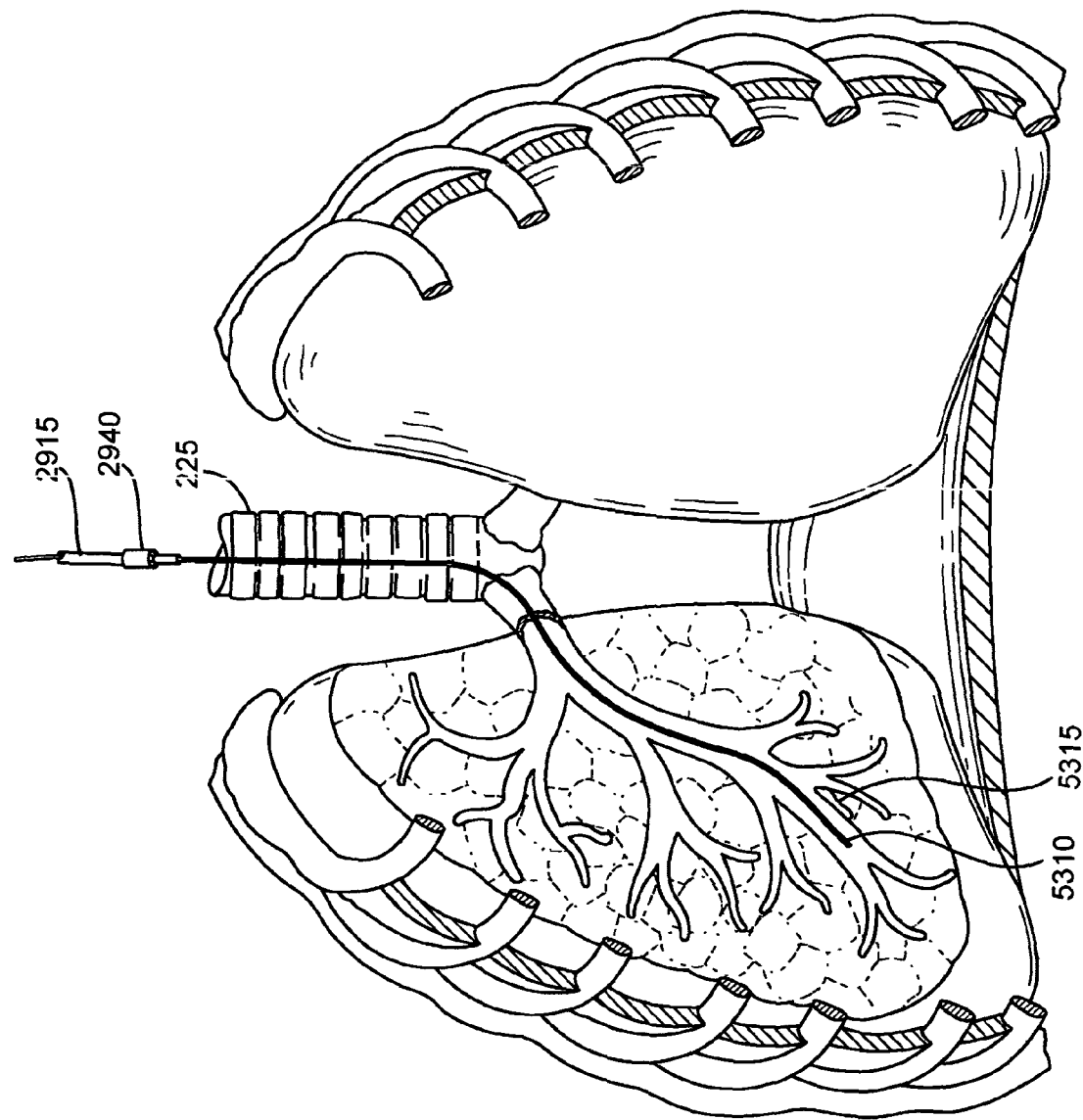
FIG. 72 shows a guidewire deployed within a bronchial tree of a patient.

FIG. 72 illustrates a first step in the process of deploying a delivery catheter 2915 to a target location using a guidewire. A guidewire 5310 is shown passed down the trachea 225 so that the distal end of the guidewire 5310 is at or near the target location 5315 of the bronchial passageway. The guidewire 5310 can be deployed into the trachea and bronchial passageway through free wiring, wherein the guidewire 5310 with a steerable tip is alternately rotated and advanced toward the desired location. Exchange wiring can also be used, wherein the guidewire 5310 is advanced down the working channel of a bronchoscope that has been previously deployed. The bronchoscope can then be removed once the guidewire is at the desired location.

Figure 73:
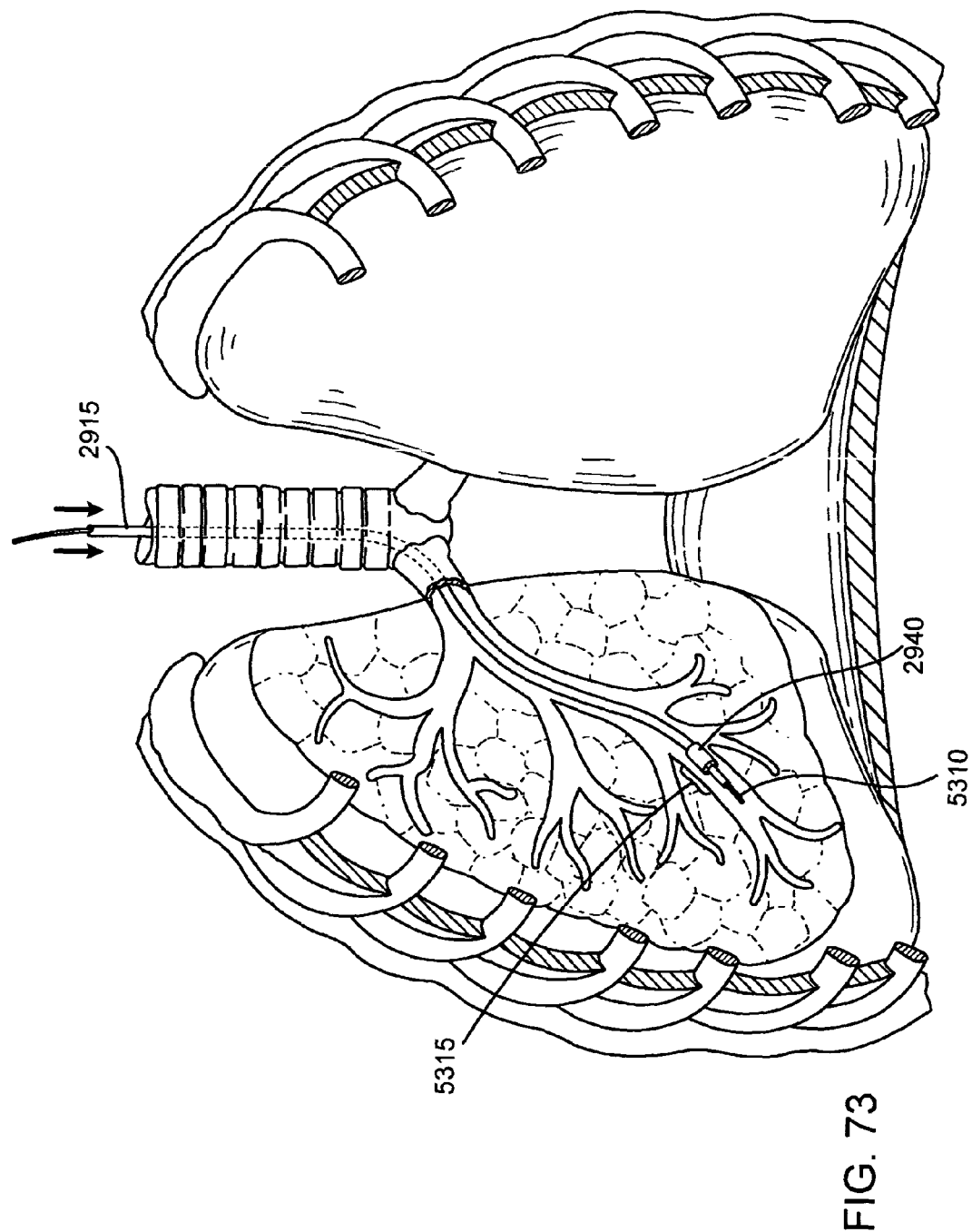
FIG. 73 shows a delivery catheter deployed within a bronchial tree of a patient over a guidewire.

In any event, after the guidewire 5310 is deployed, the distal end of the delivery catheter 2915 is back loaded over the proximal end of the guidewire 5310. The delivery catheter 2915 is advanced along the guidewire 5310 until the housing 2940 on the distal end of the delivery catheter 2915 is located at the target location 5315 of the bronchial passageway. The guidewire 5310 serves to control the path of the catheter 2915, which tracks over the guidewire 5310, and insures that the delivery catheter 2915 properly negotiates the path to the target site. Fluoroscopy can be helpful in visualizing and insuring that the guidewire 5310 is not dislodged while the delivery catheter is advanced. As shown in FIG. 73, the delivery catheter 2915 has been advanced distally over the guidewire 5310 such that the housing 2940 at the distal end of the delivery catheter 5310 has been located at the target location 5315 of the bronchial passageway. The flow control device 110 is now ready for deployment.

Visualization of the progress of the distal tip of the delivery catheter 2915 can be provided by a bronchoscope that is manually advanced in parallel and behind the delivery catheter 2915. Visualization or imaging can also be provided by a fiberoptic bundle that is inside the inner member 2920 of the delivery catheter 2915. The fiberoptic bundle could be either a permanent part of the inner member 2920, or could be removable so that it is left in place while the housing 2940 is maneuvered into position at the bronchial target location, and then removed prior to deployment of the flow control device 110. The removable fiberoptic bundle could be a commercial angioscope which has fiberoptic lighting and visualization bundles, but unlike a bronchoscope, it is not steerable.

Passage of the delivery catheter through tortuous bronchial anatomy can be accomplished or facilitated by providing the delivery catheter 2915 with a steerable distal end that can be controlled remotely. For example, if the distal end of the catheter 2915 could be bent in one direction, in an angle up to 180 degrees, by the actuation of a control on the handle 2925, the catheter 2915 could be advanced through the bronchial anatomy through a combination of adjusting the angle of the distal tip deflection, rotating the delivery catheter 2915, and advancing the delivery catheter 2915. This can be similar to the way in which many bronchoscopes are controlled.

It can be advantageous to use a specific design of a guidewire that configured to allow the delivery catheter 2915 to navigate the tortuous bronchial anatomy with minimal pushing force, and minimal hang-ups on bronchial carinas.

A guidewire can be constructed of a stainless steel core which is wrapped with a stainless steel coil. The coil is coated with a lubricous coating, such as a Polytetrafluoroethylene (PTFE) coating, a hydrophilic coating, or other lubricious coating. The guidewire can be in the range of, for example, around 180 cm in length and 0.035" inch in overall diameter, though other lengths and diameters are possible. A proximal portion of the wire core can be constructed so that after winding the outer coil onto the core, it is as stiff as possible but still allows for easy placement in the lungs using an exchange technique with a bronchoscope. The distal portion, such as the distal-most 2–5 cm, of the wire core may be made with a more flexible construction in order to create an atraumatic tip to the wire. This atraumatic nature of the distal tip can be enhanced by adding a "modified j" tip. A portion of the wire (such as about 3 cm) between the distal and proximal sections could provide a gradual stiffness transition so that the guidewire does not buckle when placed in the lung anatomy.

By having a relatively short atraumatic section, the clinician can place the guidewire in the target location of the bronchial passageway with only a small length of guidewire extending distally of the target passageway. This will minimize the probability of punctured lungs and other similar complications. The clinician can then utilize the stiff nature of the proximal portion of the guidewire to facilitate placing the delivery catheter all the way to the target bronchial passageway.

With reference again to the method of use, in step (e), the flow control device 110 is deployed at the target location of the bronchial passageway. The flow control device 110 is deployed in the bronchial lumen such that the flow control device 110 will provide a desired fluid flow regulation through the bronchial lumen, such as to permit one-way fluid flow in a desired direction, to permit two-way fluid flow, or to occlude fluid flow.

The deployment of the flow control device 110 can be accomplished by manipulating the two-piece handle 2925 of the catheter 2915 in order to cause the housing 2940 to disengage from the flow control device 110, as was described above with reference to FIGS. 36 and 37. For example, the handle can be actuated to withdraw the outer member of the catheter relative to the inner member, which will cause the housing 2940 to move in a proximal direction while the flange on the inner member retains the flow control device 110 against movement within the bronchial passageway. By withdrawing the housing instead of advancing the flange, the flow control device 110 can be deployed in the bronchial passageway at the target location, rather than being pushed to a more distal location. After the flow control device 110 has been deployed at the target site in the bronchial passageway, the delivery devices, such as the catheter 2915 and/or guidewire, is removed in step (f).

Either all or a portion of the flow control device 110 can be coated with a drug that will achieve a desired effect or reaction in the bronchial passageway where the flow control device 110 is mounted. For example, the flow control device 110 can be coated with any of the following exemplary drugs or compounds:

(3) Anti-inflammatory agents to reduce inflammation.

(4) Anti-proliferative agents to treat cancer.

(5) Mucolytic agents to reduce or eliminate mucus production.

(6) Analgesics or pain killers, such as Lidocane, to suppress early cough reflex due to irritation.

(7) Coagulation enhancing agents to stop bleeding.

(8) Vasoconstrictive agents, such as epinephrine, to stop bleeding.

(9) Agents to regenerate lung tissue such as all-trans-retinoic acid.

(10) Steroids to reduce inflammation.

(11) Gene therapy for parenchymal regeneration.

(12) Tissue growth inhibitors (paclitaxel, rapamycin, etc.).

(13) Sclerosing agents, such as doxycycline, minocycline, tetracycline, bleomycin, cisplatin, doxorubicin, fluorouracil, interferon-beta, mitomycin-c, Corynebacterium parvum, methylprednisolone, and talc.

(14) Agents for inducing a localized infection and scar, such as a weak strain of Pneumococcus.

(15) Fibrosis promoting agents, such as a polypeptide growth factor (fibroblast growth factor (FGF), basic fibroblast growth factor (bFGF), transforming growth factor-beta (TGF-$\beta$)).

(16) Pro-apoptopic agents such as sphingomyelin, Bax, Bid, Bik, Bad, caspase-3, caspase-8, caspase-9, or annexin V.

(17) PTFE, parylene, or other lubricous coatings.

(18) In addition, the retainer and other metal components could be irradiated to kill mucus production or to create scar tissue.

It should be appreciated that the aforementioned list is exemplary and that the flow control device 110 can be coated with other types of drugs or compounds.

After the flow control device 110 is implanted, the targeted lung region can be allowed to collapse over time due to absorption of trapped gas, through exhalation of trapped gas through the implanted flow control device 110, or both. As mentioned, collapse of the targeted lung region is not necessary, as the flow control device 110 can be used to simply modify the flow of air to the targeted lung region. Alternately, or in addition to, allowing the targeted lung region to collapse over time, one or more methods of actively collapsing the lung segment or segments distal to the implanted flow control device or devices can be performed. One example of an active collapse method is to instill an absorbable gas through a dilation catheter placed through the flow control device and very distally in the targeted lung region, while at the same time aspirating at a location proximal to the flow control device 110 with a balloon catheter inflated in the proximal region of the flow control device 110. In another example, oxygen is instilled into the distal isolated lung region through a catheter that dilates the flow control device 110. When this is complete, a method of actively collapsing the isolated lung region could be performed (such as insuflating the pleural space of the lung) to drive the gas present in the isolated lung region out through the implanted flow control device 110. One example of performing active collapse without a dilation device present would be to insert a balloon into the pleural space and inflate it to force gas or liquid out of the isolated lung region and collapse the lung.

The following is a list of methods that can be used to actively collapse a targeted lung region that has been bronchially isolated using a flow control device implanted in a patient's bronchial passageway:

(1) The patient is allowed to breath normally until air is expelled from the lung segment or segments distal to the device.

(2) The targeted lung region is aspirated using a continuous vacuum source that can be coupled to a proximal end of the delivery catheter, to a dilator device that crosses the flow control device, or to a balloon catheter placed proximally to the implanted flow control device.

(3) Fluid is aspirated from the targeted lung region using a pulsed (rather than continuous) vacuum source.

(4) Fluid is aspirated from the targeted lung region using a very low vacuum source over a long period of time, such as one hour or more. In this case, the catheter may be inserted nasally and a water seal may control the vacuum source.

(5) The targeted lung region can be filled with fluid, which is then aspirated.

(6) Insufflate pleural space of the lung with gas through a percutaneously placed needle, or an endobronchially placed needle, to compress the lung.

(7) Insert a balloon into the pleural space and inflate the balloon next to targeted lung region.

(8) Insert a percutaneously placed probe and compress the lung directly.

(9) Insert a balloon catheter into the bronchial passageway leading to adjacent lobe(s) of the targeted lung region and over-inflate the adjacent lung segment or segments in order to collapse the targeted lung region.

(10) Fill the pleural space with sterile fluid to compress the targeted lung region.

(11) Perform external chest compression in the region of the target segment.

(12) Puncture the targeted lung region percutaneously and aspirate trapped air.

(13) Temporarily occlude the bronchus leading to the lower lobe and/or middle lobe as the patient inhales and fills the lungs, thus increasing compression on the target lung segment or segments during exhalation.

(14) Induce coughing.

(15) Encourage the patient to exhale actively with pursed lip breathing.

(16) Use an agent to clear or dilate the airways including mucolytics, bronchodilators, surfactants, desiccants, solvents, necrosing agents, sclerosing agents, perflourocarbons, or absorbents, then aspirate through the flow control device using a vacuum source.

(17) Fill the isolated lung region with 100% oxygen (O2) or other easily absorbed gas. This could be accomplished using a dilation device, such as a catheter, that is passed through an implanted flow control device. The oxygen would dilute the gas that is in the isolated lung region to thereby raise the oxygen concentration, causing any excess gas to flow out of the isolated lung region through the flow control device or dilation device. The remaining gas in the isolated lung region would have a high concentration of oxygen and would be more readily absorbed into the blood stream. This could possibly lead to absorption atelectasis in the isolated lung region. The remaining gas in the isolated lung region could also be aspirated back through the dilation device to aid in collapse of the isolated lung region.

Optionally, a therapeutic agent could be instilled through a dilator device (such as was described above) that has been passed through the flow control device deployed at a target site in the patient's bronchial lumen. The therapeutic agent is instilled into the bronchial lumen or lumens distal to the implanted flow control device. Alternately, brachytherapy source or sources could be inserted through the dilator device and into the lumen or lumens distal to the flow control device to reduce or eliminate mucus production, to cause scarring, or for other therapeutic purposes.

The patient's blood can be de-nitrogenated in order to promote absorption of nitrogen in trapped airways. Utilizing any of the devices or methods above, the patient would either breath through a mask or be ventilated with heliox (helium-oxygen mixture) or oxygen combined with some other inert gas. This would reduce the partial pressure of nitrogen in the patient's blood, thereby increasing the absorption of nitrogen trapping in the lung spaces distal to the implanted flow control device.

As mentioned, one method of deflating the distal lung volume involves the use of pulsed vacuum instead of continuous vacuum. Pulsatile suction is defined as a vacuum source that varies in vacuum pressure from atmospheric pressure down to −10 cm $H_2O$. The frequency of the pulse can be adjusted so that the collapsed bronchus has time to re-open at the trough of the suction wave prior to the next cycle. The frequency of the pulse could be fast enough such that the bronchus does not have time to collapse at the peak of the suction wave prior to the next cycle. The suction force could be regulated such that even at the peak suction, the negative pressure is not low enough to collapse the distal airways. The frequency of the pulsatile suction could be set to the patient's respiratory cycle such that negative pressure is applied only during inspiration so that the lung's tethering forces are exerted keeping the distal airways open.

One possible method of implementing this described form of pulsatile suction would be to utilize a water manometer attached to a vacuum source. The vacuum regulator pipe in the water manometer could be manually or mechanically moved up and down at the desired frequency to the desired vacuum break point (0 to −10 cm). This describes only one of many methods of creating a pulsatile vacuum source.

At any point, the dilator device (if used) can be removed from the flow control device. This can be accomplished by pulling on a tether attached to the dilator device (such as was shown in FIG. 15), pulling on a catheter that is attached to the dilator device, or grasping the dilator device with a tool, such as forceps. After removal of the dilator device, another dilator device could be used to re-dilate the flow control device at a later time.

Asymmetric Delivery Catheter

During deployment of the flow control device 110 using an over-the-wire delivery catheter, navigating the delivery catheter 2915 past the lungs' carinae can frequently present difficulties, as the housing 2940 can often get stuck against the sharp edge of a carina or will not properly align with the ostium of a target bronchus. If the housing 2940 gets stuck, it can be very difficult to advance the catheter 2915 any further or to achieve a more distal placement.

Figure 74:
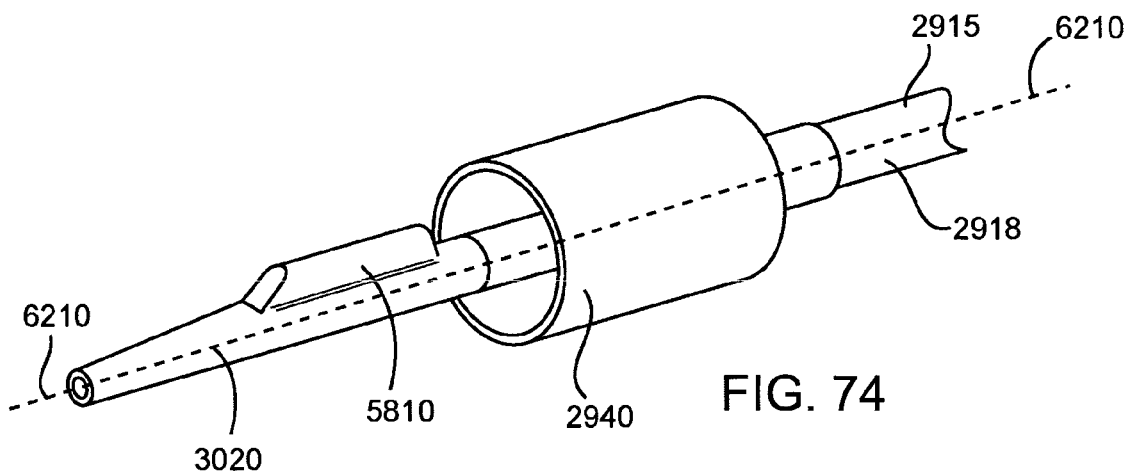
FIG. 74 shows a perspective view of a delivery catheter having an asymmetric, distal tip.
Figure 75:
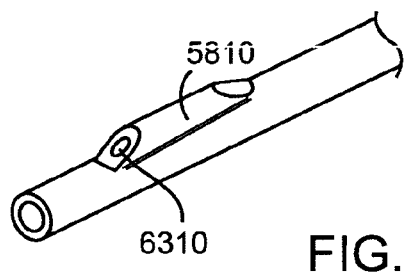
FIG. 75 shows a perspective view of another embodiment of a delivery catheter having an asymmetric, distal tip.

In order to ease the navigation of the housing past carinae and into the ostium of a target bronchus, the tip region 3020 of the catheter inner member 2920 can have a rib or elongate protrusion 5810 extending in one direction radially so as to provide the tip region 3020 with an asymmetric shape, such as is shown in FIGS. 74 and 75. The tip region 3020 is asymmetric with respect to a central longitudinal axis 6210 of the catheter 2915. The protrusion 5810 can extend radially, for example, as far as the outer diameter of the housing 2940. The protrusion 5810 extends only in one direction in order to minimize the perimeter of the tip region 3020, which facilitates passing the tip region 3020 through the central lumen of the flow control device 110. The protrusion 5810 can be made of a solid material (such as shown in FIG. 74) or, alternatively, the protrusion 5810 can be hollow (such as shown by reference numeral 6310 in FIG. 75) in order to allow some compressive compliance. The compliance would be such that the protrusion 5810 does not compress when pushed against lung tissue but would compress when it is pulled through the flow control device 110 or pushed into the lumen of a loading device.

By having the protrusion 5810 be compliant, the protrusion 5810 could be tall enough to extend to the outside diameter of the housing but then compress to a smaller size that would fit through the flow control device lumen or the loading device. Alternatively, two or more radially spaced protrusions could be added to the tip region 3020 of the catheter 2915 to provide a smooth transition between the tip region 3020 and the housing 2940. The protrusions 5810 could be made hollow or very soft so that they would easily collapse when inserted through the flow control device 110.

Figure 76:
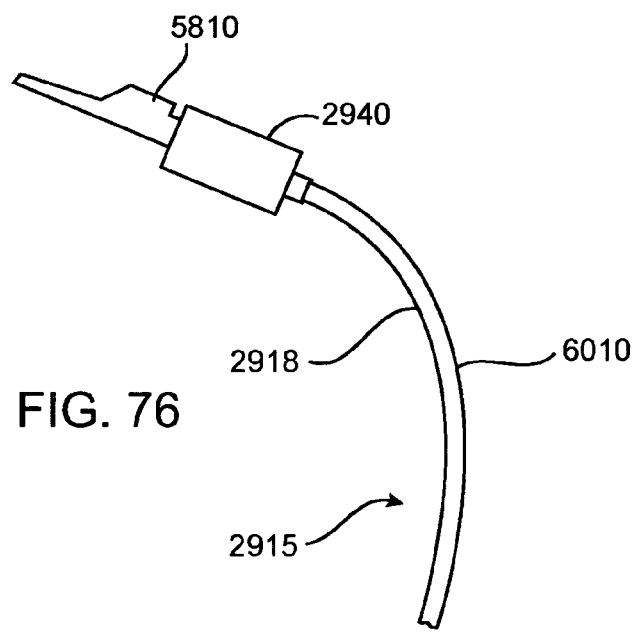
FIG. 76 shows a delivery catheter having a distal curve and an asymmetric distal tip.

As mentioned, the outer shaft 2918 of the delivery catheter 2915 could be shaped to contain a curve, biasing the whole catheter in one direction. In one embodiment, shown in FIG. 76, the curve 6010, if present, is contained within a single plane and is limited to a portion, such as 3 inches, of catheter length just proximal to the housing 2940. The plane of the outer shaft curve could be coincident with the plane containing the protrusion 5810 on the tip region 3020. In this manner, the curve in the outer shaft could be used to align the delivery catheter 2915 so that as the catheter 2915 is traveling over a curved guidewire it will have the protrusion 5810 always facing outward relative to the curve. Due to the three dimensional nature of the bronchial tree in the lungs, a useful geometry of the shaped end of the catheter may be a complex curve that bends in three dimension to match the lung anatomy, rather than being a simple curve in single plane (two dimensions). In addition, the proximal end of the catheter 2915 might be shaped to conform to the curve commonly found in endotracheal tubes to ease delivery if the patient is under general anesthesia and is being ventilated.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of regulating fluid flow to and from a region of an individual's lung, comprising:
   placing a flow control device in a bronchial passage in communication with the region, the flow control device having a first set of one or more deployable arms in a collapsed configuration; and
   radially expanding the first set of one or more deployable arms into engagement with a wall of the bronchial passage to anchor the flow control device therein;
   wherein the flow control device has a plurality of overlapping segments that are movable relative to one another and collectively form a seal with a wall of the bronchial lumen that can expand and contract in size.

2. A method as defined in claim 1, wherein the overlapping segments form a seal against fluid flow through the bronchial passage into the region and are movable to allow fluid flow through the bronchial passage out of the region.

3. A method as defined in claim 1, wherein the overlapping segments are supported by the first set of deployable arms.

4. A method as defined in claim 1, further comprising radially expanding a second set of one or more deployable arms into engagement with the wall of the bronchial passage.

5. A method as defined in claim 4, wherein the overlapping segments are supported by the second set of deployable arms.

6. A method as defined in claim 1 further comprising radially collapsing the first set of one or more deployable arms prior to placing the flow control device in the bronchial passage.

7. A method as defined in claim 6, wherein radially collapsing the deployable arms comprises positioning a sleeve over at least a portion of the one or more deployable arms.

8. A method as defined in claim 7, wherein the sleeve is slidably coupled to the flow control device.

9. A method as defined in claims 7, wherein positioning the sleeve comprises moving an actuator element coupled to the sleeve.

10. A method as defined in claim 1, further comprising removing the flow control device from the bronchial passage after radially expanding the first set of one or more deployable arms.

11. A method as defined in claim 10, wherein removing the flow control device comprises radially collapsing the first set of one or more deployable arms.

12. A method as defined in claim 11 wherein radially collapsing the first set of one or more deployable arms comprises positioning a sleeve over at least a portion of the one or more deployable arms.

13. A method as defined in claim 1, wherein the overlapping segments collectively form a conical shape and wherein the diameter of the conical shape can vary as one segment moves with respect to another segment.

* * * * *

UNITED STATES PATENT AND TRADEMARK OFFICE
CERTIFICATE OF CORRECTION

PATENT NO. : 7,011,094 B2
APPLICATION NO. : 10/627517
DATED : March 14, 2006
INVENTOR(S) : Rapacki et al.

It is certified that error appears in the above-identified patent and that said Letters Patent is hereby corrected as shown below:

On the Title Page:
IN THE REFERENCES CITED [56]:
In U.S. PATENT DOCUMENTS:
pg 2 col 1
in 5,954,766 please replace "1.24" with --2--

In pg 2 col 2:
in 6,123,663 please include --600/37-- in the Class/Subclass column
in 6,485,407 please replace "B1" with --B2--

In pg 3 col 1:
in 2004/0055606 please replace "Hendrickson" with --Hendricksen--

In OTHER PUBLICATIONS:
pg 3
in Article:, following "Development" please insert
  --available at <http://www.kulisz.com/autocath.htm>,
  last accessed Jul. 9, 2002--
in Woodring et al., please replace "100" with --110--, and replace "1124" with --1105--

UNITED STATES PATENT AND TRADEMARK OFFICE
CERTIFICATE OF CORRECTION

PATENT NO. : 7,011,094 B2
APPLICATION NO. : 10/627517
DATED : March 14, 2006
INVENTOR(S) : Rapacki et al.

It is certified that error appears in the above-identified patent and that said Letters Patent is hereby corrected as shown below:

IN THE SPECIFICATION:
at column 21, line 8, please insert --be-- between "can" and "made"
at column 31, line 48, please insert --is--between "device" and "in"
at column 43, between lines 43 & 44, please insert the follwing items:
 --(1) Antibiotic agents to inhibit growth of microorganisms (sirolimus, doxycycline, minocycline, bleomycin, tetracycline, etc.)
 (2) Antimicrobial agents to prevent the multiplication or growth of microbes, or to prevent their pathogenic action.--

IN THE CLAIMS:
Column 48, lines 23-25
Please replace Claim 9 with the following Claim:

9. A method as defined in claim 7, wherein positioning the sleeve comprises moving an actuator element coupled to the sleeve.

Signed and Sealed this

Nineteenth Day of September, 2006

JON W. DUDAS
*Director of the United States Patent and Trademark Office*